US006958238B2

(12) United States Patent (10) Patent No.: US 6,958,238 B2
Sun et al. (45) Date of Patent: Oct. 25, 2005

(54) ISOLATED DISHEVELLED ASSOCIATED KINASES, POLYNUCLEOTIDES ENCODING THE KINASES, AND METHODS OF USE THEREOF

(75) Inventors: Tian-Qiang Sun, San Francisco, CA (US); Lewis T. Williams, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 8 days.

(21) Appl. No.: 10/464,939

(22) Filed: Jun. 18, 2003

(65) Prior Publication Data

US 2004/0005688 A1 Jan. 8, 2004

Related U.S. Application Data

(63) Continuation of application No. 09/661,965, filed on Sep. 14, 2000, now abandoned.
(60) Provisional application No. 60/158,021, filed on Oct. 6, 1999.

(51) Int. Cl.$^7$ .............................. C12N 15/54; C12N 9/12
(52) U.S. Cl. .................... 435/325; 435/194; 435/252.3; 435/320.1; 536/23.2
(58) Field of Search ........................... 435/320.1, 252.3, 435/325, 194; 536/23.2

(56) References Cited

PUBLICATIONS

Aberle et al. (1995) "The human plakoglobin gene localizes on chromosome 17q21 and is subjected to loss of heterozygosity in breast and ovarian cancers." *Proc. Natl. Acad. Sci.*, vol. 92: 6384–6388.

Aoki et al. (1999) "Nuclear endpoint of Wnt signaling: Neoplastic transformation induced by transactivating lymphoid–enhancing factor 1." *Proc. Natl. Acad. Sci.*, vol. 96:139–144.

Behrens et al. (1998) "Functional Interaction of an Axin Homolog Conductin, with β–Catenin, APC, and GSK3β." *Science*, vol. 280:596–599.

Ben–Ze'ev et al. (1998) "Differential molecular interactions of β–catenin and plakoglobin in adhesion, signaling and cancer." *Curr. Opin. Cell Biol.*, vol. 10:629–639.

Boutros et al. (1998) "Dishevelled Activates JNK and Discriminates between JNK Pathways in Planar Polarity and wingless Signaling." *Cell*, vol. 94:109–118.

Cadigan et al. (1997) "Wnt signaling: a common theme in animal development." *Genes & Development*, vol. 11:3286–3305.

Crawford et al. (1999) "The metalloproteinase matrilysin is a target of β–catenin transactivation in intestinal tumors." *Oncogene*, vol. 18:2883–2891.

Fernandez et al. (1998) "Routine identification of proteins from sodium dodecyl sulfate–polyacrylamide gel electrophoresis (SDS–PAGE) gels or polyvinyl difluoride membranes using matrix assisted laser desorption/ionization–time of flight–mass spectrometry (MALDI–TOF–MS)." *Electrophoresis*, vol. 19:1036–1045.

Hsu et al. (1998) "Modulation of Transcriptional Regulation by LEF–1 in Response to Wnt–1 Signaling and Association with β–Catenin." *Molecular and Cellular Biology*, vol. 18(8):4807–4818.

Ikeda et al. (1998) "Axin, a negative regulator of the Wnt Signaling pathway, forms a complex with GSK–3βand β–catenin and promotes GSK–3β–dependent phosphorylation of βcatenin." *The EMBO Journal*, vol. 17(5):1371–1384.

Itoh et al. (1998) "Axis determination in *Xenopus* involves biochemical interactions of axin, glycogen synthase kinase 3 and β–catenin." *Current Biology*, vol. 8:591–594.

Klingensmith et al. (1994) "The *Drosophila* segment polarity gene dishevelled encodes a novel protein required for response to the wingless signal." *Genes & Development*, vol. 8:118–130.

Klingensmith et al. (1996) "Conservation of dishevelled structure and function between flies and mice: isolation and characterization of Dvl2." *Mechanisms of Development*, vol. 58:15–26.

Kolligs et al. (1999) "Neoplastic Transformation of RK3E by Mutant β–Catenin Requires Deregulation of Tcf/Lef. Transcription but Not Activation of c–myc Expression." *Molecular and Cellular Biology*, vol. 19(8):5696–5706.

Lee et al. (1999) "Characterization of Mouse Dishevelled (Dvl) Proteins in Wnt/Wingless Signaling Pathway." *The Journal of Biological Chemistry*, vol. 274(30): 21464–21470.

Lijam et al. (1997) "Social Interaction and Sensorimotor Gating Abnormalities in Mice Lacking Dvl1." *Cell*, vol. 90:895–905.

Mai et al. (1999) "Cloning of the Human Homolog of Conduction (AXIN2), a Gene Mapping t Chromosome–17q23–q24." *Genomics*, vol. 55: 341–344.

McMahon et al. (1992) "The Wnt family of developmental regulators." *Trends in Genetics*, vol. 8(7): 236–242.

(Continued)

*Primary Examiner*—Rebecca Prouty
(74) *Attorney, Agent, or Firm*—Paula A. Borden; Bozicevic, Field & Francis LLP

(57) ABSTRACT

The invention provides Dishevelled Associated Kinase polypeptides, which phosphorylate Dsh proteins involved in the Wnt/Wg signalling pathway. Isolated polynucleotides encoding DAK polypeptides are further provided, as are recombinant vectors, and host cells comprising the polynucleotides. Methods of using the polynucleotides and polypeptides of the invention are further aspects of the invention, including assays to detect agents which modulate DAK kinase activity. Further provided are methods of modulating pathways involved in control of cell proliferation.

7 Claims, 13 Drawing Sheets

OTHER PUBLICATIONS

Nusse et al. (1992) "Wnt Genes." *Cell*, vol. 69: 1073–1087.

Nusslein–Volhard et al. (1980) "Mutations affecting segment number and polarity in *Drosophila*:" *Nature*, vol. 287: 795–801.

Palacios et al. (1998) "Mutations in the β–Catenin Gene (CTNNB1) in Endometrioid Ovarian Carcinomas." *Cancer Research*, vol. 58:1344–1347.

Peifer (1997) "β–Catenin as Oncogene: The Smoking Gun." *Science*, vol. 275:1752–1753.

Polakis (1999) "The oncogenic activation of β–catenin." *Current Opinion in Genetics & Development*, vol. 9:15–21.

Ponting et al. (1996) "Pleckstrin's repeat performance: a novel domain in G–protein signaling?" *Trends in Biochemical Sciences*, vol. 21:245–246.

Ramakrishna et al., (1993) "Wingless, the *Drosophila* homolog of the proto–oncogene Writ–1, can transform mouse mammary epithelial cells." *Development Supplement*, 95–103.

Rijsewijk et al. (1987) "The *Drosophila* Homolog of the Mouse Mammary Oncogene int–1 is Identical to the Segment Polarity Gene wingless." *Cell*, vol. 50:649–657.

Rothbacher et al. (1995) "Functional Conservation of the Writ Signaling Pathway Revealed by Ectopic Expression of *Drosohila* disheveled in *Xenopus*." *Developmental Biology*, vol. 170:717–721.

Rubinfeld et al. (1997) "Stabilization of β–Catenin by Genetic Defects in Melanoma Cell Lines." *Science*, vol. 275:1790–1792.

Ruvkun et al. (1998) "The Taxonomy of Developmental Control in Caenorhabditis elegans." *Science*, vol. 282:2033–2041.

Sharma et al. (1976) "Effect of the Wingless (wg[1]) Mutation on Wing and Haltere Development in *Drosophila melanogaster*." *Developmental Biology*, vol. 48:461–465.

Siegfried et al. (1992) "wingless Signaling Acts through zeste–white 3, the *Drosohila* Homolo of glycogen synthase kinase–3, to Regulate engrailed and Establish Cell Fate." *Cell*, vol. 71:1167–1179.

Sokol et al. (1995) "Dorsalizing and neuralizing properties of Xdsh, a maternally expressed *Xenopus* homolog of disheveled." *Development*, vol. 121:3487.

Sparks et al. (1998) "Mutational Analysis of the APC/β–Catenin/Tcf Pathway in Colorectal Cancer." *Cancer Research*, vol. 58:1130–1134.

Theisen et al. (1994) "dishevelled is required during wingless signaling to establish both cell polarity and cell identity." *Development*, vol. 120:347–360.

Van de Wetering et al. (1997) "Armadillo Coactivates Transcription Driven by the Product of the *Drosophila* Segment Polarity Gene dTCF." *Cell*, vol. 88:789–799.

Van Leeuwen et al. (1994) "Biological activity of soluble wingless protein in culture *Drosophila* imaginal disc cells." *Nature*, vol. 368:342–344.

Yanagawa et al. (1995) "The Dishevelled protein is modified by Wingless signaling in *Drosophila*." *Genes & Development*, vol. 9:1087–1097.

Zeng et al. (1997) "The Mouse Fused Locus Encodes Axin, an Inhibitor of the Wnt Signaling Pathway That Regulates Embryonic Axis Formation." *Cell*, vol. 90: 181–192.

Zurawel et al. (1998) "Sporadic Medulloblastomas Contain Oncogenic β–Catenin Mutations." *Cancer Research*, vol. 58:896–899.

Guo, S. et al. (May 19, 1995), "A Gene Required for Establishing Polarity in C. Elegans Embryos, Encodes a Putative Ser\Thr Kinase That is Asymmetrically Distributed." *Cell*, vol. 81:611–620.

GENBANK Accession No. AF258462, Shulman et al. (May 23, 2000).

Shulman, J.M. et al. (May 12, 2000), "The *Drosophila* Homolog of C. Elegans PAR–1 Organizes the Oocyte Cytoskeleton and Directs oskar mRNA Localization to the Posterior Pole." *Cell*, vol. 101:377–388.

Sun, T. et al. (Dec. 1996), "A Disheveled Association Kinase and Its Possible Role in Wingless Pathway." *Mol. Biol. Cell*, vol. 7:488a.

Database EMBL, Accession No. AC004299, Celniker, S.E. et al. (Mar. 13, 1998).

FIG. 4A

| | | |
|---|---|---|
|DAKa|ENLLLDSELNIKIADFGFSNEFTPGSKLDTFCGSPPYAAPELFQGKKYDGPEVDVWSLGV|438|
|DAKb|ENLLLDSELNIKIADFGFSNEFTPGSKLDTFCGSPPYAAPELFQGKKYDGPEVDVWSLGV|666|
|DAKa|ILYTLVSGSLPFDGSTLRERVLRGKYRIPFYMSTDCENLLRKFLVLNPAKRASLETI|498|
|DAKb|ILYTLVSGSLPFDGSTLRERVLRGKYRIPFYMSTDCENLLRKFLVLNPAKRASLETI|726|
|DAKa|MGDKWMNMGFEEDELKPYIEPKADLADPKRI---EALVAMGYNRSEIEASLSQVRYDDVF|555|
|DAKb|MGDKWMNMGFEEDELKPYIEPKADLADPKRIGKTEALVAMGYNRSEIEASLSQVRYDDVF|786|
|DAKa|ATYLLLGRKSTDPESDGSRSGSSLSLRNISGNDAGANAGSASVQSPTHRGVHRSISASST|615|
|DAKb|ATYLLLGRKSTDPESDGSRSGSSLSLRNISGNDAGANAGSASVQSPTHRGVHRSISASST|846|
|DAKa|KPSRRASSGAETLRVGPTNAAATGAVGAVNPSNNYNAAGSAADRASVGSNFKRQN|675|
|DAKb|KPSRRASSG---VGPTNAAATGAVGAVNPSNNYNAAGSAADRASVGSNFKRQN|901|
|DAKa|TIDSATIKENTARLAAQNQRPASATQKMLTTADTTLNSPAKPRTATKYDPTNGNRTVSGT|735|
|DAKb|TIDSATIKENTARLAAQNQRPASATQKMLTTADTTLNSPAKPRTATKYDPTNGNRTVSGT|961|
|DAKa|SGIIPRRSTTLYEKTSSTEKTNVIPAETKMASAVKSSRHFPRNVPSRSTFHSGQTRARNN|795|
|DAKb|SGIIPRRSTTLYEKTSSTEKTNVIPAETKMASAVKSSRHFPRNVPSRSTFHSGQTRARNN|1021|
|DAKa|TALEYSGTSGASGDSSHPGRMSFFSKLSSRFSKRPNQ|832|
|DAKb|TALEYSGTSGASGDSSHPGRMSFFSKLSSRFSKRPNQ|1058|

FIG. 4B

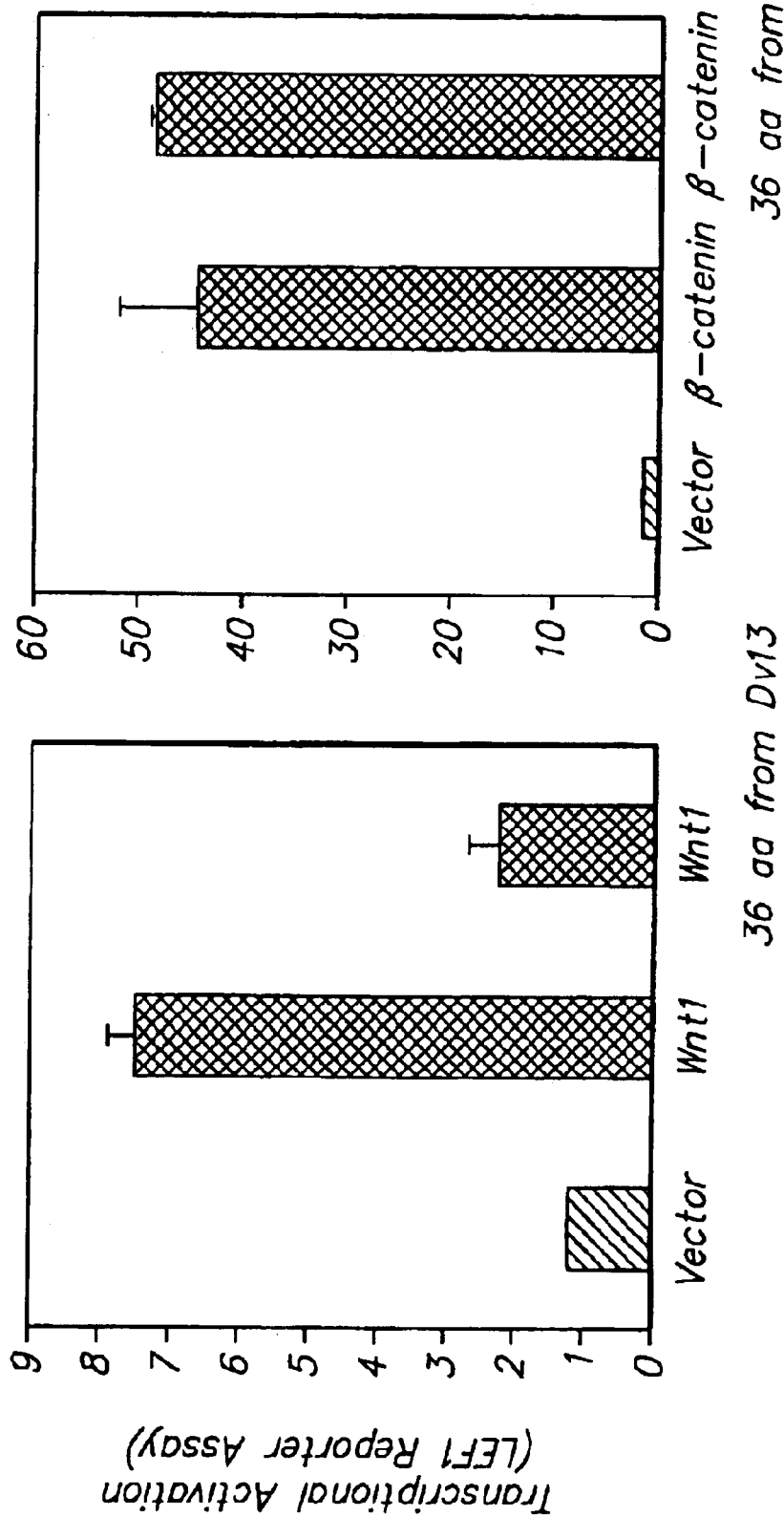

ClustalW Formatted Alignments

```
DAKa aa seq        1                                         0
DAKb aa seq        1  M E A T T T T T P D L N R G D A T R K S V R L Y A A R K G A A P A P P  35
DAKc C-ter aa seq  1                                         0

DAKa aa seq        1                                         0
DAKb aa seq       36  K L S V A P S S N Q N S N H S S N N N N S S S N L P E T E K E-M E L R  70
DAKc C-ter aa seq  1                                         0

DAKa aa seq        1                                         0
DAKb aa seq       71  Q T H L A N K D L D G A T E D D S I V E L R R R D A Q A T P L P R I A  105
DAKc C-ter aa seq  1                                         0

DAKa aa seq        1                                         0
DAKb aa seq      106  V S A L P T L Q P H P T P K E R Q K P P M P R L L S T E D D A G V S F  140
DAKc C-ter aa seq  1                                         0

DAKa aa seq        1                                         0
DAKb aa seq      141  A L G S I E K H I H N V E E S F K Q Q Q Q N Q Q S Q S S M D V M K L E  175
DAKc C-ter aa seq  1                                         0

DAKa aa seq        1                                    M S T A M R T T L Q S V  12
DAKb aa seq      176  I K R K Q S K R Y G E T E N L L R P G I S D M S S E N D F Q Y L G G R  210
DAKc C-ter aa seq  1                                         0

DAKa aa seq       13  P E A L P A D S - - - - - - - - - - - V S N G T A S N V A A P - - - A A  34
DAKb aa seq      211  R A G E L D D S N E L M L S E F Q R G S D G R N S I G A Y S K N S A A  245
DAKc C-ter aa seq  1                                         0

DAKa aa seq       35  P V S S A T N A V P P L A A V S S T T A T Y A T N S I S T S S H S V K  69
DAKb aa seq      246  A A N G A N A V K A K L A R T A S D T K N N D T V L A M R A T F K Q K  280
DAKc C-ter aa seq  1                                         0

DAKa aa seq       70  D Q Q Q Q Q Q Q Q H D S A N A N I V S L P P T T T P V A N T N T M M  104
DAKb aa seq      281  - Q H L Q D E K Q P A V W R P A G T G P T P A A R S S S T T S T S G  314
DAKc C-ter aa seq  1                                         0

DAKa aa seq      105  P I V T S S N S - - - - - - - - A T S N S T A A T P T P A S G - - - - -  127
DAKb aa seq      315  S A S R G G S S S S V V D G V A P S K L T A T I S A S K R R E E N L  349
DAKc C-ter aa seq  1                                         0

DAKa aa seq      128  - - - A A T G G V G S V S Q G P A T V S A S A A N T N H S H Q H S H  159
DAKb aa seq      350  R Q F E A L L A Q K S S H R H G A S G A S G T G S N A A S K R R S D  384
DAKc C-ter aa seq  1                                         0
```

FIG. 8A

```
DAKa aa seq      160 QHHHHVANNMTTDGARLSSNNSAVVASSAINHHHH 194
DAKb aa seq      385 R--PIVAPIPPYNSSRAEHVTSSTRHSVDPRSHSG 417
DAKc C-ter aa seq  1                                              0

DAKa aa seq      195 HTPGSGVAPTVNKNVLSTHSAHPSAIKQR-----T 224
DAKb aa seq      418 HESRSGTASIHPPVGHHPTSRVPSVVANRSNVYSN 452
DAKc C-ter aa seq  1                                              0

DAKa aa seq      225 SSAKGSPNMQMRSSAPMRWRATEEHIGKYKLIKTI 259
DAKb aa seq      453 NAAQGSPNMQMRSSAPMRWRATEEHIGKYKLIKTI 487
DAKc C-ter aa seq  1                                              0

DAKa aa seq      260 GKGNFAKVKLAKHLPTGKEVAIKIIDKTQLNPGSL 294
DAKb aa seq      488 GKGNFAKVKLAKHLPTGKEVAIKIIDKTQLNPGSL 522
DAKc C-ter aa seq  1                                              0

DAKa aa seq      295 QKLFREVRIMKMLDHPNIVKLFQVIETEKTLYLIM 329
DAKb aa seq      523 QKLFREVRIMKMLDHPNIVKLFQVIETEKTLYLIM 557
DAKc C-ter aa seq  1                                              0

DAKa aa seq      330 EYASGGEVFDYLVLHGRMKEKEARVKFRQIVSAVQ 364
DAKb aa seq      558 EYASGGEVFDYLVLHGRMKEKEARVKFRQIVSAVQ 592
DAKc C-ter aa seq  1                                              0

DAKa aa seq      365 YCHQKRIIHRDLKAENLLLDSELNIKIADFGFSNE 399
DAKb aa seq      593 YCHQKRIIHRDLKAENLLLDSELNIKIADFGFSNE 627
DAKc C-ter aa seq  1                                              0

DAKa aa seq      400 FTPGSKLDTFCGSPPYAAPELFQGKKYDGPEVDVW 434
DAKb aa seq      628 FTPGSKLDTFCGSPPYAAPELFQGKKYDGPEVDVW 662
DAKc C-ter aa seq  1                                              0

DAKa aa seq      435 SLGVILYTLVSGSLPFDGSTLRELRERVLRGKYRI 469
DAKb aa seq      663 SLGVILYTLVSGSLPFDGSTLRELRERVLRGKYRI 697
DAKc C-ter aa seq  1                                              0

DAKa aa seq      470 PFYMSTDCENLLRKFLVLNPAKRASLETIMGDKWM 504
DAKb aa seq      698 PFYMSTDCENLLRKFLVLNPAKRASLETIMGDKWM 732
DAKc C-ter aa seq  1                                              0

DAKa aa seq      505 NMGFEEDELKPYIEPKADLADPK---RIEALVAMG 536
DAKb aa seq      733 NMGFEEDELKPYIEPKADLADPKRIGKTEALVAMG 767
DAKc C-ter aa seq  1                                              0

DAKa aa seq      537 YNRSEIEASLSQVRYDDVFATYLLLGRKSTDPESD 571
DAKb aa seq      768 YNRSEIEASLSQVRYDDVFATYLLLGRKSTDPESD 802
DAKc C-ter aa seq  1                                              0
```

*FIG. 8B*

| | | | |
|---|---|---|---|
| DAKa aa seq | 572 | GSRSGSSLSLRNISGNDAGANAGSASVQSPTHRGV | 606 |
| DAKb aa seq | 803 | GSRSGSSLSLRNISGNDAGANAGSASVQSPTHRGV | 837 |
| DAKc C-ter aa seq | 1 | | 0 |
| DAKa aa seq | 607 | HRSISASSTKPSRRASSG AETLR VGPTNAAATVAA | 641 |
| DAKb aa seq | 838 | HRSISASSTKPSRRASSG------VGPTNAAATVAA | 867 |
| DAKc C-ter aa seq | 1 | | 0 |
| DAKa aa seq | 642 | ATGAVGAVNPSNNYNAAGSAADRASVGSNFKRQNT | 676 |
| DAKb aa seq | 868 | ATGAVGAVNPSNNYNAAGSAADRASVGSNFKRQNT | 902 |
| DAKc C-ter aa seq | 1 | | 0 |
| DAKa aa seq | 677 | IDSATIKENTARLAAQNQRPASATQKMLTTADTTL | 711 |
| DAKb aa seq | 903 | IDSATIKENTARLAAQNQRPASATQKMLTTADTTL | 937 |
| DAKc C-ter aa seq | 1 | | 0 |
| DAKa aa seq | 712 | NSPAKPRTATKYDPTNGNRTVSGTSGIIPRRSTTL | 746 |
| DAKb aa seq | 938 | NSPAKPRTATKYDPTNGNRTVSGTSGIIPRRSTTL | 972 |
| DAKc C-ter aa seq | 1 | | 0 |
| DAKa aa seq | 747 | YEKTSSTEKTNVIPAETKMASAVKSSRHFPRNVPS | 781 |
| DAKb aa seq | 973 | YEKTSSTEKTNVIPAETKMASAVKSSRHFPRNVPS | 1007 |
| DAKc C-ter aa seq | 1 | | 0 |
| DAKa aa seq | 782 | RSTFHSGQTRARNNTALEYSGTSGASGDSSHPGRM | 816 |
| DAKb aa seq | 1008 | RSTFHSGQTRARNNTALEYSGTSGASGDSSHPGRM | 1042 |
| DAKc C-ter aa seq | 1 | SGQTRARNNTALEYSGTSGASGDSSHPGRM | 30 |
| DAKa aa seq | 817 | SFFSKLSSRFSKRPNQ | 832 |
| DAKb aa seq | 1043 | SFFSKLSSRFSKRPNQ | 1058 |
| DAKc C-ter aa seq | 31 | SFFSKLSSRFSKRPTI ADEAAKPRVLRFTWSMKTT | 65 |
| DAKa aa seq | 833 | | 832 |
| DAKb aa seq | 1059 | | 1058 |
| DAKc C-ter aa seq | 66 | SPLMPDQIMQKIREVLDQNNCDYEQRERFVLWCVH | 100 |
| DAKa aa seq | 833 | | 832 |
| DAKb aa seq | 1059 | | 1058 |
| DAKc C-ter aa seq | 101 | GDPNTDSLVQWEIEVCKLPRLSLNGVRFKRISGTS | 135 |
| DAKa aa seq | 833 | | 832 |
| DAKb aa seq | 1059 | | 1058 |
| DAKc C-ter aa seq | 136 | IGFKNIASRIAFDLKL | 151 |

FIG. 8C

```
AGAGACCGAGACGTACATACTTTTGTTGCTGCCAAAGTGGATGTGGACGGAGGAAAATAGTAATATTTAAC
TGCGTTGCGGGAGCGGGACAATCGTCGTTTGCCAATTGCGGCCACCGCTTATGTCGGCTAATCGGCTATCA
ATAATATTAGTAATCGTATCAATATCAAGTTACCCATTACCCATCGCGGATACACATTAGTTTTGCGAAGG
GCAGAGCAGCGCAGAGCATATAGCGAATATTTCCATTTGTTGCCAACAAGACTGTCGTTGTTGTTGTTATT
ATTGTGGCTTTTCAGTGACTGGGGAGAGCAGTGGGGGTGCGTTCGTAATCCTTGTGAAAATCGGTGACCG
TTCTTCTTAAAAAAAAAGCGAAAGAAAAAACCATCGCGATAAGAAAATATAAGAAAGAAAAATCTGATTGA
AAACCAAAGAGCTGCTGCTACTGCTGCTGTGCGAGTGAGAGCGGTCGAGAGGTAGCTAGTGAGCGAGTGAG
AAAGCTATGTATTGCATTTGCATTTCGTTGTGTGTGTCGTCGTTTTCGTTCGGTAAAAGTCGGTAAAAAGC
AGAGCCTTTCCAAACCTAACCACTTTCGGGTAAACGGAATCGGAAAAGGAACTGGGAAAATCGAAAGAAAT
TAAATAATAATATGCGTTACATCGATGGCAACAACAACAACAACAGCAGCGACCATCAGCTAGCGACTCCT
CTCTGAGCGAGAGAGCTAATAGCTTTTCAGCTTTAGCTTTTCTTGGGCCAATCGGAAATTGTATTTCATTG
ATGTGAAGGAGTACCACGGATGATAGAAACCCATTGGGCATTTGACTACTTTTAAGCACCGAAACCTGAAA
GACTCCCGAAAATACTCGAATCTCACGTGCAGAATCTCTAAGAATCCCTATTGGACTGTTTAAAAATATGT
CGACAGCAATGCGCACCACACTGCAGTCAGTTCCTGAGGCCCTGCCAGCGGATAGCGTGTCCAATGGCACA
GCATCCAATGTAGCAGCACCGGCGGCGCCAGTATCGAGCGCAACAAACGCGGTGCCACCACTGGCCGCCGT
CTCCAGCACAACCGCCACCTACGCCACCAACTCGATCAGCACATCCTCGCATTCGGTCAAGGATCAGCAGC
AGCAACAGCAGCAGCAGCAGCATGATTCGGCCAATGCAAACATTGTGTCACTGCCACCAACGACAACGCCA
GTCGCCAACACTAACACAATGATGCCCATTGTAACGTCCTCGAATTCGGCCACCAGCAATAGCACTGCGGC
CACGCCCACGCCGGCCTCGGGGCGGCAGCGACAGGTGGAGTGGGATCAGTTTCGCAGGGTCCAGCGACCG
TTTCGGCGTCAGCGGCCAACACCAATCACTCGCACCAGCACAGCCACCAACACCACCACCATGTGGCCAAC
AACATGACCACCGACGGTGCCCGCTTGTCCAGCAACAATTCGGCGGTGGTGGCGAGCTCAGCGATTAACCA
CCACCATCACCACACCCCCGGCAGTGGAGTGGCGCCCACCGTCAACAAGAACGTGCTTAGCACCCACTCGG
CTCATCCCTCCGCGATCAAGCAACGAACCTCGTCCGCCAAGGGTTCGCCTAACATGCAAATGCGGAGTAGT
GCTCCTATGCGATGGCGTGCTACTGAGGAGCATATTGGCAAATACAAACTCATAAAGACGATCGGCAAGGG
CAATTTTGCCAAGGTGAAACTAGCGAAACACCTGCCCACTGGCAAGGAGGTCGCCATCAAGATAATTGACA
AGACCCAACTCAATCCTGGGTCACTACAGAAACTCTTTAGAGAGGTTAGAATAATGAAGATGCTGGATCAC
CCCAACATAGTTAAATTGTTCCAAGTAATCGAAACGGAGAAGACGCTCTATCTGATCATGGAGTACGCATC
TGGCGGAGAAGTCTTCGACTACCTGGTTCTCCACGGACGCATGAAGGAGAAGGAGGCGCGAGTTAAGTTTC
GACAAATCGTCTCAGCCGTGCAATATTGTCATCAAAAAAGAATAATTCACAGGGACTTAAAAGCTGAAAAC
CTTTTGCTGGACAGCGAACTGAACATCAAAATCGCTGACTTTGGCTTTTCGAACGAGTTCACACCCGGCTC
AAAGCTGGACACGTTCTGCGGTAGCCCGCCATATGCGGCACCGGAGCTGTTTCAGGGCAAAAAGTACGACG
GACCGGAGGTCGATGTTTGGTCGCTGGGCGTCATCCTGTATACGTTAGTGAGCGGTTCCCTGCCCTTCGAC
GGCTCCACCTTGAGGGAGTTGCGTGAACGCGTGCTCAGAGGCAAATATAGAATTCCCTTCTATATGTCGAC
TGACTGCGAAAACTTGCTCCGCAAATTCTTAGTACTGAATCCCGCAAAGCGTGCTAGTCTGGAAACAATCA
TGGGCGACAAGTGGATGAACATGGGGTTTGAGGAGGACGAACTCAAGCCCTATATTGAGCCCAAAGCCGAT
TTAGCCGATCCCAAGCGGATAGAAGCTCTAGTCGCGATGGGCTACAATCGATCGGAGATCGAGGCTTCGCT
CTCCCAGGTGCGCTACGACGATGTTTTCGCCACATATTTGCTGCTGGGTCGCAAGAGTACAGACCCGGAAA
GTGACGGATCGCGGTCTGGCTCCTCGCTCTCACTGCGCAACATCTCGGGTAATGATGCGGGCGCCAATGCT
GGTAGTGCGAGTGTTCAGAGTCCCACGCACAGAGGAGTCCACAGGAGCATATCGGCGTCTAGCACGAAGCC
AAGTCGCCGAGCCTCGTCTGGTGCGGAAACTTTGCGTGTTGGACCGACAAATGCGGCAGCAACAGTTGCGG
CGGCCACGGGAGCCGTTGGTGCGGTTAATCCAAGCAATAACTACAATGCTGCAGGATCAGCGGCGGATCGA
GCATCAGTTGGCAGCAACTTTAAGCGACAGAACACAATCGACTCGGCTACGATTAAGGAGAACACAGCGCG
ACTGGCCGCTCAAAATCAGAGACCCGCTTCGGCCACACAAAAGATGCTCACCACGGCAGACACCACACTGA
ACAGTCCCGCCAAGCCGCGAACGGCAACGAAGTACGATCCGACGAATGGCAATCGCACGGTCAGCGGCACA
AGTGGCATCATTCCACGTCGCTCCACCACGCTTTATGAAAAGACTTCGTCGACGGAGAAAACCAACGTTAT
TCCTGCAGAGACAAAAATGGCATCGGCTGTTAAATCAAGCAGACACTTTCCAAGGAATGTTCCATCACGTT
CAACCTTTCACTCTGGTCAAACCAGAGCACGAAACAACACAGCGCTGGAATACTCGGGCACCAGCGGTGCC
TCCGGCGACTCCTCCCATCCGGGTCGCATGAGCTTCTTCTCCAAACTCTCCTCACGTTTTAGCAAACGGCC
AAACCAGTAATTAACAAAACAAGCATTAACTACTTCTTGTTAATAGTTCTAAAACTGAAACTGAAACAAAC
GATTCCCCTAGAGTAAACGCGCGTGACGGAGAGGTTCAGATATGAACAGACAGACACAGATATGGTCGAAT
CCAATCGGATCGCTCGGATCGGATCAGATCGGGAAACGATACTGTTCACGTTGCCGTTGCCGATCCGAAAT
CGCTTTCGAATTCCATTTCGAGTTCAGATCCGTTTCCGGTTTCGATTCGAACCCCTTCAAATGAACACCGA
CAACGTTGAGTTCCATTGCGTTAATTGAAATTTCACAAATACGCCTATGTTTTATTACAATTATTAACTAA
TTATACATATAAATTTATATAAATTAAAGATACATATACATATATTTAAAAGTAAAGCAACCACAAACAGA
AATTAAAAAAAAAAAAAAAAAAA
```

FIG. 9

```
AGAACAATAAACACGCCAAGCGCAACTTGAAAAAGAAATAAGAAAAAAGAAAAAGTTGCGATCTCTCCGAG
CAACAAGTACTTGTGCACCAACACACTCAAGGGAAGAGTGCCACGACAAAAAAATTTAAGAGAAAAAAAAC
AGAAAAACCGAAATCAGCAGCAAAACGGAGGAGCTATGGAGGCCACCACTACCACAACACCTGACTTGAAT
CGCGGCGATGCCACCAGGAAGAGTGTCCGGCTGTATGCCGCCCGCAAGGGGCGGCACCTGCGCCGCCCAA
GCTCAGTGTGGCGCCATCTAGTAACCAGAACAGCAACCACAGCAGCAACAACAACAATAGCAGCAGTAACT
TGCCGGAAACGGAAAAGGAAATGGAACTGCGTCAAACACATCTTGCCAACAAGGATCTCGATGGAGCCACC
GAAGACGACAGCATAGTGGAGCTTCGACGACGTGATGCCCAAGCCACTCCATTGCCCAGGATAGCCGTATC
GGCTCTACCCACCCTACAGCCGCATCCCACGCCCAAAGAACGCCAAAAGCCGCCAATGCCACGCCTTCTGT
CCACCGAAGACGATGCCGGTGTGTCCTTTGCCCTCGGCTCCATCGAGAAGCACATCCATAACGTGGAGGAG
AGCTTTAAGCAACAGCAGCAAAACCAACAATCCCAATCATCGATGGACGTGATGAAACTGGAGATCAAGCG
CAAGCAGAGCAAGCGCTACGGTGAAACGGAAAACCTTCTGCGACCGGGCATTAGTGACATGTCCTCCGAGA
ATGATTTTCAGTATTTGGGCGGCAGGCGGGCAGGAGAACTGGATGACAGCAATGAGCTGATGTTATCGGAA
TTCCAGCGCGGCAGCGATGGTCGTAACTCGATCGGAGCCTATTCCAAGAACTCGGCTGCTGCCGCAAACGG
AGCAAATGCTGTGAAGGCTAAACTGGCACGTACTGCCTCCGATACGAAGAATAATGATACGGTGCTGGCCA
TGAGGGCCACTTTTAAGCAGAAGCAGCACTTGCAGGACGAGAAACAGCCAGCGGTATGGCGACCAGCTGGC
ACTGGACCCACTCCGGCGGCCAGGAGCTCCTCCTCCACCACGTCCACCTCCGGCTCGGCCAGTCGTGGCGG
TAGCAGCAGCAGCGTGGTGGATGGAGTGGCTCCATCTAAGCTTACGGCCACTACCATTTCAGCGTCTAAGC
GGCGTGAGGAGAATTTGCGACAATTTGAAGCTTTGTTGGCCCAAAAATCCTCACATCGTCATGGAGCATCT
GGTGCCTCGGGAACAGGAAGTAATGCAGCCAGTTCGAAAAGACGTTCGGACCGGCCGATTGTGGCTCCTAT
TCCTCCGTACAATTCCAGTCGAGCAGAGCATGTGACCAGCTCGACCAGACACAGCGTTGATCCAAGATCCC
ATTCGGGACACGAGTCGAGGTCAGGAACAGCCTCAACTCACCCGCCTGTAGGACATCATCCCACTAGCCGC
GTACCCAGCGTGGTGGCAAACCGCAGCAATGTGTACAGCAACAATGCTGCGCAGGGTTCGCCTAACATGCA
AATGCGGAGTAGTGCTCCTATGCGATGGCGTGCTACTGAGGAGCATATTGGCAAATACAAACTCATAAAGA
CGATCGGCAAGGGCAATTTTGCCAAGGTGAAACTAGCGAAACACCTGCCCACTGGCAAGGAGGTCGCCATC
AAGATAATTGACAAGACCCAACTCAATCCTGGGTCACTACAGAAACTCTTTAGAGAGGTTAGAATAATGAA
GATGCTGGATCACCCCAACATAGTTAAATTGTTCCAAGTAATCGAAACGGAGAAGACGCTCTATCTGATCA
TGGAGTACGCATCTGGCGGAGAAGTCTTCGACTACCTGGTTCTCCACGGACGCATGAAGGAGAAGGAGGCG
CGAGTTAAGTTTCGACAAATCGTCTCAGCCGTGCAATATTGTCATCAAAAAGAATAATTCACAGGGACTT
AAAAGCTGAAAACCTTTTGCTGGACAGCGAACTGAACATCAAAATCGCTGACTTTGGCTTTTCGAACGAGT
TCACACCCGGCTCAAAGCTGGACACGTTCTGCGGTAGCCCGCCATATGCGGCACCGGAGCTGTTTCAGGGC
AAAAAGTACGACGGACCGGAGGTCGATGTTTGGTCGCTGGGCGTCATCCTGTATACGTTAGTGAGCGGTTC
CCTGCCCTTCGACGGCTCCACCTTGAGGGAGTTGCGTGAACGCGTGCTCAGAGGCAAATATAGAATTCCCT
TCTATATGTCGACTGACTGCGAAAACTTGCTCCGCAAATTCTTAGTACTGAATCCCGCAAAGCGTGCTAGT
CTGGAAACAATCATGGGCGACAAGTGGATGAACATGGGGTTTGAGGAGGACGAACTCAAGCCCTATATTGA
GCCCAAAGCCGATTTAGCCGATCCCAAGCGGATAGGTAAGACGGAAGCTCTAGTCGCGATGGGCTACAATC
GATCGGAGATCGAGGCTTCGCTCTCCCAGGTGCGCTACGACGATGTTTTCGCCACATATTTGCTGCTGGGT
CGCAAGAGTACAGACCCGGAAAGTGACGGATCGCGGTCTGGCTCCTCGCTCTCACTGCGCAACATCTCGGG
TAATGATGCGGGCGCCAATGCTGGTAGTGCGAGTGTTCAGAGTCCCACGCACAGAGGAGTCCACAGGAGCA
TATCGGCGTCTAGCACGAAGCCAAGTCGCCGAGCCTCGTCTGGTGTTGGACCGACAAATGCGGCAGCAACA
GTTGCGGCGGCCACGGGAGCCGTTGGTGCGGTTAATCCAAGCAATAACTACAATGCTGCAGGATCAGCGGC
GGATCGAGCATCAGTTGGCAGCAACTTTAAGCGACAGAACACAATCGACTCGGCTACGATTAAGGAGAACA
CAGCGCGACTGGCCGCTCAAAATCAGAGACCCGCTTCGGCCACACAAAAGATGCTCACCACGGCAGACACC
ACACTGAACAGTCCCGCCAAGCCGCGAACGGCAACGAAGTACGATCCGACGAATGGCAATCGCACGGTCAG
CGGCACAAGTGGCATCATTCCACGTCGCTCCACCACGCTTTATGAAAAGACTTCGTCGACGGAGAAAACCA
ACGTTATTCCTGCAGAGACAAAAATGGCATCGGCTGTTAAATCAAGCAGACACTTTCCAAGGAATGTTCCA
TCACGTTCAACCTTTCACTCTGGTCAAACCAGAGCACGAAACAACACAGCGCTGGAATACTCGGGCACCAG
CGGTGCCTCCGGCGACTCCTCCCATCCGGGTCGCATGAGCTTCTTCTCCAAACTCTCCTCACGTTTTAGCA
AACGGCCAAACCAGTAATTAACAAAACAAGCATTAACTACTTCTTGTTAATAGTTCTAAAACTGAAACTGA
AACAAACGATTCCCCTAGAGTAAACGCGCGTGACGGAGAGGTTCAGATATGAACAGACAGACACAGATATG
GTCGAATCCAATCGGATCGCTCGGATCGGATCAGATCGGGAAACGATACTGTTCACGTTGCCGTTGCCGAT
CCGAAATCGCTTTCGAATTCCATTTCGAGTTCAGATCCGTTTCCGGTTTCGATTCGAACCCCTTCAAATGA
ACACCGACAACGTTGAGTTCCATTGCGTTAATTGAAATTTCACAAATACGCCTATGTTTTATTACAATTAT
TAACTAATTATACATATAAATTTATATAAATTAAAGATACATATACATATATTTAAAAGTAAAGCAACCAC
AAACAGAAATTACGAAACCCTTTGTTTTCATTGTTTGTAAAACGATGCGAGGAGCGACCGCGACCATCAAA
AGGCAATACAAAATAAATATTGAATTATACAAATTAAAACCGAAACGAAACCGATACAAACAGAAATCCAC
TAAGAAACAAAGATATGATAAATGCAATGATCAGAAAGAATCCTGACTACCATTGCTGTCACTGTCACGAT
TATGGATTATATTAACTACTAAATATTACACCTACGAGTACTACCTAAACTACATATATATTTATGTTAAA
```

FIG. 10A

```
TGCGTATCGCAATTATAGTTATACAAACAAACAAATATCACTGATGAAGTGAACGTGAGATATAACTGCAA
AAAGTAAAATTAACTTAAGCCTAACTCAACTAAAACGATCTAAACTGAACTAAAGTGCGTGGTGTTTCGC
CCAAATCATTATTTTATAGTAGCCACAATAAAACACCAAAAGAAGTTGCTAATTTTGTAACGATGATCTTG
AATTTTATTTAGCGATCTTTGTATTTATATGTATGTGTATGTATGTATGGATCTGTATTTGTATTTCGATA
TGAGCTTGAATTAAATTGTATCCGTGGATCATACAATCAATCAATATCAATATCAACCAACCAACCAACCA
ACCAACCAACCAAGCAGCCAGCCAACAAACTAACGATCTTGCAATTCATAATCACCCAGAAGCCAGATGTG
CAGCGTATCTAGTAATTAAGCATACCACGTAGTCACTAAAAAACAATACAAAGCGATACATGAAAACCAAT
TTAACTTAAATTCAAGGAATAACAATGTATTACCACTAGTGCATGTGACCATTTTATTTGTACAGCTGATT
ATCTATAGATCGTGTTATCATCGGGCGCCTTCAGTGGCTCGATCAGTAGTTATCTATACATATTAAGTTTC
AAAGAAATAACGCATAATTAAAACAATTGATAATTTAATAAATCCATAATAAACGATGTGAAACATTTGCG
AGCAAAAGAAAAAAAAAAAAAAAAAAAAAAAAAA
```

FIG. 10B

```
TCTGGTCAAACCAGAGCACGAAACAACACAGCGCTGGAATACTCGGGCACCAGCGGTGCCTCCGGCGACT
CCTCCCATCCGGGTCGCATGAGCTTCTTCTCCAAACTCTCCTCACGTTTTAGCAAACGTCCCACAATCGC
AGACGAGGCGGCTAAGCCACGAGTTCTACGATTCACATGGTCAATGAAAACCACATCGCCCCTGATGCCC
GATCAGATAATGCAAAAGATCAGGGAGGTGCTGGACCAGAATAATTGCGACTACGAACAGCGGGAAAGAT
TCGTCCTGTGGTGCGTGCATGGAGATCCCAATACGGACTCACTGGTGCAATGGGAAATAGAAGTGTGCAA
GCTGCCACGACTCTCTCTGAATGGAGTGCGCTTCAAGCGAATTTCCGGCACCAGGATTGGCTTCAAGAAC
ATTGCGTCGCGCATTGCTTTTGACCTCAAGCTGTGACTTAACCAAACGAACAACGA
```

FIG. 11

SEQUENCE LISTING

<160> NUMBER OF SEQ ID NOS: 14

<210> SEQ ID NO 1
<211> LENGTH: 3857
<212> TYPE: DNA
<213> ORGANISM: Homo sapiens

<400> SEQUENCE: 1

```
agagaccgag acgtacatac ttttgttgct gccaaagtgg atgtggacgg aggaaaatag     60
taatatttaa ctgcgttgcg ggagcgggac aatcgtcgtt tgccaattgc ggccaccgct    120
tatgtcggct aatcggctat caataatatt agtaatcgta tcaatatcaa gttacccatt    180
acccatcgcg gatacacatt agttttgcga agggcagagc agcgcagagc atatagcgaa    240
tatttccatt tgttgccaac aagactgtcg ttgttgttgt tattattgtg gcttttcagt    300
gactggggag agcagtgggg gtgcgttcgt aatccttgtg aaaaatcggt gaccgttctt    360
cttaaaaaaa aagcgaaaga aaaaaccatc gcgataagaa aatataagaa agaaaaatct    420
gattgaaaac caaagagctg ctgctactgc tgctgtgcga gtgagagcgg tcgagaggta    480
gctagtgagc gagtgagaaa gctatgtatt gcatttgcat ttcgttgtgt gtgtcgtcgt    540
tttcgttcgg taaagtcgg taaaaagcag agcctttcca aacctaacca ctttcgggta    600
aacggaatcg gaaaggaac tgggaaaatc gaaagaaatt aaataataat atgcgttaca    660
tcgatggcaa caacaacaac aacagcagcg ccatcagct agcgactcct ctctgagcga    720
gagagctaat agcttttcag ctttagcttt tcttgggcca atcggaaatt gtatttcatt    780
gatgtgaagg agtaccacgg atgatagaaa cccattgggc atttgactac ttttaagcac    840
cgaaacctga aagactcccg aaaatactcg aatctcacgt gcagaatctc taagaatccc    900
tattggactg tttaaaaata tgtcgacagc aatgcgcacc acactgcagt cagttcctga    960
ggccctgcca gcggatagcg tgtccaatgg cacagcatcc aatgtagcag caccggcggc   1020
gccagtatcg agcgcaacaa acgcggtgcc accactggcc gccgtctcca gcacaaccgc   1080
cacctacgcc accaactcga tcagcacatc ctcgcattcg gtcaaggatc agcagcagca   1140
acagcagcag cagcagcatg attcggccaa tgcaaacatt tgtgtcactgc caccaacgac   1200 aacgccagtc gccaacacta acacaatgat gcccattgta acgtcctcga attcggccac   1260
cagcaatagc actgcggcca cgcccacgcc ggcctcgggg gcggcagcga caggtggagt   1320
gggatcagtt tcccagggtc cagcgaccgt ttcggcgtca gcggccaaca ccaatcactc   1380
gcaccagcac agccaccaac accaccacca tgtggccaac aacatgacca ccgacggtgc   1440
ccgcttgtcc agcaacaatt cggcggtggt ggcgagctca gcgattaacc accaccatca   1500
ccacaccccc ggcagtggag tggcgcccac cgtcaacaag aacgtgctta gcacccactc   1560
ggctcatccc tccgcgatca agcaacgaac ctcgtccgcc aagggttcgc ctaacatgca   1620
aatgcggagt agtgctccta tgcgatggcg tgctactgag gagcatattg gcaaatacaa   1680
actcataaag acgatcggca agggcaattt tgccaaggtg aaactagcga aacacctgcc   1740
cactggcaag gaggtcgcca tcaagataat tgacaagacc caactcaatc ctgggtcact   1800
acagaaactc tttagagagg ttagaataat gaagatgctg gatcacccca acatagttaa   1860
attgttccaa gtaatcgaaa cggagaagac gctctatctg atcatggagt acgcatctgg   1920
cggagaagtc ttcgactacc tggttctcca cggacgcatg aaggagaagg aggcgcgagt   1980
taagtttcga caaatcgtct cagccgtgca atattgtcat caaaaagaa taattcacag   2040
```

-continued

```
ggacttaaaa gctgaaaacc ttttgctgga cagcgaactg aacatcaaaa tcgctgactt      2100
tggcttttcg aacgagttca cacccggctc aaagctggac acgttctgcg gtagcccgcc      2160
atatgcggca ccggagctgt tcagggcaaa aagtacgac ggaccggagg tcgatgtttg       2220
gtcgctgggc gtcatcctgt atacgttagt gagcggttcc ctgcccttcg acggctccac     2280
cttgagggag ttgcgtgaac gcgtgctcag aggcaaatat agaattccct tctatatgtc     2340
gactgactgc gaaaacttgc tccgcaaatt cttagtactg aatcccgcaa agcgtgctag     2400
tctggaaaca atcatgggcg acaagtggat gaacatgggg tttgaggagg acgaactcaa     2460
gccctatatt gagcccaaag ccgatttagc cgatcccaag cggatagaag ctctagtcgc     2520
gatgggctac aatcgatcgg agatcgaggc ttcgctctcc caggtgcgct acgacgatgt     2580
tttcgccaca tatttgctgc tgggtcgcaa gagtacagac ccggaaagtg acggatcgcg     2640
gtctggctcc tcgctctcac tgcgcaacat ctcgggtaat gatgcgggcg ccaatgctgg     2700
tagtgcgagt gttcagagtc ccacgcacag aggagtccac aggagcatat cggcgtctag     2760
cacgaagcca agtcgccgag cctcgtctgg tgcggaaact ttgcgtgttg gaccgacaaa     2820
tgcggcagca acagttgcgg cggccacggg agccgttggt gcggttaatc caagcaataa     2880
ctacaatgct gcaggatcag cggcggatcg agcatcagtt ggcagcaact ttaagcgaca     2940
gaacacaatc gactcggcta cgattaagga gaacacagcg cgactggccg ctcaaaatca     3000
gagacccgct tcggccacac aaaagatgct caccacggca gacaccacac tgaacagtcc     3060
cgccaagccg cgaacggcaa cgaagtacga tccgacgaat ggcaatcgca cggtcagcgg     3120
cacaagtggc atcattccac gtcgctccac cacgctttat gaaaagactt cgtcgacgga     3180
gaaaaccaac gttattcctg cagagacaaa aatggcatcg gctgttaaat caagcagaca     3240
ctttccaagg aatgttccat cacgttcaac ctttcactct ggtcaaacca gagcacgaaa     3300
caacacagcg ctggaatact cgggcaccag cggtgcctcc ggcgactcct cccatccggg     3360
tcgcatgagc ttcttctcca aactctcctc acgttttagc aaacggccaa accagtaatt     3420
aacaaaacaa gcattaacta cttccttgtta atagttctaa aactgaaact gaaacaaacg     3480
attcccctag agtaaacgcg cgtgacggag aggttcagat atgaacagac agacacagat     3540
atggtcgaat ccaatcggat cgctcggatc ggatcagatc gggaaacgat actgttcacg     3600
ttgccgttgc cgatccgaaa tcgctttcga attccatttc gagttcagat ccgtttccgg     3660
tttcgattcg aaccccttca aatgaacacc gacaacgttg agttccattg cgttaattga     3720
aatttcacaa atacgcctat gttttattac aattattaac taattataca tataaattta     3780
tataaattaa agatacatat acatatattt aaaagtaaag caaccacaaa cagaaattaa     3840
aaaaaaaaaa aaaaaaa                                                    3857
```

<210> SEQ ID NO 2
<211> LENGTH: 832
<212> TYPE: PRT
<213> ORGANISM: Homo sapiens

<400> SEQUENCE: 2

Met Ser Thr Ala Met Arg Thr Thr Leu Gln Ser Val Pro Glu Ala Leu
1               5                   10                  15

Pro Ala Asp Ser Val Ser Asn Gly Thr Ala Ser Asn Val Ala Ala Pro
            20                  25                  30

Ala Ala Pro Val Ser Ser Ala Thr Asn Ala Val Pro Pro Leu Ala Ala
        35                  40                  45

-continued

Val Ser Ser Thr Thr Ala Thr Tyr Ala Thr Asn Ser Ile Ser Thr Ser
    50              55                  60

Ser His Ser Val Lys Asp Gln Gln Gln Gln Gln Gln Gln Gln His
65              70                  75                  80

Asp Ser Ala Asn Ala Asn Ile Val Ser Leu Pro Pro Thr Thr Thr Pro
                85                  90                  95

Val Ala Asn Thr Asn Thr Met Met Pro Ile Val Thr Ser Ser Asn Ser
            100                 105                 110

Ala Thr Ser Asn Ser Thr Ala Ala Thr Pro Thr Pro Ala Ser Gly Ala
        115                 120                 125

Ala Ala Thr Gly Gly Val Gly Ser Val Ser Gln Gly Pro Ala Thr Val
    130                 135                 140

Ser Ala Ser Ala Ala Asn Thr Asn His Ser His Gln His Ser His Gln
145                 150                 155                 160

His His His His Val Ala Asn Asn Met Thr Thr Asp Gly Ala Arg Leu
                165                 170                 175

Ser Ser Asn Asn Ser Ala Val Val Ala Ser Ser Ala Ile Asn His His
            180                 185                 190

His His His Thr Pro Gly Ser Gly Val Ala Pro Thr Val Asn Lys Asn
        195                 200                 205

Val Leu Ser Thr His Ser Ala His Pro Ser Ala Ile Lys Gln Arg Thr
    210                 215                 220

Ser Ser Ala Lys Gly Ser Pro Asn Met Gln Met Arg Ser Ser Ala Pro
225                 230                 235                 240

Met Arg Trp Arg Ala Thr Glu Glu His Ile Gly Lys Tyr Lys Leu Ile
                245                 250                 255

Lys Thr Ile Gly Lys Gly Asn Phe Ala Lys Val Lys Leu Ala Lys His
            260                 265                 270

Leu Pro Thr Gly Lys Glu Val Ala Ile Lys Ile Ile Asp Lys Thr Gln
        275                 280                 285

Leu Asn Pro Gly Ser Leu Gln Lys Leu Phe Arg Glu Val Arg Ile Met
    290                 295                 300

Lys Met Leu Asp His Pro Asn Ile Val Lys Leu Phe Gln Val Ile Glu
305                 310                 315                 320

Thr Glu Lys Thr Leu Tyr Leu Ile Met Glu Tyr Ala Ser Gly Gly Glu
                325                 330                 335

Val Phe Asp Tyr Leu Val Leu His Gly Arg Met Lys Glu Lys Glu Ala
            340                 345                 350

Arg Val Lys Phe Arg Gln Ile Val Ser Ala Val Gln Tyr Cys His Gln
        355                 360                 365

Lys Arg Ile Ile His Arg Asp Leu Lys Ala Glu Asn Leu Leu Leu Asp
    370                 375                 380

Ser Glu Leu Asn Ile Lys Ile Ala Asp Phe Gly Phe Ser Asn Glu Phe
385                 390                 395                 400

Thr Pro Gly Ser Lys Leu Asp Thr Phe Cys Gly Ser Pro Pro Tyr Ala
                405                 410                 415

Ala Pro Glu Leu Phe Gln Gly Lys Lys Tyr Asp Gly Pro Glu Val Asp
            420                 425                 430

Val Trp Ser Leu Gly Val Ile Leu Tyr Thr Leu Val Ser Gly Ser Leu
        435                 440                 445

Pro Phe Asp Gly Ser Thr Leu Arg Glu Leu Arg Glu Arg Val Leu Arg
    450                 455                 460

-continued

```
Gly Lys Tyr Arg Ile Pro Phe Tyr Met Ser Thr Asp Cys Glu Asn Leu
465                 470                 475                 480

Leu Arg Lys Phe Leu Val Leu Asn Pro Ala Lys Arg Ala Ser Leu Glu
            485                 490                 495

Thr Ile Met Gly Asp Lys Trp Met Asn Met Gly Phe Glu Glu Asp Glu
        500                 505                 510

Leu Lys Pro Tyr Ile Glu Pro Lys Ala Asp Leu Ala Asp Pro Lys Arg
    515                 520                 525

Ile Glu Ala Leu Val Ala Met Gly Tyr Asn Arg Ser Glu Ile Glu Ala
530                 535                 540

Ser Leu Ser Gln Val Arg Tyr Asp Asp Val Phe Ala Thr Tyr Leu Leu
545                 550                 555                 560

Leu Gly Arg Lys Ser Thr Asp Pro Glu Ser Asp Gly Ser Arg Ser Gly
            565                 570                 575

Ser Ser Leu Ser Leu Arg Asn Ile Ser Gly Asn Asp Ala Gly Ala Asn
        580                 585                 590

Ala Gly Ser Ala Ser Val Gln Ser Pro Thr His Arg Gly Val His Arg
    595                 600                 605

Ser Ile Ser Ala Ser Ser Thr Lys Pro Ser Arg Arg Ala Ser Ser Gly
610                 615                 620

Ala Glu Thr Leu Arg Val Gly Pro Thr Asn Ala Ala Thr Val Ala
625                 630                 635                 640

Ala Ala Thr Gly Ala Val Gly Ala Val Asn Pro Ser Asn Asn Tyr Asn
            645                 650                 655

Ala Ala Gly Ser Ala Ala Asp Arg Ala Ser Val Gly Ser Asn Phe Lys
        660                 665                 670

Arg Gln Asn Thr Ile Asp Ser Ala Thr Ile Lys Glu Asn Thr Ala Arg
    675                 680                 685

Leu Ala Ala Gln Asn Gln Arg Pro Ala Ser Ala Thr Gln Lys Met Leu
690                 695                 700

Thr Thr Ala Asp Thr Thr Leu Asn Ser Pro Ala Lys Pro Arg Thr Ala
705                 710                 715                 720

Thr Lys Tyr Asp Pro Thr Asn Gly Asn Arg Thr Val Ser Gly Thr Ser
            725                 730                 735

Gly Ile Ile Pro Arg Arg Ser Thr Thr Leu Tyr Glu Lys Thr Ser Ser
        740                 745                 750

Thr Glu Lys Thr Asn Val Ile Pro Ala Glu Thr Lys Met Ala Ser Ala
    755                 760                 765

Val Lys Ser Ser Arg His Phe Pro Arg Asn Val Pro Ser Arg Ser Thr
770                 775                 780

Phe His Ser Gly Gln Thr Arg Ala Arg Asn Asn Thr Ala Leu Glu Tyr
785                 790                 795                 800

Ser Gly Thr Ser Gly Ala Ser Gly Asp Ser Ser His Pro Gly Arg Met
            805                 810                 815

Ser Phe Phe Ser Lys Leu Ser Ser Arg Phe Ser Lys Arg Pro Asn Gln
        820                 825                 830
```

<210> SEQ ID NO 3
<211> LENGTH: 4790
<212> TYPE: DNA
<213> ORGANISM: Homo sapiens

<400> SEQUENCE: 3
agaacaataa acacgccaag cgcaacttga aaagaaata agaaaaaaga aaagttgcg    60

-continued

| | | |
|---|---|---|
| atctctccga gcaacaagta cttgtgcacc aacacactca agggaagagt gccacgacaa | 120 |
| aaaaatttaa gagaaaaaaa acagaaaaac cgaaatcagc agcaaaacgg aggagctatg | 180 |
| gaggccacca ctaccacaac acctgacttg aatcgcggcg atgccaccag gaagagtgtc | 240 |
| cggctgtatg ccgcccgcaa gggggcggca cctgcgccgc ccaagctcag tgtggcgcca | 300 |
| tctagtaacc agaacagcaa ccacagcagc aacaacaaca atagcagcag taacttgccg | 360 |
| gaaacggaaa aggaaatgga actgcgtcaa acacatcttg ccaacaagga tctcgatgga | 420 |
| gccaccgaag acgacagcat agtggagctt cgacgacgtg atgcccaagc cactccattg | 480 |
| cccaggatag ccgtatcggc tctacccacc ctacagccgc atcccacgcc aaagaacgc | 540 |
| caaaagccgc caatgccacg ccttctgtcc accgaagacg atgccggtgt gtcctttgcc | 600 |
| ctcggctcca tcgagaagca catccataac gtggaggaga gctttaagca acagcagcaa | 660 |
| aaccaacaat cccaatcatc gatggacgtg atgaaactgg agatcaagcg caagcagagc | 720 |
| aagcgctacg tgaaacgga aaaccttctg cgaccgggca ttagtgacat gtcctccgag | 780 |
| aatgattttc agtatttggg cggcaggcgg gcaggagaac tggatgacag caatgagctg | 840 |
| atgttatcgg aattccagcg cggcagcgat ggtcgtaact cgatcggagc ctattccaag | 900 |
| aactcggctg ctgccgcaaa cggagcaaat gctgtgaagg ctaaactggc acgtactgcc | 960 |
| tccgatacga agaataatga tacgcgtgctg gccatgaggg ccacttttaa gcagaagcag | 1020 |
| cacttgcagg acgagaaaca gccagcggta tggcgaccag ctggcactgg acccactccg | 1080 |
| gcggccagga gctcctcctc caccacgtcc acctccggct cggccagtcg tggcggtagc | 1140 |
| agcagcagcg tggtggatgg agtggctcca tctaagctta cggccactac catttcagcg | 1200 |
| tctaagcggc gtgaggagaa tttgcgacaa tttgaagctt tgttggccca aaaatcctca | 1260 |
| catcgtcatg gagcatctgg tgcctcggga acaggaagta atgcagccag ttcgaaaaga | 1320 |
| cgttcggacc ggccgattgt ggctcctatt cctccgtaca attccagtcg agcagagcat | 1380 |
| gtgaccagct cgaccagaca cagcgttgat ccaagatccc attcgggaca cgagtcgagg | 1440 |
| tcaggaacag cctcaactca cccgcctgta ggacatcatc ccactagccg cgtacccagc | 1500 |
| gtggtggcaa accgcagcaa tgtgtacagc aacaatgctg cgcagggttc gcctaacatg | 1560 |
| caaatgcgga gtagtgctcc tatgcgatgg cgtgctactg aggagcatat tggcaaatac | 1620 |
| aaactcataa agacgatcgg caagggcaat tttgccaagg tgaaactagc gaaacacctg | 1680 |
| cccactggca aggaggtcgc catcaagata attgacaaga cccaactcaa tcctgggtca | 1740 |
| ctacagaaac tctttagaga ggttagaata atgaagatgc tggatcaccc caacatagtt | 1800 |
| aaattgttcc aagtaatcga aacgagaag acgctctatc tgatcatgga gtacgcatct | 1860 |
| ggcggagaag tcttcgacta cctggttctc cacggacgca tgaaggagaa ggaggcgcga | 1920 |
| gttaagtttc gacaaatcgt ctcagccgtg caatattgtc atcaaaaaag aataattcac | 1980 |
| agggacttaa aagctgaaaa ccttttgctg gacagcgaac tgaacatcaa aatcgctgac | 2040 |
| tttggctttt cgaacgagtt cacacccggc tcaaagctgg acacgttctg cggtagcccg | 2100 |
| ccatatgcgg caccggagct gtttcagggc aaaaagtacg acggaccgga ggtcgatgtt | 2160 |
| tggtcgctgg gcgtcatcct gtatacgtta gtgagcggtt ccctgccctt cgacggctcc | 2220 |
| accttgaggg agttgcgtga acgcgtgctc agaggcaaat atagaattcc cttctatatg | 2280 |
| tcgactgact gcgaaaactt gctccgcaaa ttcttagtac tgaatcccgc aaagcgtgct | 2340 |
| agtctgaaaa caatcatggg cgacaagtgg atgaacatgg ggtttgagga ggacgaactc | 2400 |
| aagccctata ttgagcccaa agccgattta gccgatccca gcggataggg taagacggaa | 2460 |

```
gctctagtcg cgatgggcta caatcgatcg gagatcgagg cttcgctctc ccaggtgcgc      2520
tacgacgatg ttttcgccac atatttgctg ctgggtcgca agagtacaga cccggaaagt      2580
gacggatcgc ggtctggctc ctcgctctca ctgcgcaaca tctcgggtaa tgatgcgggc      2640
gccaatgctg gtagtgcgag tgttcagagt cccacgcaca gaggagtcca caggagcata      2700
tcggcgtcta gcacgaagcc aagtcgccga gcctcgtctg gtgttggacc gacaaatgcg      2760
gcagcaacag ttgcggcggc cacgggagcc gttggtgcgg ttaatccaag caataactac      2820
aatgctgcag gatcagcggc ggatcgagca tcagttggca gcaactttaa gcgacagaac      2880
acaatcgact cggctacgat taaggagaac acagcgcgac tggccgctca aaatcagaga      2940
cccgcttcgg ccacacaaaa gatgctcacc acggcagaca ccacactgaa cagtcccgcc      3000
aagccgcgaa cggcaacgaa gtacgatccg acgaatggca atcgcacggt cagcggcaca      3060
agtggcatca ttccacgtcg ctccaccacg ctttatgaaa agacttcgtc gacggagaaa      3120
accaacgtta ttcctgcaga gacaaaaatg gcatcggctg ttaaatcaag cagacacttt      3180
ccaaggaatg ttccatcacg ttcaaccttt cactctggtc aaaccagagc acgaaacaac      3240
acagcgctgg aatactcggg caccagcggt gcctccggcg actcctccca tccgggtcgc      3300
atgagcttct tctccaaact ctcctcacgt tttagcaaac ggccaaacca gtaattaaca      3360
aaacaagcat taactacttc ttgttaatag ttctaaaact gaaactgaaa caaacgattc      3420
ccctagagta aacgcgcgtg acggagaggt tcagatatga acagacagac acagatatgg      3480
tcgaatccaa tcggatcgct cggatcggat cagatcggga aacgatactg ttcacgttgc      3540
cgttgccgat ccgaaatcgc tttcgaattc catttcgagt tcagatccgt ttccggtttc      3600
gattcgaacc ccttcaaatg aacaccgaca acgttgagtt ccattgcgtt aattgaaatt      3660
tcacaaatac gcctatgttt tattacaatt attaactaat tatacatata aatttatata      3720
aattaaagat acatatacat atatttaaaa gtaaagcaac cacaaacaga aattacgaaa      3780 cccttttgttt tcattgtttg taaaacgatg cgaggagcga ccgcgaccat caaaaggcaa      3840
tacaaaataa atattgaatt atacaaatta aaaccgaaac gaaaccgata caaacagaaa      3900
tccactaaga aacaaagata tgataaatgc aatgatcaga agaatcctg actaccattg      3960 ctgtcactgt cacgattatg gattatatta actactaaat attacaccta cgagtactac      4020
ctaaactaca tatatattta tgttaaatgc gtatcgcaat tatagttata caaacaaaca      4080
aatatcactg atgaagtgaa cgtgagatat aactgcaaaa agtaaaatta acttaagcct      4140
aactcaacta aaacgatcta aactgaacta aagtgcgtgg tgttttcgcc caaatcatta      4200
ttttatagta gccacaataa aacaccaaaa gaagttgcta atttttgtaac gatgatcttg      4260 aatttttattt agcgatcttt gtattttatat gtatgtgtat gtatgtatgg atctgtatttt      4320 gtatttcgat atgagcttga attaaattgt atccgtggat catacaatca atcaatatca      4380
atatcaacca accaaccaac caaccaacca accaagcagc cagccaacaa actaacgatc      4440
ttgcaattca taatcaccca gaagccagat gtgcagcgta tctagtaatt aagcatacca      4500
cgtagtcact aaaaaacaat acaaagcgat acatgaaaac caattaact taaattcaag      4560 gaataacaat gtattaccac tagtgcatgt gaccatttta tttgtacagc tgattatcta      4620
tagatcgtgt tatcatcggg cgccttcagt ggctcgatca gtagttatct atacatatta      4680
agtttcaaag aaataacgca taattaaaac aattgataat ttaataaatc cataataaac      4740
gatgtgaaac atttgcgagc aaaagaaaaa aaaaaaaaaa aaaaaaaaa                 4790
```

```
<210> SEQ ID NO 4
<211> LENGTH: 1058
<212> TYPE: PRT
<213> ORGANISM: Homo sapiens

<400> SEQUENCE: 4

Met Glu Ala Thr Thr Thr Thr Pro Asp Leu Asn Arg Gly Asp Ala
1               5                   10                  15

Thr Arg Lys Ser Val Arg Leu Tyr Ala Ala Arg Lys Gly Ala Ala Pro
                20                  25                  30

Ala Pro Pro Lys Leu Ser Val Ala Pro Ser Ser Asn Gln Asn Ser Asn
                35                  40                  45

His Ser Ser Asn Asn Asn Ser Ser Ser Asn Leu Pro Glu Thr Glu
    50                  55                  60

Lys Glu Met Glu Leu Arg Gln Thr His Leu Ala Asn Lys Asp Leu Asp
65              70                  75                  80

Gly Ala Thr Glu Asp Asp Ser Ile Val Glu Leu Arg Arg Arg Asp Ala
                85                  90                  95

Gln Ala Thr Pro Leu Pro Arg Ile Ala Val Ser Ala Leu Pro Thr Leu
                100                 105                 110

Gln Pro His Pro Thr Pro Lys Glu Arg Gln Lys Pro Pro Met Pro Arg
                115                 120                 125

Leu Leu Ser Thr Glu Asp Asp Ala Gly Val Ser Phe Ala Leu Gly Ser
    130                 135                 140

Ile Glu Lys His Ile His Asn Val Glu Glu Ser Phe Lys Gln Gln Gln
145                 150                 155                 160

Gln Asn Gln Gln Ser Gln Ser Ser Met Asp Val Met Lys Leu Glu Ile
                165                 170                 175

Lys Arg Lys Gln Ser Lys Arg Tyr Gly Glu Thr Glu Asn Leu Leu Arg
                180                 185                 190

Pro Gly Ile Ser Asp Met Ser Ser Glu Asn Asp Phe Gln Tyr Leu Gly
                195                 200                 205

Gly Arg Arg Ala Gly Glu Leu Asp Asp Ser Asn Glu Leu Met Leu Ser
    210                 215                 220

Glu Phe Gln Arg Gly Ser Asp Gly Arg Asn Ser Ile Gly Ala Tyr Ser
225                 230                 235                 240

Lys Asn Ser Ala Ala Ala Asn Gly Ala Asn Ala Val Lys Ala Lys
                245                 250                 255

Leu Ala Arg Thr Ala Ser Asp Thr Lys Asn Asn Asp Thr Val Leu Ala
                260                 265                 270

Met Arg Ala Thr Phe Lys Gln Lys Gln His Leu Gln Asp Glu Lys Gln
                275                 280                 285

Pro Ala Val Trp Arg Pro Ala Gly Thr Gly Pro Thr Pro Ala Ala Arg
    290                 295                 300

Ser Ser Ser Ser Thr Thr Ser Thr Ser Gly Ser Ala Ser Arg Gly Gly
305                 310                 315                 320

Ser Ser Ser Ser Val Val Asp Gly Val Ala Pro Ser Lys Leu Thr Ala
                325                 330                 335

Thr Thr Ile Ser Ala Ser Lys Arg Arg Glu Glu Asn Leu Arg Gln Phe
                340                 345                 350

Glu Ala Leu Leu Ala Gln Lys Ser Ser His Arg His Gly Ala Ser Gly
                355                 360                 365

Ala Ser Gly Thr Gly Ser Asn Ala Ala Ser Ser Lys Arg Arg Ser Asp
    370                 375                 380
```

-continued

```
Arg Pro Ile Val Ala Pro Ile Pro Pro Tyr Asn Ser Ser Arg Ala Glu
385                 390                 395                 400

His Val Thr Ser Ser Thr Arg His Ser Val Asp Pro Arg Ser His Ser
            405                 410                 415

Gly His Glu Ser Arg Ser Gly Thr Ala Ser Thr His Pro Pro Val Gly
            420                 425                 430

His His Pro Thr Ser Arg Val Pro Ser Val Val Ala Asn Arg Ser Asn
            435                 440                 445

Val Tyr Ser Asn Asn Ala Ala Gln Gly Ser Pro Asn Met Gln Met Arg
        450                 455                 460

Ser Ser Ala Pro Met Arg Trp Arg Ala Thr Glu Glu His Ile Gly Lys
465                 470                 475                 480

Tyr Lys Leu Ile Lys Thr Ile Gly Lys Gly Asn Phe Ala Lys Val Lys
                485                 490                 495

Leu Ala Lys His Leu Pro Thr Gly Lys Glu Val Ala Ile Lys Ile Ile
            500                 505                 510

Asp Lys Thr Gln Leu Asn Pro Gly Ser Leu Gln Lys Leu Phe Arg Glu
        515                 520                 525

Val Arg Ile Met Lys Met Leu Asp His Pro Asn Ile Val Lys Leu Phe
530                 535                 540

Gln Val Ile Glu Thr Glu Lys Thr Leu Tyr Leu Ile Met Glu Tyr Ala
545                 550                 555                 560

Ser Gly Gly Glu Val Phe Asp Tyr Leu Val Leu His Gly Arg Met Lys
                565                 570                 575

Glu Lys Glu Ala Arg Val Lys Phe Arg Gln Ile Val Ser Ala Val Gln
            580                 585                 590

Tyr Cys His Gln Lys Arg Ile Ile His Arg Asp Leu Lys Ala Glu Asn
        595                 600                 605

Leu Leu Leu Asp Ser Glu Leu Asn Ile Lys Ile Ala Asp Phe Gly Phe
    610                 615                 620

Ser Asn Glu Phe Thr Pro Gly Ser Lys Leu Asp Thr Phe Cys Gly Ser
625                 630                 635                 640

Pro Pro Tyr Ala Ala Pro Glu Leu Phe Gln Gly Lys Lys Tyr Asp Gly
                645                 650                 655

Pro Glu Val Asp Val Trp Ser Leu Gly Val Ile Leu Tyr Thr Leu Val
            660                 665                 670

Ser Gly Ser Leu Pro Phe Asp Gly Ser Thr Leu Arg Glu Leu Arg Glu
        675                 680                 685

Arg Val Leu Arg Gly Lys Tyr Arg Ile Pro Phe Tyr Met Ser Thr Asp
690                 695                 700

Cys Glu Asn Leu Leu Arg Lys Phe Leu Val Leu Asn Pro Ala Lys Arg
705                 710                 715                 720

Ala Ser Leu Glu Thr Ile Met Gly Asp Lys Trp Met Asn Met Gly Phe
                725                 730                 735

Glu Glu Asp Glu Leu Lys Pro Tyr Ile Glu Pro Lys Ala Asp Leu Ala
            740                 745                 750

Asp Pro Lys Arg Ile Gly Lys Thr Glu Ala Leu Val Ala Met Gly Tyr
        755                 760                 765

Asn Arg Ser Glu Ile Glu Ala Ser Leu Ser Gln Val Arg Tyr Asp Asp
    770                 775                 780

Val Phe Ala Thr Tyr Leu Leu Leu Gly Arg Lys Ser Thr Asp Pro Glu
785                 790                 795                 800
```

-continued

```
Ser Asp Gly Ser Arg Ser Gly Ser Ser Leu Ser Leu Arg Asn Ile Ser
                805                 810                 815
Gly Asn Asp Ala Gly Ala Asn Ala Gly Ser Ala Ser Val Gln Ser Pro
            820                 825                 830
Thr His Arg Gly Val His Arg Ser Ile Ser Ala Ser Ser Thr Lys Pro
        835                 840                 845
Ser Arg Arg Ala Ser Ser Gly Val Gly Pro Thr Asn Ala Ala Ala Thr
    850                 855                 860
Val Ala Ala Ala Thr Gly Ala Val Gly Ala Val Asn Pro Ser Asn Asn
865                 870                 875                 880
Tyr Asn Ala Ala Gly Ser Ala Ala Asp Arg Ala Ser Val Gly Ser Asn
                885                 890                 895
Phe Lys Arg Gln Asn Thr Ile Asp Ser Ala Thr Ile Lys Glu Asn Thr
            900                 905                 910
Ala Arg Leu Ala Ala Gln Asn Gln Arg Pro Ala Ser Ala Thr Gln Lys
        915                 920                 925
Met Leu Thr Thr Ala Asp Thr Thr Leu Asn Ser Pro Ala Lys Pro Arg
    930                 935                 940
Thr Ala Thr Lys Tyr Asp Pro Thr Asn Gly Asn Arg Thr Val Ser Gly
945                 950                 955                 960
Thr Ser Gly Ile Ile Pro Arg Arg Ser Thr Thr Leu Tyr Glu Lys Thr
                965                 970                 975
Ser Ser Thr Glu Lys Thr Asn Val Ile Pro Ala Glu Thr Lys Met Ala
            980                 985                 990
Ser Ala Val Lys Ser Ser Arg His Phe Pro Arg Asn Val Pro Ser Arg
        995                 1000                1005
Ser Thr Phe His Ser Gly Gln Thr Arg Ala Arg Asn Asn Thr Ala Leu
    1010                1015                1020
Glu Tyr Ser Gly Thr Ser Gly Ala Ser Gly Asp Ser Ser His Pro Gly
1025                1030                1035                1040
Arg Met Ser Phe Phe Ser Lys Leu Ser Ser Arg Phe Ser Lys Arg Pro
                1045                1050                1055
Asn Gln

<210> SEQ ID NO 5
<211> LENGTH: 36
<212> TYPE: PRT
<213> ORGANISM: Homo sapiens

<400> SEQUENCE: 5

Gln Arg Leu Gln Val Arg Lys Lys Pro Gln Arg Arg Lys Lys Arg Ala
1               5                   10                  15
Pro Ser Met Ser Arg Thr Ser Ser Tyr Ser Ser Ile Thr Asp Ser Thr
                20                  25                  30
Met Ser Leu Asn
        35

<210> SEQ ID NO 6
<211> LENGTH: 36
<212> TYPE: PRT
<213> ORGANISM: Homo sapiens

<400> SEQUENCE: 6

Ala Ser Arg Leu Leu Lys Arg His Arg Arg Arg Lys Gln Arg Pro
1               5                   10                  15
Pro Arg Leu Glu Arg Thr Ser Ser Phe Ser Ser Val Thr Asp Ser Thr
```

```
            20                  25                  30

Met Ser Leu Asn
        35

<210> SEQ ID NO 7
<211> LENGTH: 36
<212> TYPE: PRT
<213> ORGANISM: Homo sapiens

<400> SEQUENCE: 7

Ala Ser Arg Leu Leu Lys Arg His Arg Arg Arg Lys Gln Arg Pro
 1               5                  10                  15

Pro Arg Met Glu Arg Thr Ser Ser Phe Ser Ser Val Thr Asp Ser Thr
            20                  25                  30

Met Ser Leu Asn
        35

<210> SEQ ID NO 8
<211> LENGTH: 36
<212> TYPE: PRT
<213> ORGANISM: Homo sapiens

<400> SEQUENCE: 8

Ser Arg Leu Met Arg Arg His Lys Arg Arg Arg Lys Gln Lys Val
 1               5                  10                  15

Ser Arg Ile Glu Arg Ser Ser Ser Phe Ser Ser Ile Thr Asp Ser Thr
            20                  25                  30

Met Ser Leu Asn
        35

<210> SEQ ID NO 9
<211> LENGTH: 36
<212> TYPE: PRT
<213> ORGANISM: Homo sapiens

<400> SEQUENCE: 9

Ser Arg Leu Val Arg Lys His Lys Cys Arg Arg Lys Gln Arg Leu
 1               5                  10                  15

Arg Gln Thr Asp Arg Ala Ser Ser Phe Ser Ser Ile Thr Asp Ser Thr
            20                  25                  30

Met Ser Leu Asn
        35

<210> SEQ ID NO 10
<211> LENGTH: 56
<212> TYPE: DNA
<213> ORGANISM: Artificial Sequence
<220> FEATURE:
<221> NAME/KEY: modified_base
<222> LOCATION: 9, 12, 15, 18, 39, 42, 45, 48, 51
<223> OTHER INFORMATION: n=inosine
<221> NAME/KEY: misc_feature
<222> LOCATION: (1)...(56)
<223> OTHER INFORMATION: n = A,T,C or G
<220> FEATURE:
<223> OTHER INFORMATION: synthetic probe

<400> SEQUENCE: 10
gagaayacng cnmgnytngc cgctcaaaat cagagaccng cntcngcnac ncagaa      56

<210> SEQ ID NO 11
<211> LENGTH: 33
<212> TYPE: DNA
```

```
<213> ORGANISM: Artificial Sequence
<220> FEATURE:
<221> NAME/KEY: modified_base
<222> LOCATION: 3, 11, 13, 18, 20, 22, 24
<223> OTHER INFORMATION: n=inosine
<221> NAME/KEY: misc_feature
<222> LOCATION: (1)...(33)
<223> OTHER INFORMATION: n = A,T,C or G
<220> FEATURE:
<223> OTHER INFORMATION: synthetic probe

<400> SEQUENCE: 11
cgncaraaya cnatngayts ngcnacnatn aag                                33

<210> SEQ ID NO 12
<211> LENGTH: 623
<212> TYPE: PRT
<213> ORGANISM: Homo sapiens

<400> SEQUENCE: 12
```

| Met | Asp | Ala | Asp | Arg | Gly | Gly | Gly | Gln | Glu | Thr | Lys | Val | Ile | Tyr | His |
|---|---|---|---|---|---|---|---|---|---|---|---|---|---|---|---|
| 1 | | | | 5 | | | | | 10 | | | | | 15 | |

| Ile | Asp | Asp | Glu | Thr | Thr | Pro | Tyr | Leu | Val | Lys | Ile | Pro | Ile | Pro | Ser |
|---|---|---|---|---|---|---|---|---|---|---|---|---|---|---|---|
| | | | 20 | | | | | 25 | | | | | 30 | | |

| Ala | Gln | Val | Thr | Leu | Arg | Asp | Phe | Lys | Leu | Val | Leu | Asn | Lys | Gln | Asn |
|---|---|---|---|---|---|---|---|---|---|---|---|---|---|---|---|
| | | | 35 | | | | | 40 | | | | | 45 | | |

| Asn | Asn | Tyr | Lys | Tyr | Phe | Phe | Lys | Ser | Met | Asp | Ala | Asp | Phe | Gly | Val |
|---|---|---|---|---|---|---|---|---|---|---|---|---|---|---|---|
| | 50 | | | | | 55 | | | | | 60 | | | | |

| Val | Lys | Glu | Glu | Ile | Ala | Asp | Ser | Thr | Ile | Leu | Pro | Cys | Phe | Asn |
|---|---|---|---|---|---|---|---|---|---|---|---|---|---|---|
| 65 | | | | | 70 | | | | | 75 | | | | 80 |

| Gly | Arg | Val | Val | Ser | Trp | Leu | Val | Ser | Ala | Asp | Gly | Thr | Asn | Gln | Ser |
|---|---|---|---|---|---|---|---|---|---|---|---|---|---|---|---|
| | | | | 85 | | | | | 90 | | | | | 95 | |

| Asp | Asn | Cys | Ser | Glu | Leu | Pro | Thr | Ser | Glu | Cys | Glu | Leu | Gly | Met | Gly |
|---|---|---|---|---|---|---|---|---|---|---|---|---|---|---|---|
| | | | 100 | | | | | 105 | | | | | 110 | | |

| Leu | Thr | Asn | Arg | Lys | Leu | Gln | Gln | Gln | Gln | Gln | His | Gln | Gln | Gln |
|---|---|---|---|---|---|---|---|---|---|---|---|---|---|---|
| | | 115 | | | | | 120 | | | | | 125 | | |

| Gln | Gln | Gln | Gln | Gln | Gln | Gln | His | Gln | Gln | Gln | Gln | Gln | Gln | Gln |
|---|---|---|---|---|---|---|---|---|---|---|---|---|---|---|
| | 130 | | | | | 135 | | | | | 140 | | | |

| Gln | Gln | Val | Gln | Pro | Val | Gln | Leu | Ala | Gln | Gln | Gln | Gln | Gln | Val |
|---|---|---|---|---|---|---|---|---|---|---|---|---|---|---|
| 145 | | | | | 150 | | | | | 155 | | | | 160 |

| Leu | His | His | Gln | Lys | Met | Met | Gly | Asn | Pro | Leu | Leu | Gln | Pro | Pro | Pro |
|---|---|---|---|---|---|---|---|---|---|---|---|---|---|---|---|
| | | | | 165 | | | | | 170 | | | | | 175 | |

| Leu | Thr | Tyr | Gln | Ser | Ala | Ser | Val | Leu | Ser | Ser | Asp | Leu | Asp | Ser | Thr |
|---|---|---|---|---|---|---|---|---|---|---|---|---|---|---|---|
| | | | 180 | | | | | 185 | | | | | 190 | | |

| Ser | Leu | Phe | Gly | Thr | Glu | Ser | Glu | Leu | Thr | Leu | Asp | Arg | Asp | Met | Thr |
|---|---|---|---|---|---|---|---|---|---|---|---|---|---|---|---|
| | | 195 | | | | | 200 | | | | | 205 | | | |

| Asp | Tyr | Ser | Ser | Val | Gln | Arg | Leu | Gln | Val | Arg | Lys | Lys | Pro | Gln | Arg |
|---|---|---|---|---|---|---|---|---|---|---|---|---|---|---|---|
| | 210 | | | | | 215 | | | | | 220 | | | | |

| Arg | Lys | Lys | Arg | Ala | Pro | Ser | Met | Ser | Arg | Thr | Ser | Ser | Tyr | Ser | Ser |
|---|---|---|---|---|---|---|---|---|---|---|---|---|---|---|---|
| 225 | | | | | 230 | | | | | 235 | | | | | 240 |

| Ile | Thr | Asp | Ser | Thr | Met | Ser | Leu | Asn | Ile | Ile | Thr | Val | Ser | Ile | Asn |
|---|---|---|---|---|---|---|---|---|---|---|---|---|---|---|---|
| | | | | 245 | | | | | 250 | | | | | 255 | |

| Met | Glu | Ala | Val | Asn | Phe | Leu | Gly | Ile | Ser | Ile | Val | Gly | Gln | Ser | Asn |
|---|---|---|---|---|---|---|---|---|---|---|---|---|---|---|---|
| | | | 260 | | | | | 265 | | | | | 270 | | |

| Arg | Gly | Gly | Asn | Gly | Gly | Ile | Tyr | Val | Gly | Ser | Ile | Met | Lys | Gly | Gly |
|---|---|---|---|---|---|---|---|---|---|---|---|---|---|---|---|
| | | 275 | | | | | 280 | | | | | 285 | | | |

| Ala | Val | Ala | Leu | Asp | Gly | Arg | Ile | Glu | Pro | Gly | Asp | Met | Ile | Leu | Gln |
|---|---|---|---|---|---|---|---|---|---|---|---|---|---|---|---|
| | 290 | | | | | 295 | | | | | 300 | | | | |

```
Val Asn Asp Val Asn Phe Glu Asn Met Thr Asn Asp Glu Ala Val Arg
305                 310                 315                 320

Val Leu Arg Glu Val Val Gln Lys Pro Gly Pro Ile Lys Leu Val Val
            325                 330                 335

Ala Lys Cys Trp Asp Pro Asn Pro Lys Gly Tyr Phe Thr Ile Pro Arg
            340                 345                 350

Thr Glu Pro Val Arg Pro Ile Asp Pro Gly Ala Trp Val Ala His Thr
            355                 360                 365

Gln Ala Leu Thr Ser His Asp Ser Ile Ile Ala Asp Ile Ala Glu Pro
370                 375                 380

Ile Lys Glu Arg Leu Asp Gln Asn Asn Leu Glu Gly Ile Val Lys Ala
385                 390                 395                 400

Met Thr Lys Pro Asp Ser Gly Leu Glu Ile Arg Asp Arg Met Trp Leu
            405                 410                 415

Lys Ile Thr Ile Pro Asn Ala Phe Ile Gly Ala Asp Ala Val Asn Trp
            420                 425                 430

Val Leu Glu Asn Val Glu Asp Val Gln Asp Arg Arg Glu Ala Arg Arg
            435                 440                 445

Ile Val Ser Ala Met Leu Arg Ser Asn Tyr Ile Lys His Thr Val Asn
450                 455                 460

Lys Leu Thr Phe Ser Glu Gln Cys Tyr Tyr Val Val Asn Glu Glu Arg
465                 470                 475                 480

Asn Pro Asn Leu Leu Gly Arg Gly His Leu His Pro His Gln Leu Pro
            485                 490                 495

His Gly His Gly Gly His Ala Leu Ser His Ala Asp Thr Glu Ser Ile
            500                 505                 510

Thr Ser Asp Ile Gly Pro Leu Pro Asn Pro Ile Tyr Met Pro Tyr
            515                 520                 525

Ser Ala Thr Tyr Asn Pro Ser His Gly Tyr Gln Pro Ile Gln Tyr Gly
530                 535                 540

Ile Ala Glu Arg His Ile Ser Ser Gly Ser Ser Ser Asp Val Leu
545                 550                 555                 560

Thr Ser Lys Asp Ile Ser Ala Ser Gln Ser Asp Ile Thr Ser Val Ile
            565                 570                 575

His Gln Ala Asn Gln Leu Thr Ile Ala Ala His Gly Ser Asn Lys Ser
            580                 585                 590

Ser Gly Ser Ser Asn Arg Gly Gly Gly Gly Gly Gly Gly Gly Gly
            595                 600                 605

Asn Asn Thr Asn Asp Gln Asp Val Ser Val Phe Asn Tyr Val Leu
610                 615                 620
```

<210> SEQ ID NO 13
<211> LENGTH: 476
<212> TYPE: DNA
<213> ORGANISM: Hom sapiens

<400> SEQUENCE: 13

```
tctggtcaaa ccagagcacg aaacaacaca gcgctggaat actcgggcac cagcggtgcc      60
tccggcgact cctcccatcc gggtcgcatg agcttcttct ccaaactctc ctcacgtttt     120
agcaaacgtc ccacaatcgc agacgaggcg gctaagccac gagttctacg attcacatgg     180
tcaatgaaaa ccacatcgcc cctgatgccc gatcagataa tgcaaaagat cagggaggtg     240
ctggaccaga ataattgcga ctacgaacag cgggaaagat tcgtcctgtg gtgcgtgcat     300
```

```
ggagatccca atacggactc actggtgcaa tgggaaatag aagtgtgcaa gctgccacga      360
ctctctctga atggagtgcg cttcaagcga atttccggca ccagcattgg cttcaagaac      420
attgcgtcgc gcattgcttt tgacctcaag ctgtgactta accaaacgaa caacga          476

<210> SEQ ID NO 14
<211> LENGTH: 151
<212> TYPE: PRT
<213> ORGANISM: Homo sapiens

<400> SEQUENCE: 14

Ser Gly Gln Thr Arg Ala Arg Asn Asn Thr Ala Leu Glu Tyr Ser Gly
  1               5                  10                  15

Thr Ser Gly Ala Ser Gly Asp Ser Ser His Pro Gly Arg Met Ser Phe
                 20                  25                  30

Phe Ser Lys Leu Ser Ser Arg Phe Ser Lys Arg Pro Thr Ile Ala Asp
                 35                  40                  45

Glu Ala Ala Lys Pro Arg Val Leu Arg Phe Thr Trp Ser Met Lys Thr
 50                  55                  60

Thr Ser Pro Leu Met Pro Asp Gln Ile Met Gln Lys Ile Arg Glu Val
 65                  70                  75                  80

Leu Asp Gln Asn Asn Cys Asp Tyr Glu Gln Arg Glu Arg Phe Val Leu
                 85                  90                  95

Trp Cys Val His Gly Asp Pro Asn Thr Asp Ser Leu Val Gln Trp Glu
                100                 105                 110

Ile Glu Val Cys Lys Leu Pro Arg Leu Ser Leu Asn Gly Val Arg Phe
                115                 120                 125

Lys Arg Ile Ser Gly Thr Ser Ile Gly Phe Lys Asn Ile Ala Ser Arg
130                 135                 140

Ile Ala Phe Asp Leu Lys Leu
145                 150
```

ISOLATED DISHEVELLED ASSOCIATED KINASES, POLYNUCLEOTIDES ENCODING THE KINASES, AND METHODS OF USE THEREOF

CROSS REFERENCE

This application is a continuation application of U.S. patent application Ser. No. 09/661,965, filed Sep. 14, 2000, abandoned, which application claims the benefit of U.S. Provisional Patent Application No. 60/158,021, filed Oct. 6, 1999, which applications are incorporated herein by reference in their entirety.

GOVERNMENT SUPPORT

The government may have certain rights in this application, pursuant to National Institutes of Health grant no. PO HL 43821.

FIELD OF THE INVENTION

The invention relates generally to compounds which regulate biological pathways. More particularly the invention relates to a dishevelled associated kinase and its effects on specific pathways associated with disease.

BACKGROUND OF THE INVENTION

Proteins of the Wnt family function in a variety of inductive signaling events, control cell polarity, determine cell fate and promote cell proliferation (Nusse et al. (1992) *Cell* 69:1073–1087; McMahon (1992) *Trends Genet.* 8:236–242). The first known wnt gene, *Drosophila* wingless (wg) gene, was identified genetically by a weak mutation that disrupts formation of the wing of adult flies (Sharma et al. (1976) *Dev. Biol.* 48:461–464) and it was later found that null mutations in wingless result in patterning defects and embryonic lethality (Nüsslein-Volhard et al. (1980) *Nature* 287:795–801). Wg protein is required for patterning of the *Drosophila* embryo and development of muscle, midgut, neuron and imaginal disc. In *C. elegans*, these genes are required for generation of cell polarity and cell fate determination. In vertebrates, Wnt proteins are required for body axis formation and proper development of brain, kidney and many other organs (Cadigan et al. (1997) *Genes Dev.* 11:3286–3305).

Through biochemical and genetic studies, several components of the Wnt signaling pathway have been identified. Much attention has focused on the role of the β-catenin/Armadillo protein which, in response to Wnt/Wg, becomes stabilized, moves to the nucleus and forms complex with the LEF1/TCF transcription factors to regulate gene expression. The level of cytosolic β-catenin is determined by its interaction with a number of proteins including those in a multiprotein complex of Axin, glycogen synthase kinase-3β (GSK-3β), adenomatous polyposis coli (APC), and other proteins (Polakis (1999) *Curr. Opin. Genet. Dev.* 9:15–21). The mechanism by which the Wnt signal is transmitted to the Axin/GSK-3β/APC complex is unclear but it involves interaction of Wnt with its receptors, which are members of Frizzled (Frz) family of seven transmembrane proteins. When Wnt is activated by binding of Wnt to the Frz family of receptors, the Dsh protein is hyperphosphorylated and recruited to the membrane area. Activated Dsh inhibits GSK-3β action, which normally phosphorylates β-catenin and directs it, together with APC and axin family members to degradation by the ubiquitin-proteosome system. Decreased degradation of β-catenin leads to its accumulation, nuclear translocation, and association with LEF1/TCF. Ben-Ze'ev and Geiger (1998) *Curr. Opin. Cell Biol.* 10:629–639.

Disregulation of the Wnt/Wg pathway and accumulation of β-catenin is associated with a variety of cancers. For example, in colon and other cancers, mutations in APC or presumptive GSK-3β phosphorylation sites of β-catenin are associated with constitutive activation of LEF1/TCF transcription. Sparks et al. (1998) *Cancer Res.* 58:1130–1134; and Kolligs et al. (1999) *Mol. Cell. Biol.* 19:5696–5706. Constitutive activation of LEF1 was shown to induce oncogenic transformation of chicken embryo fibroblasts. Aoki et al. (1999) *Proc. Natl. Acad. Sci. USA* 96:139–144. Accumulation of β-catenin is associated with intestinal tumors. Crawford et al. (1999) *Oncogene* 18:2883–2891. Regulation of β-catenin stability is also thought to play a major role in melanomas, breast cancer, neuroblastoma, ovarian carcinomas, medulloblastomas, and other tumors. Aberle et al. (1996) *Proc. Natl. Acad. Sci. USA* 92:6384–6388; Rubinfeld et al. (1997) *Science* 275:1790–1792; Zurawel et al. (1998) *Cancer Res.* 58:896–899; Palacios and Gamallo (1998) *Cancer Res.* 58:1344–1347; Mai et al. (1999) *Genomics* 55:341–344. β-catenin may act as an oncogene by excessively activating gene(s) that directly contribute to tumor progression.

There exists a need in the art for an understanding of the cellular pathways involved in control of cell proliferation. There further exists a need for ways of regulating uncontrolled cell proliferation. The present invention addresses these needs and provides additional advantages as well.

SUMMARY OF THE INVENTION

Dishevelled Associated Kinase (DAK) was isolated and purified, and cDNA encoding DAK was cloned and sequenced. The DAK protein regulates a pathway associated with several forms of cancer. Accordingly, an assay of the invention identifies compounds which inhibit DAK, which compounds are candidates for the treatment of certain forms of cancer. Further, the invention comprises assaying tissue for DAK activity, thereby providing a diagnostic tool for detecting certain abnormalities.

An aspect of the invention are isolated Dishevelled Associated Kinase (DAK) polypeptides. DAK polypeptides are used in methods of the invention to identify compounds that inhibit DAK enzyme activity and/or DAK-Dsh binding. Compositions comprising the isolated DAK polypeptides are further provided.

A further aspect of the invention are isolated DAK polynucleotides. DAK polynucleotides are used to produce DAK polypeptides, and are further useful in detecting hybridizing polynucleotides, and can therefore be used to detect the presence of and/or measure a level of, DAK mRNA in a biological sample, as well as to detect related polynucleotides. Recombinant vectors and host cells comprising the isolated polynucleotides are further provided.

Another aspect of the invention is an antibody which specifically binds DAK. Such antibodies are useful in assays to detect the presence of DAK protein, and are further useful in altering DAK-Dsh binding.

A further aspect of the invention are inhibitors of DAK-Dsh interactions. Such inhibitors are useful in regulating entry into, and accumulation of, β-catenin in the nucleus of a eukaryotic cell. Reducing β-catenin accumulation in the nucleus may reduce cell proliferation.

Yet another aspect of the invention is an assay which detects DAK kinase activity in a biological sample. A further aspect of the invention are assays which detect the presence and/or level of DAK mRNA, and thus DAK expression, in a biological sample. In another aspect, the invention provides assays for detecting the presence and/or level of DAK polypeptide in a biological sample.

The invention further provides a variety of methods for detecting agents which modulate DAK levels and/or activity. Thus, the invention provides assays for determining compounds which modulate DAK kinase activity, including compounds which inhibit and compounds which activate DAK kinase activity. The present invention further provides methods for modulating a level of DAK polypeptide and/or DAK mRNA in a cell. The invention further provides methods for detecting agents which modulate DAK-Dsh interaction.

An advantage of the invention is that compounds found to inhibit DAK kinase activity, inhibit DAK-Dsh interactions, inhibit DAK mRNA levels, and/or inhibit DAK polypeptide levels are candidates for the treatment for certain forms of cancer. Accordingly, in one aspect, the invention provides methods of treating various forms of cancer.

These and other objects, aspects, advantages, and features of the invention will become apparent to those persons skilled in the art upon reading the details of the invention as more fully described below.

BRIEF DESCRIPTION OF THE DRAWINGS

FIGS. 4A and 4B show the amino acid sequence of two isoforms of DAK referred to here as DAKa (SEQ ID NO:2) and DAKb, (SEQ ID NO:4).

FIGS. 7A and 7B are graphs depicting suppression of Wnt-induced (FIG. 7A), but not of β-catenin-induced (FIG. 7B) activation of LEF1 reporter activity, by a 36-amino acid DAK-binding peptide.

FIGS. 8A–8C depict an amino acid sequence alignment DAKa (SEQ ID NO:2), DAKb (SEQ ID NO:4), and DAKc (SEQ ID NO:14) amino acid sequence. Boxes with heavy shading indicate amino acid identity; boxes with light shading indicate amino acid similarity.

FIG. 9 depicts the nucleotide sequence of DAKa (SEQ ID NO:1).

FIGS. 10A and 10B depict the nucleotide sequence of DAKb (SEQ ID NO:3).

FIG. 11 depicts the nucleotide sequence of DAKc (SEQ ID NO:13).

MODES OF CARRYING OUT THE INVENTION

Figure 1:
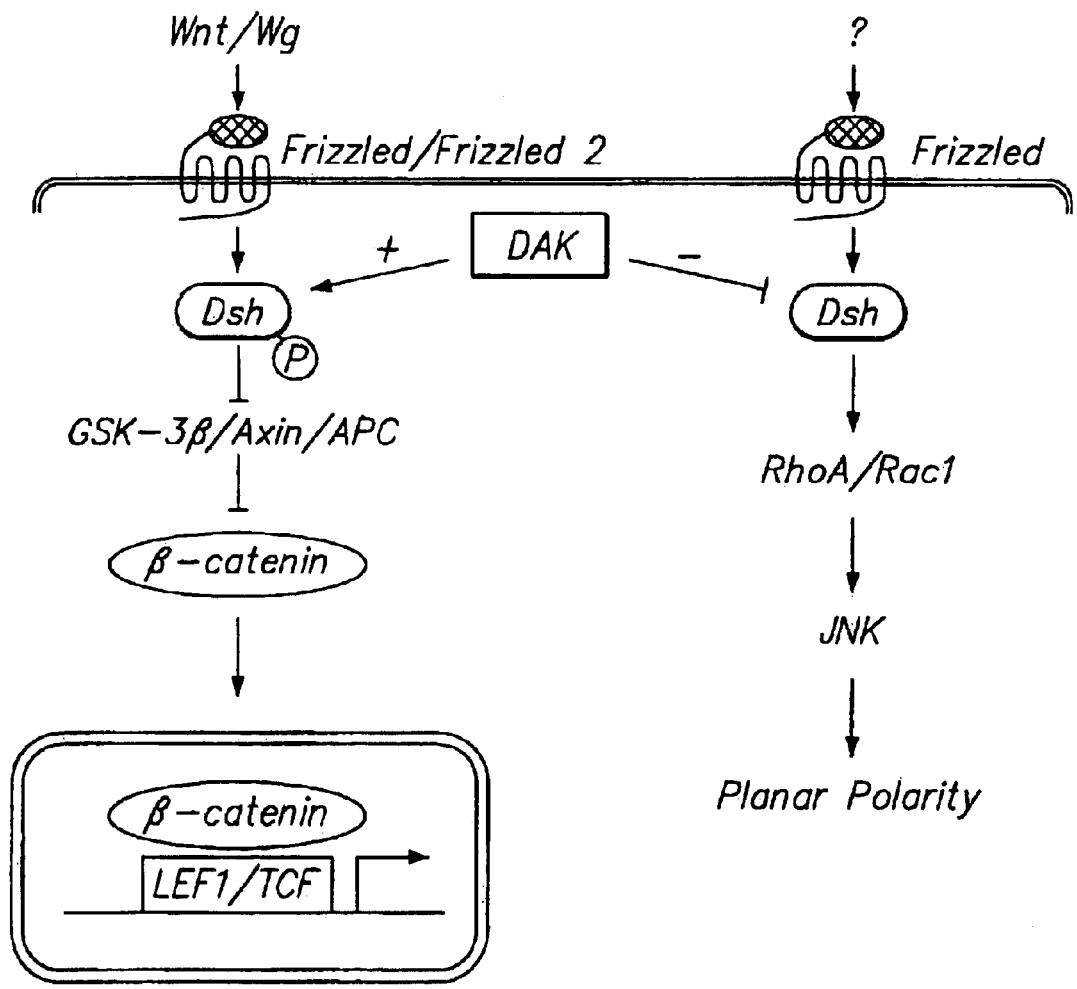
FIG. 1 is a schematic representation of the role of DAK in the regulation of Wnt/Wg signaling and the JNK/Planar Polarity Pathway.

It has been discovered that a protein, termed Dishevelled Associated Kinase, or DAK, binds to and phosphorylates Dishevelled (Dsh) protein, a component of the Wnt/Wg signalling pathway which plays an important role in control of cellular proliferation. A model for the roles of DAK and Dsh in signalling is shown in FIG. 1. It has been found that DAK binds to a conserved region on Dsh and its activity is correlated with Dsh phosphorylation during embryo development. It has been observed that more than 90% of colon cancers are caused by the aberrant regulation of the Wnt/Wg pathway. Peifer (1997) *Science* 275:1752–1753. Aberrancies in this pathway have also been implicated in human melanoma and certain tumors in mice. Furthermore, mice with knockout of a dishevelled homolog show neurological defects, suggesting that abnormalities in this pathway may play a role in certain neurological disorders as well. Lijam et al. (1997) *Cell* 90:895–905.

The present invention relates to isolated Dishevelled Associated Kinase polypeptides, isolated polynucleotides encoding the polypeptides, and methods of use of the polypeptides and polynucleotides.

Before the present proteins, polynucleotides, antibodies, assays and methods of the invention are disclosed and described, it is to be understood that this invention is not limited to particular sequences, antibodies, assays and the like as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are incorporated herein by reference to disclose and describe methods and/or materials in connection with which the publications are cited. Nothing herein is to be construed as an admission that the present invention is not entitled to antedate such publication by virtue of prior invention. Further, the dates of publication provided are subject to change if it is found that the actual date of publication is different from that provided here.

General Methods

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, *Molecular Cloning: A Laboratory Manual*, Second Edition (1989), *Oligonucleotide Synthesis* (M. J. Gait Ed., 1984), *Animal Cell Culture* (R. I. Freshney, Ed., 1987), the series Methods in Enzymology Academic Press, Inc.); *Gene Transfer Vectors for Mammalian Cells* (J. M. Miller and M. P. Calos Eds. 1987), *Handbook of Experimental Immunology*, (D. M. Weir and C. C. Blackwell, Eds.); Current *Protocols in Molecular Biology*, (F. M. Ausubel, et al., Eds. 1987, and updates); and *Current Protocols in Immunology* (J. E. Coligan, A. M. Kruisbeek, D. H. Margulies, E. M. Shevach and W. Strober Eds. 1991).

Definitions

For the purposes of the present application, singular forms "a", "and", and "the" include plural referents unless the context clearly indicates otherwise. Thus, for example, reference to "a polypeptide" includes large numbers of polypeptides, reference to "an agent" includes large numbers of agents and mixtures thereof, reference to "the method" includes one or more methods or steps of the type described herein.

The term "polypeptide" refers to a polymer of amino acids and does not refer to a specific length of the product; thus, peptides, oligopeptides, and proteins are included within the definition of polypeptide. This term also does not refer to or exclude post-translational modifications of the polypeptide, for example, glycosylations, acetylations, phosphorylations and the like. Included within the definition are, for example, polypeptides containing one or more analogs of an amino acid (including, for example, unnatural amino acids, non-coded amino acids, etc.), polypeptides with substituted linkages, as well as other modifications known in the art, both naturally occurring and non-naturally occurring.

The terms "polynucleotide" and "nucleic acid", used interchangeably herein, refer to a polymeric forms of nucleotides of any length, either ribonucleotides or deoxynucleotides. Thus, this tem includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841–1848; Chaturvedi et al. (1996) Nucl. Acids Res. 24:2318–2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

For hybridization probes, it may be desirable to use nucleic acid analogs, in order to improve the stability and binding affinity. A number of modifications have been described that alter the chemistry of the phosphodiester backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire phosphodiester backbone with a peptide linkage.

Sugar modifications are also used to enhance stability and affinity. The a-anomer of deoxyribose may be used, where the base is inverted with respect to the natural b-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

By "antisense polynucleotide" is mean a polynucleotide having a nucleotide sequence complementary to a given polynucleotide sequence (e.g, a polynucleotide sequence encoding a DAK polypeptide) including polynucleotide sequences associated with the transcription or translation of the given polynucleotide sequence (e.g., a promoter of a polynucleotide encoding DAK polypeptide), where the antisense polynucleotide is capable of hybridizing to a DAK polypeptide-encoding polynucleotide sequence. Of particular interest are antisense polynucleotides capable of inhibiting transcription and/or translation of a DAK-encoding polynucleotide either in vitro or in vivo.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at http://ww.ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70:173–187 (1997). Also, the GAP program using the Needleman and Wunsch alignment method can be utilized to align sequences. See J. Mol. Biol. 48:443–453 (1970)

Of interest is the BestFit program using the local homology algorithm of Smith Waterman (Advances in Applied Mathematics 2: 482–489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127–149, 1988, Alan R. Liss, Inc. Percent sequence identity is calculated by FastDB based upon the following parameters:

| | |
|---|---|
| Mismatch Penalty: | 1.00; |
| Gap Penalty: | 1.00; |
| Gap Size Penalty: | 0.33; and |
| Joining Penalty: | 30.0. |

One parameter for determining percent sequence identity is the "percentage of the alignment region length" where the strongest alignment is found.

The percentage of the alignment region length is calculated by counting the number of residues of the individual sequence found in the region of strongest alignment. This number is divided by the total residue length of the target or query polynucleotide sequence to find a percentage. An example is shown below:

```
Target sequence:    GCGCGAAATACTCACTCGAGG
                    |   ||| |||| |||
Query sequence:     TATAGCCCTAC.CACTAGAGTCC
                    1   5    10   15
```

The region of alignment begins at residue 9 and ends at residue 19. The total length of the target sequence is 20 residues. The percent of the alignment region length is 11 divided by 20 or 55%, for example.

Percent sequence identity is calculated by counting the number of residue matches between the target and query polynucleotide sequence and dividing total number of matches by the number of residues of the target or query sequence found in the region of strongest alignment. For the example above, the percent identity would be 10 matches divided by 11 residues, or approximately, 90.9%

The percent of the alignment region length is typically at least about 55% of total length of the sequence, more typically at least about 58%, and even more typically at least about 60% of the total residue length of the sequence. Usually, percent length of the alignment region can be as great as about 62%, more usually as great as about 64% and even more usually as great as about 66%.

As used herein the term "isolated" is meant to describe a polynucleotide, a polypeptide, an antibody, or a host cell that is in an environment different from that in which the polynucleotide, the polypeptide, the antibody, or the host cell naturally occurs. As used herein, the term "substantially purified" refers to a compound (e.g., either a polynucleotide or a polypeptide or an antibody) that is removed from its natural environment and is at least 60% free, preferably 75% free, and most preferably 90% free from other components with which it is naturally associated.

"Recombinant," as used herein, means that a particular DNA sequence is the product of various combinations of cloning, restriction, and ligation steps resulting in a construct having a structural coding sequence distinguishable from homologous sequences found in natural systems. Generally, DNA sequences encoding the structural coding sequence can be assembled from cDNA fragments and short oligonucleotide linkers, or from a series of oligonucleotides, to provide a synthetic gene which is capable of being expressed in a recombinant transcriptional unit. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where such sequences do not interfere with manipulation or expression of the coding regions. Thus, the term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. By "construct" is meant a recombinant nucleic acid, generally recombinant DNA, that has been generated for the purpose of the expression of a specific nucleotide sequence(s), or is to be used in the construction of other recombinant nucleotide sequences.

A "host cell", as used herein, denotes microorganisms or eukaryotic cells or cell lines cultured as unicellular entities which can be, or have been, used as recipients for recombinant vectors or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

A "transcriptional control region" (sometimes referred to as a "transcriptional regulatory region") encompasses all the elements necessary for transcription, and may include elements necessary for regulation and cell-specific transcription. Thus, a transcriptional control region includes at least the promoter sequence, and may also include other regulatory sequences such as enhancers, and transcription factor binding sites.

A "transcriptional control region heterologous to a coding region" is one that is not normally associated with the coding region in nature.

"Operably linked" refers to a juxtaposition wherein the components so described are in a relationship permitting them to function in their intended manner. For instance, a promoter is operably linked to a coding sequence if the promoter affects its transcription or expression.

"Regulatory sequences" refer to those sequences normally associated with (for example within 50 kb) of the coding region of a locus which affect the expression of the gene (including transcription of the gene, and translation, splicing, stability, or the like of the messenger RNA). Regulatory sequences include, inter alia, promoters, enhancers, splice sites and polyadenylation sites.

By "transformation" is meant a permanent or transient genetic change induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

The term "immunologically active" defines the capability of the natural, recombinant or synthetic DAK polypeptide, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal.

A "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids and tissue samples.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. Cancerous cells can be benign or malignant.

Isolated DAK Polypeptides of the Invention

The present invention provides isolated Dishevelled Associated Kinase (DAK) polypeptides. The inventors have discovered that DAK specifically binds to and phosphorylates Dishevelled (Dsh), a protein involved in the Wnt/Wg signaling pathway believed to play important roles in development of multicellular organisms, and in controlling cell proliferation. DAK polypeptides can be used to generate antibodies which specifically bind to DAK polypeptides. DAK polypeptides are also useful in assay methods to identify agents which modulate DAK kinase activity, and/or which modulate DAK-Dsh binding.

The term "DAK polypeptide" encompasses DAK polypeptides from a variety of eukaryotic species, including, but not limited to, mammalian species, such as rat, mouse, and human; insect species; reptiles; yeast; nematodes; and amphibians.

As used herein, "DAK polypeptide" refers to an amino acid sequence of a recombinant or non-recombinant polypeptide having an amino acid sequence of i) a native DAK polypeptide, ii) a fragment of a DAK polypeptide, iii) polypeptide analogs of a DAK polypeptide, iv) variants of a DAK polypeptide; v) an immunologically active fragment of a DAK polypeptide; and vi) fusion proteins comprising a DAK polypeptide. DAK polypeptides of the invention can be obtained from a human biological sample, or from any source whether natural, synthetic, semi-synthetic or recombinant.

"DAK polypeptide" refers to the amino acid sequences of isolated DAK polypeptide obtained from a prokaryotic or eukaryotic organism, and is meant to include all naturally-occurring allelic variants, and is not meant to limit the amino acid sequence to the complete, native amino acid sequence associated with the recited protein molecule. The term "DAK polypeptide" encompasses an amino acid sequence encoded by an open reading frame (ORF) of the DAK polynucleotides described herein, including the full-length native polypeptide and fragments thereof, particularly biologically active fragments and/or fragments corresponding to functional domains, e.g., a Dsh-phosphorylation domain, a Dsh-binding domain or region, etc.; and including fusions of the subject polypeptides to other proteins or parts thereof.

Those skilled in the art will appreciate that changes can be made to DAK polypeptide sequences, including the sequences depicted in SEQ ID NO:2 (DAK a) and NO:4 (DAK b) without substantially affecting a function of the DAK polypeptide. Thus, the term "DAK polypeptide" encompasses polypeptides with conservative amino acid substitutions compared with the sequences depicted in SEQ ID NO:2, NO:4, and SEQ ID NO:14. Examples of conservative amino acid substitutions include Ser/Thr; Ala/Val; Leu/Ile; Asp/Glu; and Phe/Tyr. Clearly, other amino acid substitutions, deletions, and insertions can be made to the polypeptide without affecting one or more functions of the polypeptide. Those skilled in the art, given the guidance provided in the instant specification, can readily determine whether a given function of a DAK polypeptide is preserved. One such function is phosphorylation of a Dsh protein by a DAK protein of the invention. Another such function is binding to a Dsh protein. Yet another function is binding to other, non-Dsh protein(s). As shown in the Examples, a lysine at amino acid position 282 of DAKa was found to be important in DAK kinase activity. Thus, in some embodiments, a DAK polypeptide retains amino acids important for kinase activity, including, but not limited to, Lys 282 of DAKa.

The term "DAK polypeptide" includes isoforms of DAKa and DAKb polypeptides. As an example, an isoform, designated DAKc, was identified, which has a C-terminal extension relative to DAKa and DAKb, as shown in FIG. 8. The nucleotide sequence of DAKc is set forth in SEQ ID NO:13; the amino acid sequence of DAKc is set forth in SEQ ID NO:14.

Whether a DAK polypeptide phosphorylates a Dsh polypeptide (or fragment thereof) is readily determined, using any known assay, including the kinase assays described in Example 1 (in vitro kinase activity assay) and Example 2 (in-gel kinase assay).

Whether a DAK polypeptide binds to a Dsh polypeptide can be readily determined, using any known assay for protein-protein binding, including, but not limited to, precipitation of DAK from a sample using a GST-Dsh fusion protein comprising (a) amino acids 172 to 395 of Dsh; (b) amino acids 172 to 250 of Dsh; (c) amino acids 200 to 249 of Dsh; or (d) amino acids 214 to 249 of Dsh.

The term "DAK polypeptide" encompasses a polypeptide comprising 6 or more contiguous amino acids of the sequence depicted in SEQ ID NO:2 or NO:4 or SEQ ID NO:14. Thus, the term "DAK polypeptide" encompasses a polypeptide comprising at least about 6, 10, 15, 20, 25, 50, 75, 100, 200, 300, 400, 500, 600, 700, 800, or 830 contiguous amino acids of the sequence set forth in SEQ ID NO:2. The term "DAK polypeptide further encompasses a polypeptide comprising at least about 6, 10, 15, 20, 25, 50, 75, 100, 200, 300, 400, 500, 600, 700, 800, 900, or 1000 contiguous amino acids of the sequence set forth in SEQ ID NO:4. In some embodiments, a DAK polypeptide has the entire sequence as shown in SEQ ID NO:2 or NO:4.

Also encompassed by the term "DAK polypeptide" is a polypeptide sharing at least about 70%, more preferably at least about 80%, more preferably at least about 85%, more preferably at least about 87%, even more preferably at least about 90% or more amino acid sequence identity with the sequence depicted in SEQ ID NO:2 or NO:4.

It has been discovered that a DAK polypeptide binds to and phosphorylates Dsh protein in vitro, as shown in Examples 1 and 2. Specifically, DAK binds to and phosphorylates Dsh in a 36-amino acid region from amino acids 214–249 of a Dsh amino acid sequence. This region is termed "DM5". Accordingly, in some embodiments, a DAK polypeptide phosphorylates a Dsh polypeptide in the DM5 region of Dsh, i.e., the DAK polypeptide has kinase activity toward Dsh. Whether a DAK polypeptide has kinase activity toward Dsh can readily be determined using any known assay for kinase activity, including, for example, the assay described in Example 1.

Also included in the term "DAK polypeptide" are antigenic epitopes of a DAK polypeptide. Those skilled in the art can readily determine which peptide fragments are antigenic epitopes. As a non-limiting example of how one can determine which region(s) of a protein are likely to be exposed on the surface (i.e., hydrophilic domains), and therefore potentially antigenic, one can analyze the amino acid sequence using Kyte-Doolittle hydropathicity analysis and/or Hopp-Woods hydrophilicity analysis. Kyte and Doolittle (1982) *J. Mol. Biol.* 157:105; and Hopp and Woods (1981) *Proc. Natl. Acad. Sci. USA* 78:3824.

The Dsh protein has been described. Klingensmith et al. (1994) *Genes Dev.* 8:118–130; and Theisen et al. (1994) *Development* 120:347–360. Dsh has homologs in *C. elegans, Xenopus* and mammals (Sokol et al. (1995) *Development* 121:3487; Klingensmith et al. (1996) *Mech. Dev.* 58:15–26; Ruvkun and Hobert (1998) *Science* 282:2033–2041; and Lee et al. (1999) *J. Biol. Chem.* 274:21464–21470). Dsh is a modular protein with three conserved domains: DIX, an N-terminal domain; DEP, a C-terminal domain; and PDZ, between the DIX and DEP domains. The DIX domain in Dsh is 50 amino acids long and shares homology with a C-terminal region in Axin protein family (Zeng et al. (1997) *Cell* 90:181–192; Ikeda et al. (1998) *EMBO* 17:1371–1384; Behrens et al. (1998) *Science* 280:596–599). The PDZ domain is 90 amino acids long and is homologous to domains known to mediate protein-protein interaction in other proteins. The DEP domain is about 60 amino acids long and it is also conserved in RGS (regulator of G-protein signal) proteins and Pleckstrin (Ponting et al. (1996) *Trends Biochem. Sci.* 21:245–246). Overexpression of Dsh can result in activation of both Wnt/β-catenin and JNK pathways in cultured cells (Yanagawa et al. (1995) *Genes Dev.* 9:1087–1097; Boutros et al. (1998) *Cell* 94:109–118).

Figures 2, 3:
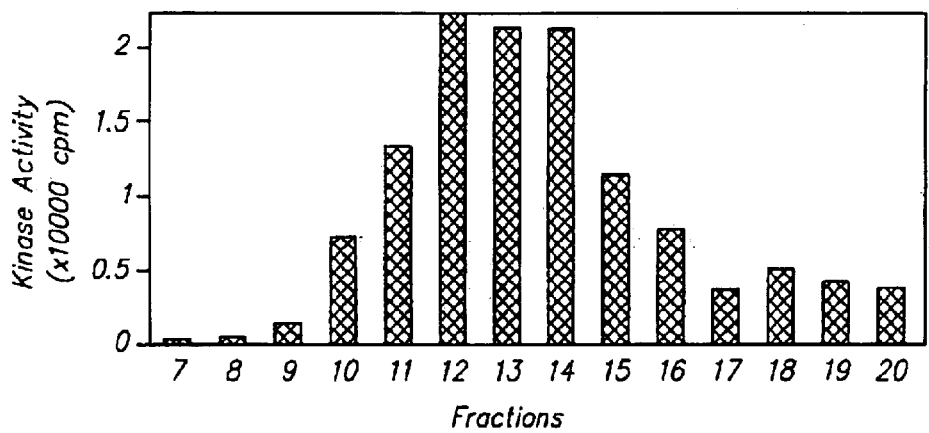
FIG. 2 is a summary of results obtained by mapping the DAK binding site on Dsh where the "+" sign indicates the re-binding of DAK or the binding of DAK activities directly from embryo lysates to various segments of Dsh in vitro. The bottom of the figure shows the sequence of the DAK binding region on Dsh and compares that sequence to four different Dsh homologs—one from Xenopus (xDsh) and three from mouse (mDvl).
FIG. 3 is a graph of kinase activity for different Mono S fractions of DAK purified from *Drosophila* embryo.

The nucleotide sequences, and amino acid sequences of predicted translation products, of Dsh cDNAs are found under GenBank Accession No.s U02491 (amino acid sequence is provided in SEQ ID NO:12) and L26974. For the purposes of the present invention, a "Dsh protein" or "Dsh polypeptide" encompasses the polypeptide having the published sequence homologs thereof from other species; one or more of the aforementioned Dsh domains; as well as fragments and variants which interact with, and are phosphorylated by, a DAK polypeptide of the invention. As discussed in more detail below, particular fragments of Dsh were found to be phosphorylated by DAK. Examples of such fragments are shown in FIG. 2 (SEQ ID NOS: 5–9). Accordingly, these fragments are included in the term "Dsh polypeptide."

Production of DAK Polypeptides

DAK polypeptides can be isolated from a biological source, can be produced synthetically, or can be produced recombinantly, i.e., a DAK-coding region can be inserted into an expression vector, and the DAK-coding region transcribed and translated.

DAK polypeptides can be isolated from biological sources, using standard methods of protein purification known in the art. Example 3 gives a detailed protocol: for DAK isolation from *Drosophila* embryos. This, or any other suitable method can be used. DAK can also be isolated from a biological source by affinity chromatography, using Dsh, or a DAK-binding fragment thereof, such as the "DM5 region", e.g., amino acids 214–249, as shown in FIG. 2, using standard methods known in the art.

One may employ solid phase peptide synthesis techniques, where such techniques are known to those of skill in the art. See Jones, The Chemical Synthesis of Peptides (Clarendon Press, Oxford)(1994). Generally, in such methods a peptide is produced through the sequential additional of activated monomeric units to a solid phase bound growing peptide chain.

For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the subject gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the protein will benefit from native folding and post-translational modifications. Small peptides can also be synthesized in the laboratory. Polypeptides that are subsets of the complete amino acid sequence may be used to identify and investigate parts of the protein important for function, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique.

Isolated DAK Polynucleotides of the Invention

The present invention provides isolated polynuleotides encoding a DAK polypeptide. These polynucleotides can be used, when in a recombinant expression vector, to produce the encoded DAK polypeptide. They are also useful as hybridization probes in methods of detecting DAK gene expression, specifically transcription. Accordingly, the invention further provides recombinant vectors and host cells comprising DAK polynucleotides of the invention.

Novel polynucleotides of the invention comprise a sequence set forth in any one of SEQ ID NO:1 (DAKa nt) or SEQ ID NO:3 (DAKb nt) or SEQ ID NO:13 (DAKc), or an identifying sequence thereof. An "identifying sequence" is a contiguous sequence of residues at least about 10 nucleotides (nt) to about 20 nt in length, usually at least about 50 nt to about 100 nt in length, that uniquely identifies the provided sequence. Encompassed in the term "DAK polynucleotide" are polynucleotides comprising about 10, 20, 25, 50, 75, 100, 125, 150, 175, 200, 225, 250, 300, 400, 500, 600, 700, 800, 900, 1000, 1500, or 2000 contiguous nucleotides of SEQ ID NO:1, including the entire coding region of SEQ ID NO:1. Further encompassed in the term "DAK polynucleotide" are polynucleotides comprising about 10, 20, 25, 50, 75, 100, 125, 150, 175, 200, 225, 250, 300, 400, 500, 600, 700, 800, 900, 1000, 1500, 200, 2500, or 3000 contiguous nucleotides of SEQ ID NO:3, including the entire coding region of SEQ ID NO:3. Polynucleotides comprising sequences which encode the region of the DAK protein that interacts with Dsh are also of interest. Such fragments are often contained within the coding region, and may be about 250 to 500 nucleotides in length, up to the complete coding sequence.

Polynucleotides of the invention also include nucleic acids having sequence similarity or sequence identity to the sequences provided in SEQ ID NO:1, SEQ ID NO:3, and SEQ ID NO:13. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity can be determined by hybridization under stringent conditions, for example, at 50° C. or higher and 0.1×SSC (9 mM NaCl/0.9 mM sodium citrate). Hybridization methods and conditions are well known in the art, see, e.g., U.S. Pat. No. 5,707,829. Nucleic acids that are substantially identical to the provided nucleic acid sequences, e.g. allelic variants, genetically altered versions of the gene, etc., bind to the provided nucleic acid sequences (SEQ ID NOS:1, 3, or 13) under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, yeast, nematodes, etc.

"Hybridization" refers to the association of two nucleic acid sequences to one another by hydrogen bonding. Two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook, et al., Molecular Cloning: A Laboratory Manual, 2nd Ed. (1989), Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated $T_m$ of the hybrid under study. The temperature and salt conditions can often be determined empirically in preliminary experiments in which samples of genomic DNA immobilized on filters are hybridized to the sequence of interest and then washed under conditions of different stringencies. See Sambrook, et al., supra, at page 9.50.

Variables to consider when performing, for example, a Southern blot are (1) the complexity of the DNA being blotted and (2) the homology between the target and the sequences being detected. The total amount of the polynucleotides to be studied can vary a magnitude of 10, from 0.1 to 1 μg for a plasmid or phage digest to $10^{-9}$ to $10^{-8}$ μg for a single copy gene in a highly complex eukaryotic genome. For lower complexity polynucleotides, substantially shorter blotting, hybridization, and exposure times, a smaller amount of starting polynucleotides, and lower specific activity of a target polynucleotide can be used. For example, a single-copy yeast gene can be detected with an exposure time of only 1 hour starting with 1 μg of yeast DNA, blotting for two hours, and hybridizing for 4–8 hours with a target polynucleotide radiolabeled with $10^8$ cpm/μg. For a single-copy mammalian gene a conservative approach would start with 10 μg of DNA, blot overnight, and hybridize overnight in the presence of 10% dextran sulfate using a target polynucleotide radiolabeled with greater than $10^8$ cpm/μg, resulting in an exposure time of ~24 hours.

Several factors can affect the melting temperature ($T_m$) of a DNA—DNA hybrid between the target and sequence of interest, and consequently, the appropriate conditions for hybridization and washing. In many cases the target is not 100% homologous to the fragment. Other commonly encountered variables include the length and total G+C content of the hybridizing sequences and the ionic strength and formamide content of the hybridization buffer. The effects of all of these factors can be approximated by a single equation:

$$T_m = 81 + 16.6(\log 10 C_i) + 0.4[\%G+C] - 0.6(\% \text{ formamide}) - 600/n - 1.5(\% \text{ mismatch}),$$

where Ci is the salt concentration (monovalent ions) and n is the length of the hybrid in base pairs (slightly modified from Meinkoth and Wahl, (1984) *Anal. Biochem.* 138: 267–284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the labeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a target polynucleotide with 95% to 100% sequence identity to the sequence to be detected, 37° C. for 90% to 95% sequence identity, and 32° C. for 85% to 90% sequence identity. For lower percentage sequence identity, formamide content should be lowered and temperature adjusted accordingly, using the equation above. If the homology between the target polynucleotide and the sequence to be detected are not known, the simplest approach is to start with both hybridization and wash conditions which are nonstringent. If nonspecific bands or high background are observed after autoradiography, the filter can be washed at high stringency and reexposed. If the time required for exposure makes this approach impractical, several hybridization and/or washing stringencies should be tested in parallel. Stringent conditions include hybridization in a solution of at least about 5×SSC at 65° C., or at least about 4×SSC at 42° C.; see, for example, U.S. Pat. No. 5,707,829, the disclosure of which is herein incorporated by reference.

Generally, hybridization is performed using at least 18 contiguous nucleotides of at least one of SEQ ID NO:1, NO:3, or NO:13. That is, when at least 18 contiguous nucleotides of one of the disclosed SEQ ID NO:1, NO:3, or NO:13 is used as a probe, the probe will preferentially hybridize with a nucleic acid or mRNA comprising the complementary sequence, allowing the identification and retrieval of the nucleic acids of the biological material that uniquely hybridize to the selected probe. Probes of more than 18 nucleotides can be used, e.g. probes of from about 25 nucleotides to about 100 nucleotides, from about 100 nucleotides to about 500 nucleotides, up to the entire coding region can be used, but 18 nucleotides generally represents sufficient sequence for unique identification.

The nucleic acids of the invention also include naturally occurring variants of the nucleotide sequences, e.g. degenerate variants, allelic variants, etc. Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25–30% base pair mismatches relative to the selected nucleic acid probe. In general, allelic variants contain 15–25% base pair mismatches, and can contain as few as even 5–15%, or 2–5%, or 1–2% base pair mismatches, as well as a single base-pair mismatch.

Homologs of the DAK are also provided in the present invention. Such homologs can be identified by any of a number of methods known to those skilled in the art. A fragment of the provided cDNA may be used as a hybridization probe against a cDNA library from the target organism of interest, where low stringency conditions are used. The probe may be a large fragment, or one or more short degenerate primers.

The invention also encompasses homologs corresponding to the nucleic acids of SEQ ID NO:1, NO:3, or NO:13, where the source of homologous genes can be any related species within the same genus or group. Within a group, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared.

The term "DAK polynucleotide" encompasses polynucleotides which encode a DAK polypeptide, a fragment thereof, or a fusion protein thereof, as described above. Thus, in some embodiments, a DAK polynucleotide comprises a nucleotide sequence encoding a polypeptide comprising at least about 6, 10, 15, 20, 25, 50, 75, 100, 200, 300, 400, 500, 600, 700, 800, or 830 contiguous amino acids of the sequence set forth in SEQ ID NO:2. In other embodiments, a DAK polynucleotide comprises a nucleotide sequence encoding a polypeptide comprising at least about 6, 10, 15, 20, 25, 50, 75, 100, 200, 300, 400, 500, 600, 700, 800, 900, or 1000 contiguous amino acids of the sequence set forth in SEQ ID NO:4. In other embodiments, a DAK polynucleotide comprises a nucleotide sequence encoding the entire polypeptide having the amino acid sequence set forth in SEQ ID NO:2 or NO:4. In still other embodiments, a DAK polynucleotide comprises a nucleotide sequence which encodes a polypeptide comprising an amino acid sequence sharing at least about 70%, more preferably at least about 80%, even more preferably at least about 90% or more amino acid sequence identity with the sequence depicted in SEQ ID NO:2 or NO:4.

Also encompassed by the invention are polynucleotides complementary to a DAK polynucleotide, as defined above. Further encompassed are human sAC antisense polynucleotides and ribozymes. Various derivatives of the antisense sequence may be prepared, where the phosphates may be modified, where oxygens may be substituted with sulfur and nitrogen, the sugars may be modified, and the like. The antisense sequences may be used by themselves or in conjunction with various toxic moieties, such as metal chelates, sensitizers, ribozymes, and the like. Antisense and/or ribozyme sequences may be used to inhibit spermatogenesis. Antisense polynucleotides, and methods of using such, are described in numerous publications, including, e.g., "Antisense Technology: A Practical Approach" Lichtenstein and Nellen, eds. (1997) IRL Press.

Antisense molecules can be used to down-regulate expression of DAK genes in cells. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise two or more different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra.) Preferred oligonucleotides are chemically modified from the native phosphodiester structure, in order to increase their intracellular stability and binding affinity. Such modifications have been previously discussed with respect to the use of probes.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

A DAK polynucleotide may be a DAK cDNA. The term "cDNA" as used herein is intended to include all nucleic acids that share the arrangement of sequence elements found in native mature mRNA species, where sequence elements are exons and 3" and 5" non-coding regions. Normally mRNA species have contiguous exons, with the intervening introns, when present, removed by nuclear RNA splicing, to create a continuous open reading frame encoding the protein protein Also encompassed by the term "DAK polynucleotide" are DAK genomic sequences. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, up to about 6 kb, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where DAK is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol. Med.* 1: 194–205; Mortlock et al. (1996) *Genome Res.* 6:327–33; and Joulin and Richard-Foy (1995) *Eur. J. Biochem.* 232:620–626.

The regulatory sequences may be used to identify cis acting sequences required for transcriptional or translational regulation of expression, especially in different tissues or stages of development, and to identify cis acting sequences and trans-acting factors that regulate or mediate expression. Such transcription or translational control regions may be operably linked to one of the subject genes in order to promote expression of wild type or altered DAK protein, or other proteins of interest in cultured cells, or in embryonic, fetal or adult tissues, and for gene therapy.

The nucleic acid compositions of the subject invention may encode all or a part of the DAK polypeptides of the invention. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 18 nt, usually at least 25 nt or 50 nt, and may be at least about 100 nt. Such small DNA fragments are useful as primers for PCR, hybridization screening probes, etc. Larger DNA fragments, i.e. greater than 500 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The polynucleotides of the invention are isolated and obtained in substantial purity, generally as other than an intact chromosome. Usually, the DNA will be obtained substantially free of nucleic acid sequences other than a DAK polynucleotide, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by reverse transcriptase-polymerase chain reaction (RT-PCR), using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of DAK gene expression (i.e., at least transcription) in the sample.

The sequence of genes encoding DAK, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. One of skill in the art will recognize that, in general, such mutations will occur outside of regions that affect DAK kinase activity. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993) *Biotechniques* 14:22; Barany (1985) *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., Molecular Cloning: A Laboratory Manual, CSH Press 1989, pp. 15.3–15.108; Weiner, et al., (1993) *Gene* 126:35–41; Sayers et al., (1992) *Biotechniques* 13:592–6; Jones, et al., (1992) *Biotechniques* 12:528–30; Barton et al., (1990) *Nucleic Acids Res* 18:7349–55; Marotti, et al., (1989) *Gene Anal. Tech.* 6:67–70; and Zhu (1989) *Anal Biochem* 177:120–4. Such mutated genes may be used to study structure-function relationships of DAK polypeptides, or to alter properties of the protein that affect its function or regulation.

DAK polynucleotides can be prepared in a number of different ways. For example, the nucleic acid may be synthesized using solid phase synthesis techniques, as are known in the art. Oligonucleotide synthesis is also described in Edge, et al., (1981) *Nature* 292:756; Duckworth et al., (1981) *Nucleic Acids Res* 9:1691 and Beaucage, et al., (1981) *Tet. Letts* 22: 1859. Following preparation of the nucleic acid, the nucleic acid is then ligated to other members of the expression system to produce an expression cassette or system comprising a nucleic acid encoding the subject product in operational combination with transcriptional initiation and termination regions, which provide for expression of the nucleic acid into the subject polypeptide products under suitable conditions.

Recombinant Vectors of the Invention

The present invention further provides recombinant vectors ("constructs") comprising DAK polynucleotides of the invention. Recombinant vectors are useful for propagation of the subject DAK polynucleotides (cloning vectors). They are also useful for effecting expression of a DAK polynucleotide in a cell (expression vectors). Some vectors accomplish both cloning and expression functions. The choice of appropriate vector is well within the skill of the art. Many such vectors are available commercially.

A variety of host-vector systems may be utilized to propagate and/or express the DAK polynucleotides of the invention. Such host-vector systems represent vehicles by which coding sequences of interest may be produced and subsequently purified, and also represent cells that may, when transformed or transfected with the appropriate nucleotide coding sequences, produce DAK polypeptides of the invention. These include, but are not limited to, microorganisms (e.g., *E. coli, B. subtilis*) transformed with recombinant bacteriophage vectors, plasmid DNA, or cosmid DNA vectors comprising DAK polynucleotides; yeast (e.g., *Saccharomyces, Pichia*) transformed with recombinant yeast vectors comprising DAK polynucleotides); insect cell systems (e.g., *Spodoptera frugiperda*) infected with recombinant virus expression vectors (e.g., baculovirus vectors, many of which are commercially available, including, for example, pBacPAK8, and BacPAK6) comprising DAK polynucleotides; plant cell systems; or mammalian cell systems (e.g., COS, CHO, BHK, 293, 3T3) harboring recombinant vectors comprising mammalian promoters (e.g., metallothionein promoter) or promoters from viruses which replicate in mammalian cells (e.g., adenovirus late promoter; vaccinia virus promoter, and the like). Examples of prokaryotic cloning vectors which find use in propagating DAK polynucleotides of the invention are pBR322, M13 vectors, pUC18, pcDNA, and pUC19. Prokaryotic expression vectors which find use in expressing DAK polypeptides in prokaryotic cells include pTrc99A, pK223-3, pEZZ18, pRIT2T, and pMC1871. Eukaryotic expression vectors which find use in expressing DAK polynucleotides and DAK polypeptides in eukaryotic cells include commercially available vectors such as pSVK3, pSVL, pMSG, pCH110, pMAMneo, pMAMneo-LUC, pPUR, and the like.

Generally, a bacterial host will be transformed to contain the expression system using a vector. A variety of vectors may be employed so long as they introduce the expression system into the host in a manner whereby the product encoded by the expression system can be expressed. Thus, the vector could be one that is capable homologously recombining with a region of the host chromosome such that the expression system becomes integrated into the host chromosome such that expression of the protein encoded thereby can occur. See Thomas and Capecchi (1987) *Cell* 51:503–512; as well as U.S. Pat. Nos. 5,631,153; 5,627,059; 5,487,992 and 5,464,764, the disclosure of which is herein incorporated by reference.

Generally, the expression cassette will be a plasmid that provides for expression of the encoded DAK polypeptide under appropriate conditions, i.e. in a host cell. The expression vector will typically comprise a replicon, which includes the origin of replication and its associated cis-acting control elements. Representative replicons that may be present on the expression vector include: pMB1, p15A, pSC101 and ColE1. Expression vectors generally have convenient restriction sites located near the promoter sequence to provide for the insertion of nucleic acid sequences encoding heterologous proteins. In addition, the expression vector will also typically comprise a marker which provides for detection of the clones that have been transformed with the vector. A variety of markers are known and may be present on the vector, where such markers include those that confer antibiotic resistance, e.g. resistance to ampicillin, tetracycline, chloramphenicol, kanamycin (neomycin), markers that provide for histochemical detection, etc. Specific vectors that may find use in the subject methods include: pBR322, pUC18, pUC19, pcDNA, and the like. Introduction of the nucleic acid encoding the subject peptidic product into the expression vector is accomplished by cutting the expression vector and inserting the polynucleotide encoding the desired product.

Following preparation of the expression vector comprising the nucleic acid, the expression vector will be introduced into an appropriate host cell for production of the DAK polypeptide, i.e. a host cell will be transformed with the expression vector. Transformation of host cells may be accomplished in any convenient manner, where two representative means of transformation are treatment with divalent cation transformation compositions and electrotransformation. In transformation through divalent cation treatment, the host cells are typically incubated with the one or more divalent cations, e.g. $CaCl_2$, which serves to make the host cell permeable to the vector DNA. See Cohen et al. (1972) Proc. Nat'l. Acad. Sci. USA 69:2110. Other agents with which the host cells may also be incubated include DMSO, reducing agents, hexaminecobalt and the like, where such agents serve to improve the efficiency of transformation. In electrotransformation (also known as transformation by electroporation) host cells are subject to an electrical pulse in the presence of the vector in a manner sufficient for the vector to enter the host cells. See Dower et al. (1988) Nucleic Acids Research 16:6127.

A variety of host cells are suitable and may be used in the production of the DAK polypeptides, where such host cells may be bacterial cells, yeast cells, or other cells, such as plant cells (see Depicker (1982) J. Mol. Appl. Gen. 1:561, where the host cell will generally be bacterial, e.g. E. coli, B. subtilis, where an E. coli strain is often the host cell of choice; or mammalian, e.g., COS, CHO, 3T3, and the like. E. coli strains that may be used include DH1, DH5, MM294, LE392, MC1061 and JM109.

Following transformation, bacterial host cells are screened for incorporation of the expression vector. Transformed colonies, e.g. host cells harboring the expression vector with the nucleic acid encoding the DAK polypeptide are identified, and then grown up in large quantity. Where appropriate, agents that induce expression of the DAK polypeptide are contacted with the host cell, e.g. isopropylthiogalactoside (IPTG).

Following colony growth, the expressed product will be harvested and purified for subsequent use. Typically, purification of the product involves disruption of the host cell, inactivation and removal of the native host proteins and precipitation of the nucleic acids. The product is separated from the other host cell constituents using one or more of a number of separation techniques known to those of skill in the art, e.g. centrifugation, dialysis, gel filtration chromatography, ion exchange chromatography, and the like. See Guide to Protein Purification (Murray P. Deutscher ed., Harcourt Brace & Co.)(1990). Using these protein purification techniques, isolated product may be prepared, where by isolated is meant a composition that is at least about 95% by weight peptidic product, usually at least about 98% by weight peptidic product and more usually at least about 99% by weight product, when the composition is dehydrated, e.g. lyophilized.

The subject nucleic acid molecules are generally propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence.

Other vectors are suitable for expression in cells in culture. These vectors will generally include regulatory sequences ("control sequences" or "control regions") which are necessary to effect the expression of a DAK polynucleotide to which they are operably linked. Still other vectors are suitable for transfer and expression in cells in a whole organism or person.

The DAK polynucleotides and polypeptides of the present invention can be introduced into a cell by a gene delivery vehicle. Generally, gene delivery vehicles can encode either polypeptides or polynucleotides, such as antisense or ribozymes. The gene delivery vehicle may be of viral or non-viral origin (see generally, Jolly, Cancer Gene Therapy (1994) 1:51–64; Kimura, Human Gene Therapy (1994) 5:845–852; Connelly, Human Gene Therapy (1995) 1:185–193; and Kaplitt, Nature Genetics (1994) 6:148–153). Gene therapy vehicles for delivery of constructs including a coding sequence of a polynucleotide of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 415 731; WO 90/07936; WO 94/03622; WO 93/25698; WO 93/25234; U.S. Pat. No. 5,219,740; WO 93/11230; WO 93/10218; Vile and Hart, Cancer Res. (1993) 53:3860–3864; Vile and Hart, Cancer Res. (1993) 53:962–967; Ram et al., Cancer Res. (1993) 53:83–88; Takamiya et al., J. Neurosci. Res. (1992) 33:493–503; Baba et al., J. Neurosurg. (1993) 79:729–735; U.S. Pat. No. 4,777,127; GB Patent No. 2,200,651; and EP 345 242.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

Gene delivery vehicles of the present invention can also employ parvovirus such as adeno-associated virus (AAV) vectors. Representative examples include the AAV vectors disclosed by Srivastava in WO 93/09239, Samulski et al., J. Vir. (1989) 63:3822–3828; Mendelson et al., Virol. (1988) 166:154–165; and Flotte et al., PNAS (1993) 90:10613–10617.

Also of interest are adenoviral vectors, e.g., those described by Berkner, Biotechniques (1988) 6:616–627; Rosenfeld et al.(1991) Science 252:431–434; WO 93/19191; Kolls et al. (1994) Proc. Natl. Acad. Sci. USA 91:215–219; Kass-Eisler et al. (1993) Proc. Natl. Acad. Sci. USA 90:11498–11502; WO 94/12649, WO 93/03769; WO 93/19191; WO 94/28938; WO 95/11984 and WO 95/00655.

Other gene delivery vehicles and methods may be employed, including polycationic condensed DNA linked or unlinked to killed adenovirus alone, for example Curiel (1992) Hum. Gene Ther. 3:147–154; ligand linked DNA, for example see Wu (1989) J. Biol. Chem. 264: 16985–16987; eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip (1994) Mol. Cell Biol. 14:2411–2418, and in Woffendin (1994) Proc. Natl. Acad. Sci. 91:1581–1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 524 968.

Further non-viral delivery suitable for use includes mechanical delivery systems such as the approach described in Woffendin et al.(1994) *Proc. Nail. Acad. Sci. USA* 91:11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

Host Cells of the Invention

The present invention further provides host cells, which may be isolated host cells, comprising DAK polynucleotides of the invention. Suitable host cells include prokaryotes such as *E. coli, B. subtilis*, eukaryotes, including insect cells in combination with baculovirus vectors, yeast cells, such as *Saccharomyces cerevisiae*, or cells of a higher organism such as vertebrates, including amphibians (e.g., *Xenopus laevis* oocytes), and mammals, particularly mammals, e.g. COS cells, CHO cells, 293 cells, 3T3 cells, and the like, may be used as the expression host cells. Host cells can be used for the purposes of propagating a DAK polynucleotide, for production of a DAK polypeptide, or in cell-based methods for identifying agents which modulate a level of DAK mRNA and/or protein and/or enzyme activity in a cell.

The subject nucleic acids can be used to generate transgenic animals or site specific gene modifications in cell lines. The modified cells or animals are useful in the study of DAK function and regulation. For example, a series of small deletions or substitutions may be made in the DAK gene to determine the role of different coding regions in controlling cell proliferation, signal transduction, Dsh binding, etc.

DNA constructs for homologous recombination will comprise at least a portion of the DAK gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the sAC gene and males and females having the modification are mated to produce homozygous progeny. The transgenic animals may be any non-human mammal, such as laboratory animals, domestic animals, etc. The transgenic animals may be used to determine the effect of a candidate drug on controlling unwanted cell proliferation, e.g., a reduction in cancer cell growth, in an in vivo environment.

Antibodies Specific for DAK Polypeptides

The present invention provides antibodies, which may be isolated antibodies, specific for DAK polypeptides of the invention. Such antibodies are useful, for example, in methods of detecting the presence of a DAK polypeptide in a biological sample, and in methods of isolating a DAK polypeptide from a biological sample.

The DAK polypeptides of the invention are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a DAK polypeptide. As described in Example 6, polyclonal antibodies were raised to a fragment of DAK (amino acids 469–832). This antiserum specifically immunoprecipitated DAK polypeptides from *Drosophila* embryos and Clone-8 cells, while pre-immune serum did not.

In some embodiments, an antibody of the invention inhibits DAK-Dsh binding. An antibody of the invention which inhibits DAK-Dsh binding is one that specifically inhibits binding of a DAK polypeptide to a Dsh polypeptide, when compared to a suitable control. An antibody which "specifically inhibits" DAK-Dsh binding is one that does not substantially inhibit interaction of other protein-protein binding at the concentration required to achieve 50% inhibition of DAK-Dsh binding. Antibody inhibition of DAK-Dsh binding can be measured by any suitable assay, including, but not limited to an enzyme-linked immunosorbent assay (ELISA), a radioimmunoassay (RIA), and the like. Typically, these assays are carried out in the presence of various concentrations of antibody. A suitable control is a sample that contains the DAK and Dsh proteins, and no antibody, or, alternatively, the sample contains DAK and Dsh proteins and a non-specific antibody, e.g., an antibody specific for albumin, or an anti-idiotype antibody.

Antibodies may be raised to the wild-type or variant forms. Antibodies may be raised to isolated peptides corresponding to Dsh-binding domain(s) of native DAK, to isolated peptide corresponding to solvent-accessible portions of native DAK, or to isolated peptides corresponding to a non-Dsh-binding domain of DAK.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in $E.\ coli$, and the heavy and light chains mixed to further enhance the affinity of the antibody. Alternatives to in vivo immunization as a method of raising antibodies include binding to phage display libraries, usually in conjunction with in vitro affinity maturation.

Substances which Inhibit DAK-DSH Binding

The invention further provides substances which specifically inhibit DAK-Dsh binding, as well as compositions comprising the substances. Such substances find use in one or more of the following: (1) reducing a level of phosphorylated Dsh in a eukaryotic cell; (2) reducing a level of β-catenin in the nucleus of a eukaryotic cell; (3) reducing cell proliferation.

Substances which inhibit DAK-Dsh binding include, but are not limited to, a peptide fragment corresponding to a DAK kinase domain; a peptide fragment corresponding to a DAK-binding domain of a Dsh polypeptide; an antibody specific for a DAK kinase domain; and an antibody specific for a DAK-binding domain of a Dsh polypeptide. Preferably, an inhibitor of DAK-Dsh binding can enter a eukaryotic cell. Inhibitors may be coupled with, or be in a composition which comprises, a substance or moiety that facilitates entry into a eukaryotic cell.

In some embodiments, the inhibitor is a peptide fragment corresponding to an amino acid sequence of a portion of DAK that mediates binding to Dsh, or a portion of Dsh that mediates binding to DAK. "Corresponding to" intends that the peptide fragment may have an amino acid sequence identical to an amino acid sequence of DAK that mediates binding to Dsh, or an amino acid sequence of Dsh that mediates binding to DAK. The amino acid sequence that mediates binding may comprise, but need not comprise, contiguous amino acids of DAK or Dsh. Furthermore, a peptide fragment corresponding to a portion of DAK that mediates binding to Dsh, or a portion of Dsh that mediates binding to DAK need not be identical in amino acid sequence to that portion. Those of skill in the art will recognize that modifications may be made in the sequence, which modifications do not substantially affect inhibition of DAK-Dsh binding. Furthermore, certain modifications in the sequence may actually increase inhibition of DAK-Dsh binding. Suitable peptide fragment lengths will be about 8 amino acids to about 100 amino acids, from about 10 amino acids to about 50 amino acids, from about 20 amino acids to about 40 amino acids. The peptides may be further modified by acylation, glycosylation, and the like. The peptides may also be part of a fusion protein, where the fusion partner may be selected from a polypeptide that confers stability to the peptide, facilitates entry into the cell, facilitates detection or purification, and the like.

In some embodiments, the peptide has an amino acid sequence as set forth in any one of SEQ ID NOS:5–9. The peptide may be a variant of any one of these sequences, as long as DAK-Dsh binding is inhibited. Also included are polynucleotides comprising sequences encoding any of the foregoing peptides. In some embodiments, the substance is a peptide such as D3DM5 (SEQ ID NO:8), a polypeptide comprising an amino acid sequence as set forth in SEQ ID NO:8, or a fusion protein comprising an amino acid sequence as set forth in SEQ ID NO:8, including, but not limited to, a GST fusion protein as described in Example 8. In other embodiments, the substance is a polynucleotide encoding a peptide such as D3DM5 (SEQ ID NO:8), a polypeptide comprising an amino acid sequence as set forth in SEQ ID NO:8, a fusion protein comprising an amino acid sequence as set forth in SEQ ID NO:8. Synthetic peptides (peptoids) are also of interest, particularly synthetic peptides based on the sequence of D3DM5. Peptoid compounds and methods for their preparation are described in WO 91/19735. In other embodiments, the substance is an antibody which specifically inhibits DAK-Dsh binding.

Any method of detecting DAK-Dsh binding can be used to determine whether a substance inhibits DAK-Dsh binding, including the assay methods described below, and in the Examples.

Compositions of the Invention

The present invention further provides compositions comprising the polypeptides, polynucleotides, recombinant vectors, host cells, DAK-Dsh binding inhibitors, and antibodies of the invention. These compositions may include a buffer, which is selected according to the desired use of the polypeptide, polynucleotide, recombinant vector, host cell, DAK-Dsh binding inhibitor, or antibody, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19th Ed. (1995) Mack Publishing Co.

Methods Using the Polypeptides and Polynucleotides of the Invention

The present invention provides a variety of detection methods, which methods are useful in diagnostic assays. Also provided are a variety of screening assays, which assays are useful for identifying agents which affect DAK activity (e.g., kinase activity and/or Dsh-binding) and/or DAK mRNA and/or DAK polypeptide levels.

Detection Methods

Detection methods of the present invention include methods for detecting DAK polypeptide in a biological sample, methods for detecting DAK mRNA in a biological sample, and methods for detecting DAK kinase activity in a biological sample.

The detection methods can be provided as part of a kit. Thus, the invention further provides kits for detecting the presence and/or a level of DAK polypeptide or DAK polynucleotides in a biological sample. Procedures using these kits can be performed by clinical laboratories, experimental laboratories, medical practioners, or private individuals. The kits of the invention for detecting a DAK polypeptide comprise a moiety that specifically binds DAK, including, but not limited to, a DAK-specific antibody, and a Dsh polypeptide. The kits of the invention for detecting a DAK polynucleotide comprise a moiety that specifically hybridizes to a DAK polynucleotide. The kit may optionally provide additional components that are useful in the procedure, including, but not limited to, buffers, developing reagents, labels, reacting surfaces, means for detections, control samples, standards, instructions, and interpretive information.

Methods of Detecting a DAK Polypeptide in a Biological Sample

The present invention further provides methods for detecting the presence and/or measuring a level of a DAK polypeptide in a biological sample, using a DAK-specific antibody. The methods generally comprise:

a) contacting the sample with an antibody specific for a DAK polypeptide; and b) detecting binding between the antibody and molecules of the sample.

Detection of specific binding of the DAK-specific antibody, when compared to a suitable control, is an indication that DAK polypeptides are present in the sample. Suitable controls include a sample known not to contain a DAK polypeptide; and a sample contacted with an antibody not specific for DAK, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the DAK-specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The antibody may be attached (coupled) to an insoluble support, such as a polystyrene plate or a bead. Indirect labels include second antibodies specific for DAK-specific antibodies, wherein the second antibody is labeled as described above; and members of specific binding pairs, e.g., biotin-avidin, and the like. The biological sample may be brought into contact with an immobilized on a solid support or carrier, such as nitrocellulose, that is capable of immobilizing cells, cell particles, or soluble proteins. The support may then be washed with suitable buffers, followed by contacting with a detectably-labeled DAK-specific antibody. Detection methods are known in the art and will be chosen as appropriate to the signal emitted by the detectable label. Detection is generally accomplished in comparison to suitable controls, and to appropriate standards.

The present invention further provides methods for detecting the presence and/or measuring a level of a DAK polypeptide in a biological sample. The methods generally comprise:

a) contacting the sample with a Dsh protein specific for a DAK polypeptide; and b) detecting binding between the Dsh protein and molecules of the sample.

Detection of specific binding of the Dsh polypeptide is an indication that DAK polypeptides are present in the sample. Methods for detecting binding between a DAK polypeptide and a Dsh polypeptide are known in the art and include immunoprecipitation of DAK-Dsh complexes using an antibody specific for DAK or Dsh, as long as the antibody does not disrupt DAK-Dsh binding. Alternatively, the Dsh polypeptide used may be a fusion protein which provides for specific immunoprecipitation of the fusion partner, an enzymatic detection, a fluorescent signal (e.g., a green fluorescent protein). The Dsh polypeptide can be labeled with any detectable label, as described below. The Dsh polypeptide can be attached, directly or through a linker, to an insoluble support (e.g., polystyrene beads, magnetic beads, and the like), thereby providing a means for separating DAK-Dsh complexes from the biological sample, and subsequently detecting the presence of and/or measuring the amount (level) of DAK polypeptide.

Methods of Detecting a DAK mRNA in a Biological Sample

The present invention further provides methods for detecting the presence of DAK mRNA in a biological sample. The methods can be used, for example, to assess whether a test compound affects DAK gene expression, directly or indirectly.

The methods generally comprise:

a) contacting the sample with a DAK polynucleotide of the invention under conditions which allow hybridization; and b) detecting hybridization, if any.

Detection of hybridization, when compared to a suitable control, is an indication of the presence in the sample of a DAK polynucleotide. Appropriate controls include, for example, a sample which is known not to contain DAK mRNA, and use of a labelled polynucleotide of the same "sense" as a DAK mRNA. Conditions which allow hybridization are known in the art, and have been described in more detail above. Detection can be accomplished by any known method, including, but not limited to, in situ hybridization, PCR, RT-PCR, and "Northern" or RNA blotting, or combinations of such techniques, using a suitably labelled DAK polynucleotide. A variety of labels and labelling methods for polynucleotides are known in the art and can be used in the assay methods of the invention. Specific hybridization can be determined by comparison to appropriate controls.

Methods using PCR amplification can be performed on the DNA from a single cell, although it is convenient to use at least about $10^5$ cells. The use of the polymerase chain reaction is described in Saiki et al. (1985) *Science* 239:487, and a review of current techniques may be found in Sambrook, et al. *Molecular Cloning: A Laboratory Manual*, CSH Press 1989, pp. 14.2–14.33. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Methods for Detecting a DAK Kinase Activity in a Biological Sample

The present invention provides a method for detecting a DAK kinase activity in a biological sample. The method generally comprises:

a) contacting the sample with a Dishevelled protein; and b) detecting phosphorylation of the Dishevelled protein.

Detection of Dsh phosphorylation, when compared to a suitable control, is an indication of DAK kinase in the sample. Suitable negative controls include a sample containing a protein which is known not to be phosphorylated by DAK; and a sample containing a fragment of the Dsh protein which is not phosphorylated by DAK, examples of which are provided in FIG. 2. Detecting phosphorylation of a Dsh protein can be accomplished as described herein, using whole Dsh protein, or, alternatively, a fragment of the Dsh protein, including, but not limited to, the DM5 region of Dsh, and a fusion protein comprising the DM5 region of Dsh fused to a heterologous peptide. Any known method of detecting phosphorylation of a protein, or peptide fragment thereof, can be used in these methods. Phosphorylation of the Dsh protein indicates that DAK kinase activity is present in the sample. Typically, a level of phosphorylation in the test sample (i.e., the sample comprising the biological sample and the Dsh protein) is compared to the level of phosphorylation in a control sample.

The method can also be used to measure a level of DAK kinase activity in a biological sample. In these methods, a series of positive controls is provided, with DAK at various, known concentrations, and a fixed amount of Dsh, thereby generating a standard curve. In this manner, a level of Dsh phosphorylation can be compared to the standard curve, and the amount of DAK kinase activity determined.

The method is useful, for example, in assessing the efficacy of an anti-cancer treatment, monitoring the status of a cancer in a subject.

Screening Assays

The present invention provides screening methods for identifying agents which modulate DAK kinase activity, methods for identifying agents which modulate DAK-Dsh interaction, methods for identifying agents which modulate a level of DAK polypeptide in a cell, and methods for identifying agents which modulate a level of DAK mRNA in a cell.

As used herein, the term "modulate" encompasses "increase" and "decrease". Of particular interest are agents which inhibit DAK kinase activity, and/or which inhibit DAK-Dsh interaction, and/or which reduce a level of DAK polypeptide in a cell, and/or which reduce a level of DAK mRNA in a cell. Such agents are of interest as candidates for treating cancers, including, but not limited to, colon cancer, melanoma, breast cancer, prostate cancer, ovarian cancer, endometrial cancer, and hepatocellular carcinoma. Such agents may decrease β-catenin accumulation in the nucleus of a eukaryotic cell, thereby reducing undesired cell proliferation.

The terms "agent", "substance" and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and typically include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

Methods for Identifying Agents that Modulate DAK Kinase Activity

The present invention provides methods of identifying agents which modulate a kinase activity of a DAK polypeptide of the invention. The term "modulate" encompasses an increase or a decrease in the measured DAK kinase activity when compared to a suitable control.

The method generally comprises:

a) contacting a substance to be tested with a sample containing a DAK polypeptide; and b) assaying a kinase activity of the DAK polypeptide in the presence of the substance.

An increase or a decrease in kinase activity in comparison to DAK kinase activity in a suitable control (e.g., a sample comprising a DAK polypeptide in the absence of the substance being tested) is an indication that the substance modulates a kinase activity of the DAK.

An "agent which modulates a kinase activity of a DAK polypeptide", as used herein, describes any molecule, e.g. synthetic or natural organic or inorganic compound, protein or pharmaceutical, with the capability of altering a kinase activity of a DAK polypeptide, as described herein. Generally a plurality of assay mixtures are run in parallel with different agent concentrations to obtain a differential response to the various concentrations. Typically, one of these concentrations serves as a negative control, i.e. at zero concentration or below the level of detection. Kinase activity can be measured as described in Example 1, or using any kinase assay known in the art.

An agent which modulates a kinase activity of a DAK polypeptide increases or decreases the activity at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control.

Agents which increase or decrease a kinase activity of a DAK polypeptide to the desired extent may be selected for further study, and assessed for cellular availability, cytotoxicity, biocompatibility, etc.

Of particular interest are agents which decrease a kinase activity of a DAK polypeptide. Maximal inhibition of kinase activity is not always necessary, or even desired, in every instance to achieve a therapeutic effect. Agents which decrease a kinase activity of a DAK polypeptide may find use in altering the Wnt/Wg signalling pathway and thus may be useful in treating cancers, including, but not limited to, colon cancer, melanoma, breast cancer, prostate cancer, ovarian cancer, endometrial cancer, and hepatocellular carcinoma. Such agents may decrease β-catenin accumulation in the nucleus of a eukaryotic cell, thereby reducing cell proliferation.

Methods for Identifying Agents that Modulate DAK-Dsh Binding

The present invention provides methods of identifying agents which modulate DAK-Dsh binding. The term "modulate" encompasses an increase or a decrease in the measured DAK-Dsh binding when compared to a suitable control.

The method generally comprises:

a) contacting a substance to be tested with a sample comprising a DAK polypeptide and a Dsh polypeptide; and b) measuring DAK-Dsh binding in the presence of the substance. An increase or a decrease in DAK-Dsh binding in comparison to DAK-Dsh binding in a suitable control is an indication that the substance modulates a kinase activity of the DAK. A suitable control comprises DAK and Dsh, but not the substance being tested. DAK-Dsh binding can be measured as described hereinabove.

Of particular interest are agents which decrease DAK-Dsh binding. An agent which inhibits DAK-Dsh binding decreases DAK-Dsh binding by at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control. An agent which inhibits DAK-Dsh binding can also be one that abrogates measurable DAK-Dsh binding completely.

Agents which increase or decrease a DAK-Dsh binding to the desired extent may be selected for further study, and assessed for cellular availability, cytotoxicity, biocompatibility, etc.

Of particular interest are agents which specifically decrease a DAK-Dsh binding. Maximal inhibition of binding activity is not always necessary, or even desired, in every instance to achieve a therapeutic effect. Agents which decrease DAK-Dsh binding may find use in altering the Wnt/Wg signalling pathway and thus may be useful in treating cancers, including, but not limited to, colon cancer, melanoma, breast cancer, prostate cancer, ovarian cancer, endometrial cancer, neuroblastoma, medulloblastoma, and hepatocellular carcinoma. Such agents may decrease β-catenin accumulation in the nucleus of a eukaryotic cell, thereby reducing cell proliferation.

Methods of Detecting Agents which Modulate a Level of DAK mRNA and/or DAK Polypeptide A wide variety of cell-based assays may be used for identifying agents which modulate levels of DAK mRNA, using, for example, a mammalian cell transformed with a construct comprising a DAK-encoding cDNA such that the cDNA is overexpressed, or, alternatively, a construct comprising a DAK promoter operably linked to a reporter gene.

Accordingly, the present invention provides a method for identifying an agent, particularly a biologically active agent, that modulates a level of DAK expression in a cell, the method comprising: combining a candidate agent to be tested with a cell comprising a nucleic acid which encodes a DAK polypeptide; and determining the effect of said agent on DAK expression. "Modulation" of DAK expression levels includes increasing the level and decreasing the level of DAK mRNA and/or DAK polypeptide encoded by the DAK polynucleotide when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of DAK mRNA and/or polypeptide following contacting the cell with a candidate agent being tested, compared to a control to which no agent is added, is an indication that the agent modulates DAK expression.

An agent being tested for its effect on DAK expression is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity are considered candidate agents.

The cells used in the assay are usually mammalian cells, including, but not limited to, rodent cells and human cells. The cells may be primary cell cultures or may be immortalized cell lines.

DAK mRNA and/or polypeptide whose levels are being measured can be encoded by an endogenous DAK polynucleotide, or the DAK polynucleotide can be one that is comprised within a recombinant vector and introduced into the cell, i.e., the DAK mRNA and/or polypeptide can be encoded by an exogenous DAK polynucleotide. For example, a recombinant vector may comprise an isolated DAK transcriptional regulatory sequence, such as a promoter sequence, operably linked to a reporter gene (e.g,. β-galactosidase, CAT, luciferase, or other gene that can be easily assayed for expression). In these embodiments, the method for identifying an agent that modulates a level of DAK expression in a cell, comprises: combining a candidate agent to be tested with a cell comprising a nucleic acid which comprises a DAK gene transcriptional regulatory element operably linked to a reporter gene; and determining the effect of said agent on reporter gene expression. A recombinant vector may comprise an isolated DAK transcriptional regulatory sequence, such as a promoter sequence, operably linked to sequences coding for a DAK polypeptide; or the transcriptional control sequences can be operably linked to coding sequences for a DAK fusion protein comprising DAK polypeptide fused to a polypeptide which facilitates detection. In these embodiments, the method comprises combining a candidate agent to be tested with a cell comprising a nucleic acid which comprises a DAK gene transcriptional regulatory element operably linked to a DAK polypeptide-coding sequence; and determining the effect of said agent on DAK expression, which determination can be carried out by measuring an amount of DAK mRNA, DAK polypeptide, or DAK fusion polypeptide produced by the cell.

Cell-based assays generally comprise the steps of contacting the cell with an agent to be tested, forming a test sample, and, after a suitable time, assessing the effect of the agent on DAK expression. A control sample comprises the same cell without the candidate agent added. DAK expression levels are measured in both the test sample and the control sample. A comparison is made between DAK expression level in the test sample and the control sample. DAK expression can be assessed using conventional assays. For example, when a mammalian cell line is transformed with a construct that results in expression of DAK, DAK mRNA levels can be detected and measured, as described above, or DAK polypeptide levels can be detected and measured, as described above. A suitable period of time for contacting the agent with the cell can be determined empirically, and is generally a time sufficient to allow entry of the agent into the cell and to allow the agent to have a measurable effect on DAK mRNA and/or polypeptide levels. Generally, a suitable time is between 10 minutes and 24 hours, more typically about 1–8 hours. Methods of measuring DAK mRNA levels are known in the art, several of which have been described above, and any of these methods can be used in the methods of the present invention to identify an agent which modulates DAK mRNA level in a cell, including, but not limited to, a PCR, such as a PCR employing detectably labeled oligonucleotide primers, and any of a variety of hybridization assays. Similarly, DAK polypeptide levels can be measured using any standard method, several of which have been described herein, including, but not limited to, an immunoassay such as ELISA, for example an ELISA employing a detectably labeled antibody specific for a DAK polypeptide.

Therapeutic Methods

The present invention provides methods of reducing levels of phosphorylated Dsh in a eukaryotic cell. The present invention further provides methods of reducing accumulation of, and/or a level of, β-catenin in the nucleus of a eukaryotic cell. The present invention further provides methods of reducing cell proliferation. The present invention provides methods of inhibiting tumor cell growth, comprising contacting a tumor cell with a compound that inhibits a DAK function.

The methods generally comprise contacting a eukaryotic cell with a substance which, after entering the cell, inhibits a kinase activity of a DAK polypeptide, and/or which inhibits-DAK-Dsh binding, and/or which reduces a level of DAK mRNA and/or DAK polypeptide in the eukaryotic cell. Generally, the cell is contacted with a composition comprising an effective amount of the substance. A reduction in the amount or activity of DAK polypeptides in the cell results in one or more of the following: (1) decreased levels of phosphorylated Dsh in the cell; (2) reduced accumulation of β-catenin in the nucleus of the cell; and (3) reduced cell proliferation. Reduction of β-catenin in the nucleus can be a result of a reduced rate of entry of β-catenin into the nucleus, and/or of a reduction in the levels of β-catenin in the cytosol and/or an increase in the proportion of β-catenin which is sent to a proteosome for degradation.

An effective amount of a substance which inhibits a kinase activity of a DAK polypeptide is an amount that decreases kinase activity of a DAK polypeptide by at least about 10%, more preferably at least about 15%, more preferably at least about 25%, more preferably at least about 50% or more, when compared to the kinase activity of the DAK polypeptide in the absence of the substance. An effective amount of a substance which inhibits DAK-Dsh binding is an amount that reduces DAK-Dsh binding by at least about 10%, more preferably at least about 15%, more preferably at least about 25%, more preferably at least about 50% or more, when compared to the level of DAK-Dsh binding in the absence of the substance. An effective amount of a substance which reduces a level of DAK mRNA in a cell is an amount that reduces DAK mRNA level by at least about 10%, more preferably at least about 15%, more preferably at least about 25%, more preferably at least about 50% or more, when compared to the level of DAK mRNA in the absence of the substance. An effective amount of a substance which reduces a level of DAK polypeptide in a cell is an amount that reduces a DAK polypeptide level by at least about 10%, more preferably at least about 15%, more preferably at least about 25%, more preferably at least about 50% or more, when compared to the level of DAK polypeptide in the absence of the substance.

Whether a substance is effective in reducing a level of phosphorylated Dsh in a eukaryotic cell can readily be determined using any known assay. As a non-limiting example of how phosphorylated Dsh levels can be measured, cells are contacted with a substance, and after a suitable time (e.g., 0.1 hour to 1.0 hour), cells are lysed, the lysate is optionally cleared by centrifugation to remove membranes and other particulate matter, and the lysate is contacted with Dsh-specific antibody, thereby effectively isolating the Dsh polypeptide from the lysate. The Dsh polypeptide can then be further analyzed for presence and/or number of phosphate groups, using, e.g., an antibody specific for phosphate groups. Alternatively, the cell can be first be labeled with $[\gamma\text{-}^{32}P]$-ATP, and, after contacting the cell with the substance, Dsh polypeptides can be isolated as described, and the amount of radioactivity incorporated into the Dsh polypeptide determined by standard means.

Whether a substance is effective in reducing accumulation of and/or a level of β-catenin in the nucleus of a eukaryotic cell can be readily determined using any known assay. As one non-limiting example, one may use a LEF promoter-reporter construct, as described in Examples 8 and 9, in a eukaryotic cell as an indicator of the level of β-catenin in the nucleus of the cell.

The substance may be any of the inhibitors of DAK-Dsh binding, as described above. Also of interest are antisense and ribozyme molecules which specifically reduce DAK mRNA production and/or stability, as described above. Of further interest are any substances which inhibits a kinase activity of a DAK polypeptide, and/or which inhibits DAK-Dsh binding, and/or which reduces a level of DAK mRNA and/or DAK polypeptide in the eukaryotic cell identified by any of the screening methods described above.

In some embodiments, the method comprises administering to an individual an effective amount of a substance which inhibits a kinase activity of a DAK polypeptide, and/or which inhibits DAK-Dsh binding, and/or which reduces a level of DAK mRNA and/or DAK polypeptide in the eukaryotic cell.

Cells which are targets for the methods of the present invention are those which are proliferating due to accumulation of β-catenin in the nucleus, and include, but are not limited to, cancerous cells of colon cancer, melanoma, breast cancer, prostate cancer, ovarian cancer, endometrial cancer, and hepatocellular carcinoma. Individual considered as candidates for treatment include those having cancer, including, but not limited to, colon cancer, melanoma, breast cancer, prostate cancer, ovarian cancer, endometrial cancer, and hepatocellular carcinoma. The methods decrease β-catenin accumulation in the nucleus of a eukaryotic cell, thereby reducing cell proliferation.

Whether tumor cell growth is inhibited or reduced can be assessed by any means known in the art, including, but not limited to, measuring tumor size; determining whether tumor cells are proliferating, e.g., by using a $^3$H-incorporation assay; and/or counting tumor cells.

The compounds having the desired pharmacological activity may be administered in a physiologically acceptable carrier to a host for treatment one or more of the cancers noted above. The compounds may also be used to reduce or inhibit DAK function, either directly, e.g., by inhibiting DAK kinase activity, or indirectly, e.g., by reducing the amount of DAK mRNA and/or polypeptide synthesized. The therapeutic agents may be administered in a variety of ways, orally, topically, parenterally e.g. subcutaneously, intraperitoneally, by viral infection, intravascularly, etc. Inhalation treatments may also be of interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celcius, and pressure is at or near atmospheric.

Example 1

Identification of a Dishevelled Associated Kinase, DAK

Dsh is progressively phosphorylated during the stages of embryo development known to require Wg. Dsh is not phosphorylated in newly hatched embryos (0–2 hrs). Two hours after hatching, when Wg expression was reported to become readily detectable and the Wg signal pathway began to function (Rijsewijk et al. (1987) Cell 50:649–657), Dsh became phosphorylated as shown by the appearance of slower migrating bands on the gel. The phosphorylation gradually increased and peaked at around 14–20 hours.

To find a kinase associated with Dsh, endogenous Dsh was immunoprecipitated from embryos and Clone-8 cells, which are derived from imaginal discs and respond to Wg in culture (Yanagawa et al. (1995) Genes Dev. 9:1087–1097), and analyzed by in vitro kinase assays, using the following methods.

Preparation of Lysates

Washed and dechorionated embryos were Dounce homogenized in Buffer A (50 mM HEPES (pH 7.6) 100 mM NaCl, 0.5% nonionic detergent Nonidet P-40 (NP-40), 10 mM NaF, 5 mM NaPPi, 1.5 mM $MgCl_2$, 1 mM EGTA, 10% glycerol, and 1 mM benzamidine) containing a protease inhibitor cocktail (PIC) (1 mM PMSF, 1 µg/ml aprotinin, 1 µg/ml leupeptin, 1 µg/ml pepstatin, 1 µg/ml chymostatin). The crude lysates were centrifuged at 3000×g for 10 minutes at 4° C. and again at 10,000×g for 15 minutes at 4° C. The supernatants were collected. The Clone-8 cells were grown as described (van Leeuwen et al. (1994) Nature 368:342–344). Active grown Clone-8 cells were harvested and lysed in Buffer A with PIC for 15 minutes on ice. The lysates were centrifuged at 3000×g for 10 minutes at 4° C. and then at 10,000×g for 15 minutes at 4° C. The supernatants were collected.

Immunoprecipitation and GST Pull-down

Lysates in buffer A with PIC were incubated with anti-Dsh or anti-DAK antibodies for 2–4 hours at 4° C. The immune complexes were collected by incubation with protein-A beads for 2 hours at 4° C., followed by centrifugation. The immunoprecipitates were then washed three times for 5–10 minutes each with Buffer A and subjected to SDS-PAGE or in vitro kinase assay. For precipitation by GST fusion proteins containing various regions of Dsh, lysates in buffer A with PIC were incubated for 2–4 hours at 4° C. with fusion proteins immobilized on glutathione agarose beads, followed by brief centrifugation. The glutathione beads were then washed three time for 5–10 minutes each with Buffer A and subjected to in vitro kinase assay, as described below.

Immunoprecipitated Dsh was phosphorylated in this assay. To show that recombinant Dsh could be used to isolate the kinase, lysates prepared from embryos and Clone-8 cells were mixed with immobilized GST-fusion proteins containing various regions of Dsh, washed extensively to removed unbound proteins, and analyzed by in vitro kinase assay. By this method, kinase activity was precipitated by a GST-fusion protein containing the middle region of Dsh from either embryos or Clone-8 cells.

In Vitro Kinase Assay

The DAK activity was determined by a solid phase in vitro kinase assay after being brought down by immunoprecipitation (IP) or GST precipitation. The washed protein A or glutathione beads were then washed once with kinase buffer (50 mM Tris (pH 7.6), 10 mM $MgCl_2$) for 5 minutes at 4° C. The kinase reactions were carried out at room temperature for 30 minutes in a reaction volume of 20 µl containing 5:1 washed IP or GST beads, 1 μl [γ-$^{32}$P] ATP (10 μCi at 5000 Ci/mmol, Amersham) and 14 μl kinase buffer. 20 μl 1×SDS sample buffer was added to stop reactions and samples were heated for 5 minutes at 100° C. The samples were subjected to 10% SDS-PAGE and transferred to nitrocellulose membranes. The membranes were exposed to X-ray films or quantitated as indicated.

Results

Only the GST-fusion protein containing middle, but not N-terminal or C-terminal of Dsh, could bring down the kinase activity, suggesting the kinase binds to the middle region of Dsh. The Dishevelled associated kinase activity was eluted from Dsh immuno-complex in high salt conditions and the eluted kinase activity could re-bind to GST-fusion protein containing the middle region of Dsh but not to GST-proteins containing only the N- or C-terminal region of Dsh. The Dsh associated kinase activity precipitated using GST-DM increased as Dsh became progressively phosphorylated during Drosophila embryogenesis. Thus, the kinase precipitated by GST-DM in vitro is likely to be the same as that which phosphorylates Dsh during development.

Example 2
DAK Binds to a Conserved Region on Dishevelled

To further characterize the interaction between Dsh and its associated kinase, we mapped more precisely the region on Dsh which can interact with the kinase. Since the middle region of Dsh (DM) which contains the conserved PDZ-domain and flanking sequences can bind to DAK, we generated GST-fusion proteins containing smaller segments of the DM region. DAK did not bind to the PDZ domain but instead it bound to a 36 amino acid segment (DM5) N-terminal to the PDZ domain (FIG. 2). The binding properties were the same for the kinase activity eluted from immunoprecipitated endogenous Dsh and that precipitated from crude lysate by GST-fusion proteins, suggesting again that these two assays measured the same kinase. This region of Dsh is well conserved among Drosophila, Xenopus, and mammals.

Using a kinase assay in which substrate was impregnated in a polyacrylamide gel ("in-gel kinase assay", a modification of the above-described in vitro kinase assay), we determined the molecular mass of DAK. DAK was eluted from endogenous Dsh immunoprecipitated from embryo and fractionated on a SDS gel. After electrophoresis, proteins were renatured and incubated with [γ-$^{32}$P]-ATP to allow the kinase to phosphorylate its substrate (GST-DM5) which was imbedded in the gel. A polypeptide of 110 kDa appeared to account for the major DAK activity and two polypeptides of approximately 125 and 64 kDa appeared to represent minor activity.

Western Blotting

Proteins were subjected to SDS-PAGE and transferred to nitrocellulose membranes. The membranes were blocked with TBST (25 mM Tris (pH 8.0), 150 mM NaCl, 0.1% Tween 20) 5% non-fat milk for 1 hour at room temperature and blotted with primary antibodies in the blocking solution overnight at 4° C. The membranes were then blotted with horseradish peroxidase (HRP)-conjugated reagents, protein A for rabbit polyclonal antibodies and anti-mouse IgG for mouse monoclonal antibodies, in the blocking solution for 30 minutes at room temperature. The HRP was detected using the Enhanced Chemiluminescence (ECL) reagents (Amersham).

Example 3
Purification and Microsequencing of DAK

Using GST-DM5 precipitation plus in vitro phosphorylation as an assay to monitor DAK activity, we purified DAK 60,000 fold from Drosophila embryos in a procedure with an average yield of 8%.

Protein purification was carried out using the following step-wise procedure, as follows:

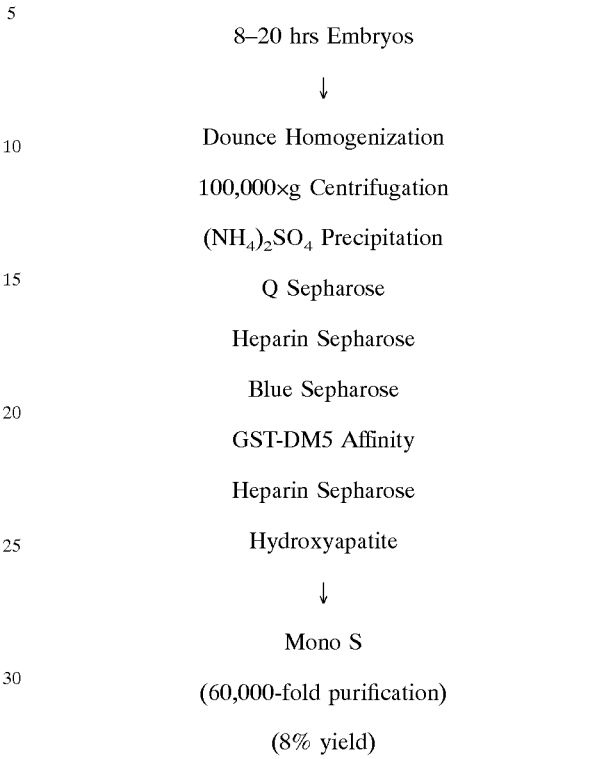

8–20 hrs Embryos
↓
Dounce Homogenization 100,000×g Centrifugation $(NH_4)_2SO_4$ Precipitation Q Sepharose Heparin Sepharose Blue Sepharose GST-DM5 Affinity Heparin Sepharose Hydroxyapatite
↓
Mono S (60,000-fold purification)

(8% yield)

All purification steps were carried out at 4° C. All the chromatography steps were performed using an fast protein liquid chromatography (FPLC) station (Pharmacia).

Detailed DAK Purification Protocol

DAK was purified from total 480 grams of 8–20 hour Drosophila embryos in eight batches. In each batch, 120 ml lysates from 60 grams embryos were prepared as described in Example 1 and centrifugated at 100,000×g for 1 hour at 4° C. The embryo S-100 were precipitated in 33% ammonium sulfate. The precipitates were dissolved in 30 ml buffer B (50 mM Tris (pH 7.6), 100 mM NaCl, 0.5% Nonidet P-40 (NP-40), 10 mM NaF, 5 mM NaPPi, 1 mM Na3VO4, 1.5 mM $MgCl_2$, 1 mM EGTA, 10% glycerol, and 1 mM benzamidine) with PIC, dialyzed for 4 hours against buffer A, and applied to 25 ml Q Sepharose HP equilibrated with buffer B. 100 ml flow-through was loaded directly onto a Heparin HP column (12 ml bed volume, Pharmacia) equilibrated with buffer B. The column was washed with buffer B and eluted with a 120 ml linear gradient from 0.1 to 1 M NaCl in buffer B. Active fractions (33 ml) were diluted with 30 ml buffer B without NaCl, and loaded onto 5 ml Blue Separose HP equilibrated with buffer B. The column was washed buffer B and eluted with 50 ml gradient from 0.1 to 2 M NaCl in buffer B. Active fractions (22.5 ml) were dialyzed against buffer B for 4–5 hr, added to 1.2 ml packed glutathione agarose beads which were loaded with GST-DM5 (8 mg/ml packed beads), and mixed in batch for 2 hr. The beads were packed into a 1 ml column (HP 5/5, Pharmacia), washed with buffer C (buffer B with 4 mM DTT) containing 0.16, 0.18, and 0.2 M NaCl respectively, and eluted with 10 ml linear gradient from 0.2 to 0.6 M NaCl in buffer C. Active fractions (5 ml) were diluted with 8 ml buffer D (50 mM Tris (pH 7.6), 0.5% NP-40, 10% glycerol, 1 mM DTT, 1 mM benzamidine), loaded onto a 1 ml HiTrap Heparin Sepharose HP (Pharmacia) equilibrated with 0.1 M NaCl in buffer D. The column was washed buffer D and eluted with 10 ml gradient from 0.1 to 1.0 M NaCl in buffer D. Active fractions (2.5 ml) were diluted with 7.5 ml buffer E (10 mM PIPES (pH 7.0), 0.5% NP-40, 10% glycerol, 1 mM DTT, 1 mM benzamidine), adjusted to pH 7.0, and loaded onto a 1 ml hydroxyapatite column equilibrated with 1 mM NaCl in buffer E. The column was washed with buffer E containing 5 mM $MgCl_2$, 0.9 M NaCl, and 1 mM NaCl respectively, eluted with 8 ml linear gradient from 1 mM NaCl to 300 mM sodium phosphate in buffer E. Active fractions (3 ml) were diluted with 6 ml buffer F (50 mM PIPES (pH 6.5), 0.5% NP-40, 10 mM NaF, 5 mM NaPPi, 1 mM $Na_3VO_4$, 1.5 MM $MgCl_2$, 1 mM EGTA, 10% glycerol, 1 mM benzamidine, 1 mM DTT), adjusted to pH 6.5, and loaded onto Mono S (1 ml, Pharmacia) equilibrated with 0.1 M NaCl in buffer F. The column was washed with 6 ml 0.1 M NaCl in buffer F and eluted with 15 ml linear gradient from 0.1 to 1.0 M NaCl in buffer F. Thirty fractions of 0.5 ml were collected and assayed for activity.

The results of the last step of the purification, a Mono S column chromatographic step, are shown in FIG. 3. DAK activity was eluted from Mono S column in fractions 12–14 (see FIG. 3). A polypeptide with molecular mass of 64 kDa was observed to coelute with the DAK activity. An in-gel kinase assay of fraction 14, which is the peak of DAK activity, showed that the 64 kDa polypeptide represented the major kinase activity in the fraction. The purification of the 64 kDa protein kinase was consistent with the previous observation which showed a 64 kDa kinase was co-immunoprecipitated with endogenous Dsh from *Drosophila* embryo.

After the final purification step, the Mono S column fractions containing the peak of DAK activity were pooled and fractionationed on SDS-PAGE. The 64 kDa polypeptide was recovered from the gel after staining with Sypro orange and digested with Lys-C proteinase and separated by high performance liquid chromatography to resolve individual peptides. Five peptide sequences ranging from 7 to 19 amino acids were determined by combination of Edman degradation and mass spectrometry (Fernandez et al. (1998) *Electrophoresis* 19:1036–1045).

Active fractions of Mono S column were pooled from all batches and separated on a 9% SDS-PAGE. The 64 kDa band was excised from gel after stained with Sypro Orange (Bio-Rad). The protein was digested in gel with Lys-C proteinase, separated on HPLC to resolve individual peptides, and peptide sequences were determined by a combination of Edman degradation and mass spectrometry.

Example 4
Cloning DAK cDNA and Analysis of DAK Domain Structure

The cDNA clones encoding DAK were isolated by screening a *Drosophila* 2–14 hr embryo cDNA library (Stratagene) with two degenerate oligo probes under low stringency. The oligo probes:
GAGAA(C/T)ACI(inosine)GCI(C/A)GI(C/T)TIGCCGCTCAAAATCAGAGACCIGCITCIGCI ACICAGAA (SEQ ID NO:10; derived from peptide sequence ENTARLAAQNQRPASATQK); and CGICA(A/G)AA(C/T)ACIATIGA(C/T)T(C/G)IGCIACIATIAAG (SEQ ID NO:11;
derived from peptide sequence RQNTIDSATIK) were end labeled with [$\gamma$-$^{32}$P] ATP. The filter lifts in duplicate were hybridized to the oligo probes at 50° C. for 16 hr in 5×SSC, 5× Denhardt's, 0.5% SDS, 100 µg/ml ssDNA. Filters were washed twice at room temperature for 15 min each in 2×SSC, 0.1% SDS and twice at 36° C. for 15 minutes each in 1×SSC, 0.1% SDS. Positive clones which were hybridized to both oligo probes were chosen for DNA sequencing.

Two cDNA clones were isolated by screening a 2–14 hour *Drosophila* embryo cDNA library with degenerate oligonucleotide probes based on the peptide sequences. One clone had an open reading frame that encodes 832 amino acids with a calculated molecular mass of 89 kDa. The other clone had an open reading frame that encodes 1058 amino acids with a calculated molecular mass of 115 kDa. Multiple stop codons in all three reading frames were identified in the 5' untranslated region of both cDNA, indicating that these cDNA clones encode full-length DAK.

Figure 4A:
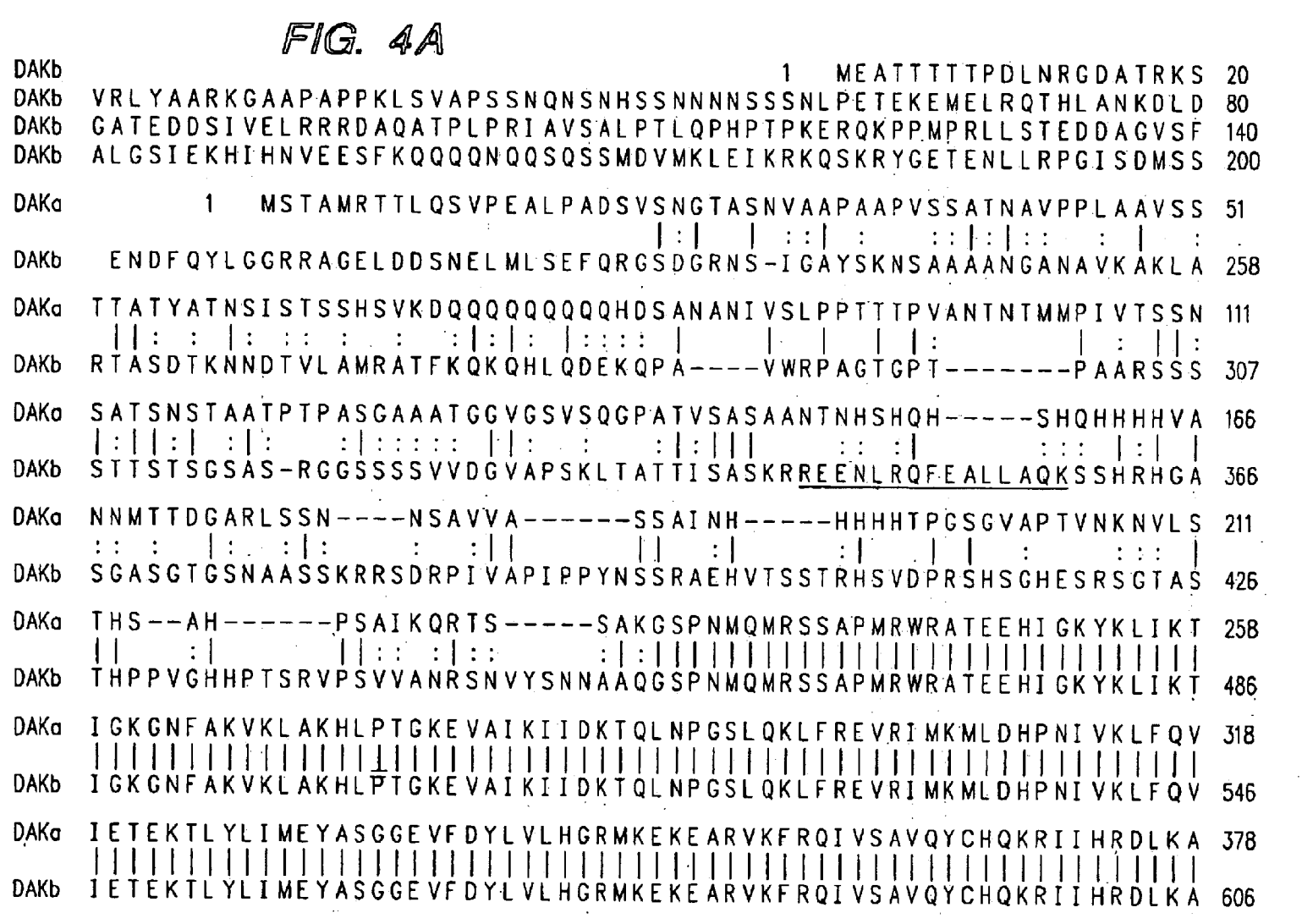

FIG. 4 shows the predicted amino acid sequences encoded by DAK. All five peptide sequences match the amino acid sequences of DAK. The two cDNA clones encode isoforms of DAK, DAKa and DAKb, which share the kinase domain in the middle and have similar C-terminal regions. The N-terminal regions of DAKa and DAKb differ from one another. Analysis of genomic DNA containing the DAK gene showed that both N-terminal sequences are in the same genomic region of approximately 20 kilobases, suggesting that they are two alternatively spliced isoforms.

A search of GenBank databases revealed that a segment C-terminal to the kinase domain contains an ubiquitin-associated (UBA) domain. This set of loosely conserved sequences is about 45–55 residues and is found in multiple classes of enzymes involved in ubiquitination and DNA repair, and in several protein kinases. The presence of UBA domain in DAK indicates that DAK is regulated by ubiquitin through tagging for degradation or membrane recruitment.

Figures 5, 6:
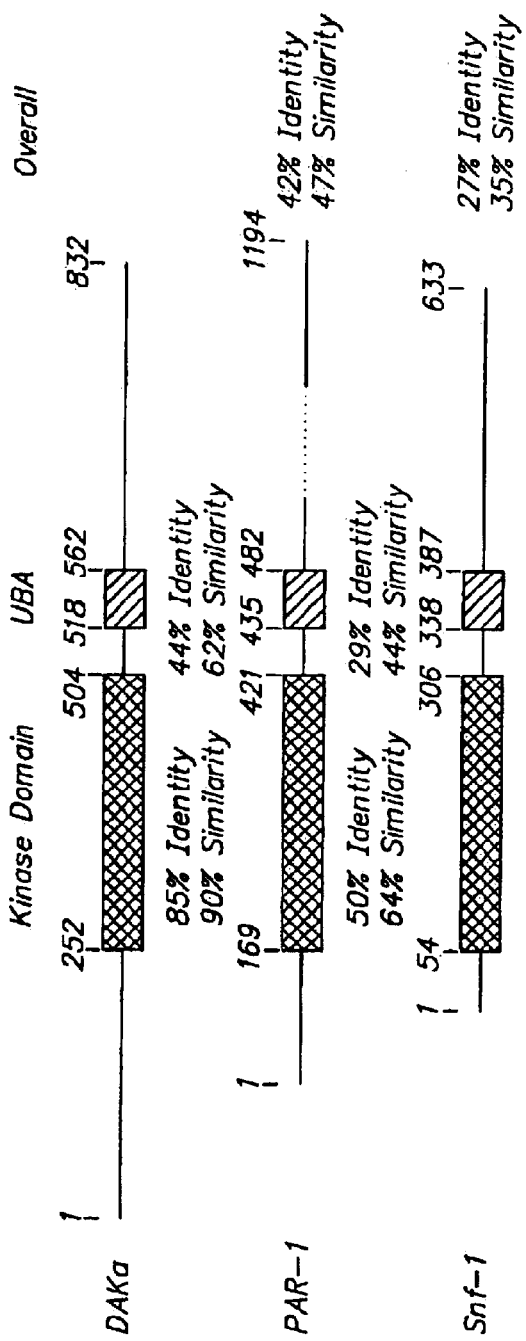
FIG. 5 shows the domain structure of DAK compared to that of PAR-1 and Snf-1 also showing the percentage identity and similarity of each to DAKa.
FIG. 6 shows a comparison of the UBA domain of DAKa with each of PAR-1 and Snf-1.

A data base search also revealed that DAK has significant homology to PAR-1 in *C. elegans* (42% identity and 47% similarity) and to Snf1 in *Saccharomyces cerevisiae* (27% identity and 35% similarity) (FIG. 5).

DAK, PAR-1 and Snf1 are similar in having a kinase domain followed by a UBA domain. The most conserved regions are in the kinase domain (85% identity and 90% similarity with PAR-1 and 50% identity and 64% similarity with Snf1) (FIG. 5). DAK's UBA domain also shows 44% identity and 62% similarity with PAR-1 and 29% identity and 44% similarity with Snf1, as shown in FIGS. 5 and 6.

Example 5
Size Analysis of Polypeptides Encoded by DAKa and DAKb cDNAs

The DAKa and DAKb were translated in a TNT T3 transcription/translation kit (Promega) in the presence of $^{35}$S-methionine according to the instruction of the manufacturer. The translated proteins were subjected to SDS-PAGE and autoradiography.

The cDNAs for DAKa and DAKb were translated in vitro and analyzed by SDS-PAGE. The polypeptides encoded by DAKa and DAKb cDNA migrated at about 105 and 130 kDa respectively on the SDS gel, which are slightly larger than the predicted molecular masses of 89 and 115 kDa, suggesting that they are post-translationally modified.

Example 6
Analysis of DAK cDNA

To confirm that the cloned cDNA indeed encodes the Dishevelled associated kinase activity, antiserum to DAK was used to deplete DAK activity from Clone-8 cell lysates and from embryo homogenates. To show that the DAK antibody produced using recombinant DAK recognizes a Dsh-associated protein, Dsh was immunoprecipitated from Clone-8 cells with an affinity purified anti-Dsh antibody and DAK was detected in the Dsh immunoprecipitates using DAK antibody.

Preparation of Recombinant Proteins and Antibodies to DAK

The GST fusion proteins were expressed in *E. coli* strain BL21(DE3)plyS. The *E. coli* cells were actively grown at 37° C. in LB medium and expression was induced by addition of IPTG to 0.1 mM for 2 hours at 37° C. The harvested cells were disrupted by sonication in 1×PBS with 1% TritonX-100 and PIC. The GST fusion proteins were bound to glutathione agarose (Pharmacia) for 1–2 hours at 4° C. The beads were washed extensively with 1×PBS containing 1% TritonX-100 and 1 mM benzamidine and then with a storage solution (1×PBS, 1% TritonX-100, 10% glycerol, PIC). The beads were resuspended in the storage solution to a 50% slurry and stored at −80° C.

The His-tagged fusion proteins were expressed in *E. coli* strain BL21(DE3) or BL21(DE3)plyS. The fusion proteins were purified under denaturing condition using Ni-NTA agarose (Qiagen) as described by manufacturer and used for productions of rabbit polyclonal antibodies (BABCO). The anti-Dsh antibodies were generated against His-tagged DN and DM and affinity-purified against GST-DN and GST-DM coupled to Affi-Gel 10 (Bio-Rad) using standard procedures. The anti-DAK antibody was generated against His-tagged DAKa C-terminal fragment (469–832).

Results

A polyclonal antibody raised against a recombinant protein containing C-terminal segment (amino acids 469–832) of DAKa, which is shared by both isoforms of DAK, reacted with endogenous DAK from embryo and Clone-8 cells. An immune serum against DAK precipitated two polypeptides of 105 and 130 kDa from embryos and Clone-8 cells, while a preimmune serum did not. The sizes of these two proteins are consistent with the polypeptides generated from cDNA for DAKa and DAKb respectively in the in vitro translation experiment.

The 105 kDa protein product from DAKa is more abundant than that from DAKb in both embryo and Clone-8 cells. Accordingly, the DAKa protein was focused on in these studies. A 64 kDa polypeptide from embryo was also detected by the anti-DAK antibody after longer exposure of the blot. The detection of 105, 130 and 64 kDa polypeptides by anti-DAK antibody are consistent with earlier experiments which showed three polypeptides with these sizes have Dishevelled associated kinase activity. The 64 kDa polypeptide may represent a proteolytic product from DAK, and explains why a 64 kDa protein kinase was found in the final purification step.

Example 7
DAK Activates DSH and its Mouse Homolog Dvl3 in the Wnt Pathway

Dsh is phosphorylated during embryonic stages in which Wingless signaling is required. To determine the role of DAK in the Wnt/Wingless pathway tests were conducted to determine whether DAK could modify Dishevelled's activity in the Wnt pathway. The tests were carried out using cultured mammalian cells, since the Wnt/β-catenin pathway is well conserved among species and many components of the pathway are functionally exchangeable in different organisms. For example, *Drosophila* Wingless functions in mammalian cells (Ramakrishna et al., *A.M.C.*, Developmental Suppl. 95–103 (1993)), *Drosophila* Dsh in *Xenopus* (Rothbacher et al., *Dev. Biol.* 170:717–721 (1995)), mouse Dsh in *Drosophila* (Klingensmith et al (1996) *Mech. Dev.* 58:15–26), mammalian GSK-3β in *Drosophila* (Siegfried et al. (1992) *Cell* 71:1167–1179), and *Drosophila* Armadillo and dTCF in mammalian cells (van de Wetering et al. (1997) *Cell*, 88:789–799). The LEF1/TCF reporter assay was used for this study as it has been used extensively in previous studies of Wnt signaling (van de Wetering et al., supra; Hsu et al. (1998) *Mol. Cell Biol.* 18:4807–4818).

Plasmids

The LEF1 reporter 7LEF-fosluc and LEF1 expression plasmids have been described (Hsu et al. (1998) *Mol. Cell Biol.* 18:4807–4818). Axin and Wnt1 expression plasmids have also been described (Sakanaka et al. (1998) *Proc. Natl. Acad. Sci. USA* 95:3020–3023). The MEKK expression plasmid was from Stratagene. The Renilla luciferase expression plasmid pRL-TK was from Promega. The DNA containing various regions of Dsh were generated by polymerase chain reaction (PCR) and cloned into a GST expression vector. The 3' end of DAKa cDNA was modified by PCR to replace the stop codon with an XbaI site. The kinase dead DAKa was generated using overlapping PCR to replace the conserved lysine 282 to alanine. The Dsh and Dvl3 cDNA were generated by PCR with a XbaI site at 3' end to replace stop codons. The pcDNA 3.1 (Invitrogen) was modified by addition of indicated tags and a stop codon 3' after the XbaI site. These cDNA were cloned into the modified pcDNA3.1 expression plasmid with XbaI site at 3' end. In the final constructs, cDNA are expressed from a CMV promoter, and are C-terminal tagged.

LEF1 Reporter Assay

NIH3T3 cells were grown in DMEM with 10% bovine serum. Active grown cells were seeded into 12-well plates the day before transfection. The transfection was carried out using Superfect (Qiagen). Cells in each well were transfected with 0.1 μg 7LEF-fosluc, 0.05 μg LEF1 expression plasmid, or 0.01 μg pRL-TK, test plasmids, and the vector plasmid to total 1.5 μg. 24–26 hours after transfection, the luciferase activities were determined using a dual luciferase assay system (Promega).

Results

Transfection of Dsh into the NIH3T3 cells barely activated the LEF1 reporter. However in the presence of DAK, there was a dramatic dose-dependent potentiation of the activation of the LEF1 reporter by Dsh. A 10-fold activation of the reporter was observed by Dsh and DAK acting together comparing to a 1.3-fold activation by Dsh alone. A "kinase dead" mutant form of DAK did not have this effect. The expression of DAK in the absence of Dsh failed to activate the reporter at all, supporting the notion that DAK and Dsh interact. The effect of DAK on Dishevelled's mouse homolog Dvl3 in the LEF1 reporter assay was also tested. The co-expression of Dvl3 with DAK stimulated the LEF1 reporter to a greater extend than Dvl3 alone did and the activation depended on the amount of DAK. A remarkable 95-fold activation of the reporter was observed with DAK and Dvl3 acting together comparing to a 5.5-fold with Dvl3 alone. As seen with Dsh, the kinase dead DAK did not significantly enhance the activation of the LEF1 reporter by Dvl3.

Axin is a negative regulator of the Wnt pathway and it acts downstream of Dvl to suppress Wnt signaling (Itoh et al. (1998) *Curr. Biol.* 8:591–594). Approximately 80 to 90% activation of the LEF1 reporter by Wnt1 or Dvl3 was suppressed by Axin. The same extent of suppression was also observed for the activation of the LEF1 reporter by Dvl3 plus DAK. Since the activation of LEF1 reporter by DAK was fully dependent on the expression of Dsh or Dvl3 and the activation was strongly suppressed by Axin, it can be concluded that DAK activates LEF1 reporter through components of the Wnt pathway that are upstream of Axin.

The results provided here showed that Dsh was progressively phosphorylated in *Drosophila* embryos in the stages when Wg signaling is required. The functional relevance of this phosphorylation is suggested by the fact that most (around 60%) of the endogenous Dsh is modified in this way. This result is consistent with a previous observation which showed that Dsh was hyperphosphorylated upon Wg stimulation in tissue culture cells and the phosphorylation seemed to be correlated with stabilization of Armadillo (Yanagawa et al. (1995) *Genes Dev.* 9:1087–1097).

Taken together, these data shows that DAK is responsible for the phosphorylation of Dsh seen during embrogenesis and during Wg stimulation of cells.

Example 8
DAK Suppresses Dsh and Its Mouse Homolog Dvl3 in the Jnk Pathway

Dsh is a multi-functional protein that participates in both the Wg/Armadillo signaling and planar polarity pathways. Dsh activates the JNK pathway to control planar polarity in *Drosophila*. Expression of Dsh in NIH3T3 cells also strongly activates JNK and results in phosphorylation of c-Jun at a specific site. Since DAK phosphorylates Dsh, forms complexes with Dsh and activates Dsh in Wnt signaling, efforts were made to determine if DAK regulates Dsh in the JNK pathway.

Jnk Assay (Phosphorylation of c-Jun)

The JNK assay was performed as described (Boutros et al. (1998) *Cell* 94:109–118). NIH3T3 cells were grown and transfected as described above. Cells were seeded into 12-well plates the day before transfection. Cells in each wells were transfected with 0.3 µg c-Jun, testing plasmids, and vector DNA added to bring the total amount of DNA to 1.5 µg. 22–24 hours after transfection, cells were lysed and subjected to SDS-PAGE. Proteins were transferred to nitrocellulose membranes. The membranes were blotted with an antibody specific to Phosphorylation at S63 of c-Jun (New England Biolab) in TBST 5% BSA overnight at 4° C. and then with HRP-conjugated anti-rabbit antibodies. HRP was detected with ECL reagent.

Results

NIH3T3 cells were transfected with Dsh and c-Jun. The c-Jun acts as a in vivo substrate to monitor JNK activity. The phosphorylation of c-Jun was examined using an antibody that recognizes phosphoserine at residue 63, a major JNK phosphorylation site. Expression of increasing amounts of Dsh in NIH3T3 cells induced increasing phosphorylation of c-Jun at S63 in a dose-dependent manner, indicating Dsh activated JNK. Overexpression of activated MEKK, a known JNK activator, induced c-Jun phosphorylation as predicted. Expression of Dvl3, a mouse homolog of Dsh, in NIH3T3 also activated JNK to a similar level as Dsh and the activation was dose dependent. When Dsh was co-expressed with wild type but not kinase dead DAK, the phosphorylation of c-Jun was dramatically reduced in a dose-dependent manner. This indicated that DAK suppresses Dsh in its activation of JNK. Wild type DAK also suppressed Dvl3 in its activation of JNK. The amount of DAK used for suppression of Dsh and Dvl3 in JNK activation was comparable to that used for activation of Dsh and Dvl3 in Wnt signaling.

*Drosophila* Dishevelled is required for Wg/Armadillo signaling and planar polarity pathway. In embryos, Dsh acts downstream of Frizzled and *Drosophila* Frizzled 2 to transduce Wg signal. In the developing eye, Dsh acts downstream of Frizzled to transduce signals through the JNK pathway to control planar polarity. Work was conducted to show how Dsh discriminates signals from upstream and then activates proper downstream elements since the Frizzled acts as receptor in both pathways.

Using a LEF1 reporter assay, it was demonstrated that DAK significantly activates Dsh and Dvl3 in the Wnt/β-catenin pathway in cell culture. DAK appears to be an upstream activator of Dsh and Dvl3 based on the findings that Dsh is phosphorylated during Wg signaling, that DAK binds and phosphorylates Dsh, and that DAK activates Dsh and Dvl3 in LEF1 reporter assays. In contrast to its role as a positive regulator in the Wnt/β-catenin pathway, DAK strongly suppresses Dsh and Dvl3 in their activation of JNK pathway, showing that DAK acts as negative regulator in control of the JNK/planar polarity pathway. The dual functions of DAK may provide a mechanism for Dsh to discriminate these two signaling events, namely by promoting Wnt signaling and suppressing the JNK pathway (FIG. 1). Ectopic expression of Wg suppressed Dsh function in the planar polarity pathway.

Example 9

Suppression of Wnt Signaling by a 36 Amino Acid DAK Binding Peptide from Dvl3

As described in Example 2, and shown in FIG. 2, a 36-amino acid fragment of Dsh binds to DAK. This 36-amino acid region is well conserved among Dsh and mammalian homologs, Dvl, as shown in FIG. 2. To examine whether this fragment could interfere with the interaction between endogenous Dvl and DAK, a 36-amino acid DAK-binding peptide from Dvl3 was expressed in CHO cells, and its effect on Wnt-induced, and β-catenin-induced, activation of LEF1 reporter activity was determined.

The 36-amino acid DAK-binding peptide from mouse Dvl3 (amino acids 211–246; SRLMRRHKRRRRKQKVS-RIERSSSFSSITDSTMSLN; SEQ ID NO:8), designated D3DM5, was expressed as a GST fusion protein (GST-D3DM5). Its expression was driven by a CMV promoter.

CHO cells were grown in F12 medium supplemented with 10% fetal bovine serum. Cells were seeded into wells of 12-well tissue culture dishes one day before transfection. Duplicate transfections were carried out using Superfec transfection agent (Qiagen). Cells in each well were transfected with 0.1 µg LEF1 reporter construct, 12.5 ng LEF1, 10 ng Renilla luciferase reporter pRL-TK, 0.1 µg Wnt1, or 50 ng β-catenin, and 0.6 µg GST-D3DM5 cDNAs. The final amount of DNA per well was 1.5 µg, and vector DNA compensated when other DNAs were omitted. 24 hours after transfection, luciferase activities were determined using a dual luciferase assay system (Promega). Luciferase activity obtained with LEF1 reporter construct was normalized by Renilla luciferase activity, to control for transfection efficiencies.

As shown in FIG. 7, D3DM5 peptide suppressed Wnt-induced, but not β-catenin-induced, activation of LEF1 reporter activity, suggesting that the inhibition occurred upstream of β-catenin.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. An isolated polynucleotide comprising a nucleotide sequence that encodes a polypetide having at least about 95% amino acid sequence identity to the amino acid sequence set forth in SEQ ID NO:2 or SEQ ID NO:4, wherein said polypeptide catalyzes the phosphorylation of a peptide having an amino acid sequence of any one of SEQ ID NOs:5–9 or SEQ ID NO:12.

2. An isolated polynucleotide comprising a nucleotide sequence that encodes a polypeptide comprising the amino acid sequence depicted in SEQ ID NO:2 or 4.

3. The isolated polynucleotide of claim 2, wherein said polynucleotide comprises the nucleotide sequence depicted in SEQ ID NO:1 or 3.

4. A recombinant vector comprising the polynucleotide of claim 1 or claim 2.

5. An isolated host cell comprising the polynucleotide of claim 1 or claim 2.

6. The isolated host cell of claim 5, wherein the cell is a prokaryotic cell.

7. The isolated host cell of claim 5, wherein the cell is a eukaryotic cell.

* * * * *